(12) United States Patent
Eliot et al.

(10) Patent No.: US 9,371,546 B2
(45) Date of Patent: Jun. 21, 2016

(54) ENHANCING D-XYLOSE AND L-ARABINOSE UTILIZATION IN ZYMOMONAS CELLS

(71) Applicant: E I DU PONT DE NEMOURS AND COMPANY, Wilmington, DE (US)

(72) Inventors: Andrew C Eliot, Wilmington, DE (US); Luan Tao, Wallingford, PA (US); Paul V Viitanen, West Chester, PA (US)

(73) Assignee: E I DU PONT DE NEMOURS AND COMPANY, Wilmington, DE (US)

( * ) Notice: Subject to any disclaimer, the term of this patent is extended or adjusted under 35 U.S.C. 154(b) by 0 days.

(21) Appl. No.: 14/312,725

(22) Filed: Jun. 24, 2014

(65) Prior Publication Data

US 2015/0368674 A1 Dec. 24, 2015

(51) Int. Cl.
 C12P 7/06 (2006.01)
 C12N 1/21 (2006.01)
 C07K 14/195 (2006.01)

(52) U.S. Cl.
 CPC ............... *C12P 7/065* (2013.01); *C07K 14/195* (2013.01); *C12P 7/06* (2013.01)

(58) Field of Classification Search
 None
 See application file for complete search history.

(56) References Cited

U.S. PATENT DOCUMENTS

| | | | |
|---|---|---|---|
| 4,683,202 | A | 7/1987 | Mullis |
| 5,514,583 | A | 5/1996 | Picataggio et al. |
| 5,712,133 | A | 1/1998 | Picataggio et al. |
| 5,843,760 | A | 12/1998 | Zhang et al. |
| 6,566,107 | B1 | 5/2003 | Zhang |
| 7,223,575 | B2 | 5/2007 | Zhang et al. |
| 7,629,156 | B2 | 12/2009 | Viitanen et al. |
| 7,741,084 | B2 | 6/2010 | Viitanen et al. |
| 7,741,119 | B2 | 6/2010 | Viitanen et al. |
| 7,989,206 | B2 | 8/2011 | Viitanen et al. |
| 7,998,722 | B2 | 8/2011 | Viitanen et al. |
| 8,247,208 | B2 | 8/2012 | Caimi et al. |
| 8,476,048 | B2 | 7/2013 | Caimi et al. |
| 8,623,623 | B2 | 1/2014 | Kahsay et al. |
| 8,679,822 | B2 | 3/2014 | Caimi et al. |
| 8,911,983 | B2 | 12/2014 | Caimi et al. |
| 2003/0162271 | A1 | 8/2003 | Zhang et al. |
| 2011/0143408 | A1 | 6/2011 | Yang |
| 2012/0156746 | A1 | 6/2012 | Caimi et al. |
| 2013/0157331 | A1 | 6/2013 | Caimi et al. |
| 2013/0157332 | A1 | 6/2013 | Hitz et al. |

FOREIGN PATENT DOCUMENTS

| | | |
|---|---|---|
| KR | 20060060389 A | 6/2006 |
| WO | 9528476 A1 | 10/1995 |
| WO | 2012082711 A1 | 6/2012 |
| WO | 2013096366 A1 | 6/2013 |
| WO | 2013106172 A1 | 7/2013 |

OTHER PUBLICATIONS

GenBank Accession No. AE008692, Jan. 2014, 2 pages.*
Chou et al. "Genetic Engineering and Improvement of a Zymomonas mobilis for Arabinose Utilization and Its Performance on Pretreated Corn Stover Hydrolyzate", J. Biotechnol. Biomater. 5:2, 2015, 8 pages.*
Altschul et al., "Basic Local Alignment Search Tool", J. Mol. Biol., (1990) vol. 215, pp. 403-410.
Deshpande, "Ethanol Production from Cellulose by Coupled Saccharification/Fermentation using *Saccharomyces cerevisiae* and Cellulose Complex from Sclerotium rolfsii UV-8 Mutant*", Applied Biochemistry and Biotechnology, vol. 36 (1992) pp. 227-234.
Feldmann et al., "Pentose metabolism in Zymomonas mobilis wild-type and recombinant strains", Appl. Microbiol. Biotechnol. 38:354-61 (1992).
Follens et al., "acs1 of Haemophilus influenzae Type a Capsulation Locus Region II Encodes a Bifunctional Ribulose 5-Phosphate Reductase- CDP-Ribitol Pyrophosphorylase", J. of Bacteriology 181:2001-2007 (1999).
Higgins et al., "CLUSTAL V: improved software for multiple sequence alignment", CABIOS, vol. 8, No. 2 (1992) pp. 189-191.
Higgins et al., "Fast and sensitive multiple sequence alignments on a microcomputer", CABIOS Communications, vol. 5, No. 2 (1989) pp. 151-153.
Mohagheghi et al., "Performance of a newly developed integrant of Zymomonas mobilis for ethanol production on corn stover hydrolysate", Biotechnology Letters, 25:321-325 (2004).
Ohara et al., "One-sided polymerase chain reaction: The amplification of cDNA" Proc. Natl. Acad. Sci, USA 86:5673 (1989).
Pearson, Comput. Methods Genome Res., [Proc. Int. Symp.] (1994), Meeting Date 1992, 111 20. Editor(s): Suhai, Sandor. Plenum: New York, NY.
Rychlik, W., "Selection of Primers for Polymerase Chain Reaction", Methods in Molecular Biology, vol. 15, PCR Protocols: Current Methods and Applications, edited by B.A. White, 1993 Humania Press, Totowa, N.J.
Seo et al., "The genome sequence of the ethanologenic bacterium zymomonas mobilis ZM4", Nature Biotechnology 23 (1) 63-68 (2005).
Tabor et al., "A bacteriophage T7 RNA polymerase/promoter system for controlled exclusive expression of specific genes", Proceedings of the National Academy of Sciences USA, vol. 82 (1985) pp. 1074-1078.
Thein, S. et al., "The use of synthetic oligonucleotides as specific hybridization probes in the diagnosis of genetic disorders", in Human Genetic Diseases: A Practical Approach, K. E. Davis Ed., (1986) pp. 33-50, IRL: Herndon, Va.
Thompson et al., "Clustal W: improving the sensitivity of progressive multiple sequence alignment through sequence weighting, position-specific gap penalties and weight matrix choice", Nucleic Acids Research, 1994, vol. 22, No. 22, pp. 4673-4680.

(Continued)

Primary Examiner — David J Steadman

(57) ABSTRACT

Disrupting expression of a protein encoded by the region of the *Zymomonas* genome called ZMO0353 in the genomic sequence of the ZM4 strain was found to improve the use of xylose in a recombinant xylose utilizing *Zymomonas* cell. In addition, utilization of both xylose and arabinose was improved in a xylose and arabinose utilizing *Zymomonas* cell with this disruption, and increased ethanol production was achieved.

12 Claims, 5 Drawing Sheets

(56) References Cited

OTHER PUBLICATIONS

Walker et al., "Isothermal in vitro amplification of DNA by a restriction enzyme/DNA polymerase system", Proceedings of the National Academy of Sciences USA, vol. 89, Jan. 1992, pp. 392-396.

Zhang et al., "Metabolic Engineering of a Pentose Metabolism Pathway in Ethanologenic Zymomonas mobilis", Science 267:240-3 (1995).

Zolli et al., "Reduction Precedes Cytidylyl Transfer without Substrate Channeling in Distinct Active Sites of the Bifunctional CDP-Ribitol Synthase from Haemophilus influenzae", Biochemistry 40:5041-5048 (2001).

Database Geneseq, "Zymomonas Mobilis ZM4 Ethanol Production", DNA Seq ID No. 2587, XP002744229, Database Accession No. ARW41203 (2004).

Database WPI Week 200682 Thomson Scientific, London, GB AN 2006-810156 XP002744228, "A Novel Gene Involved in Producing Ethanol in Zymomonas Mobilis ZM4 is Provided to Simply Mass-Produce the Ethanol With High Yield at Relatively Low Cost by Over-Expressing It" (2006).

International Search Report, PCT International Application No. PCT/US2015/037328, mailed Sep. 28, 2015.

* cited by examiner

SEQUENCE LISTING

<160> NUMBER OF SEQ ID NOS: 44

<210> SEQ ID NO 1
<211> LENGTH: 1341
<212> TYPE: DNA
<213> ORGANISM: Zymomonas mobilis

<400> SEQUENCE: 1

```
atggctgttg ccgttatttt gggaggcggg aaaggcaccc gttttggtga tccgctaccc      60
aagcaattca aggtattagg tggaaagccg atcatccaat ataccttgga ggcctttat     120 tctcatccgg cgattgatga aattattgtg acctatccgg ttgaataccg gaaagagatt     180
gcaaagataa ccgcgccttt ttctaaaaaa ccgatccatt tggtggcggg gggtgcttcc     240
cgcatggaaa caactatggc ggctttggct gcggcgggtg atcgtcatgt taagatttta     300
tttcatgatg cggttcgccc ttttgtttcc catgatatca tcagcgatag tttggttgct     360
cttgatcggc atcaggccgt tgatgttgtt attccaacgg ccgatactat cgtttctttg     420
aatgaggcgc aggatcattt actgtctatc cccaaacgta gcctgctacg ccgtggacaa     480
acgccgcaag gtttctgggg cgattctctg gcggctgctt atcgggcgat agatcctgaa     540
attcttgacc gttttccga tgattgcggt gtatttcttt atcaaaatcc tgatgctgat     600
atcggtgtgg tcaccggtga tgataaaaat atcaaaatta cgacaccgat agatttcttt     660
```

```
ttggctgaac aaatcctcta ttcagggcag gcggctagcc gatcagtggt ttccgaggaa    720
aaaagccaga agtccgtggt tcttttttggc gcttcatcag gattgggcgc ggcggctgca    780
aaagctatgg aagccaaggg ctggcaagtc tttgccgctt cgcgtagcac ggggggtcgat    840
atttgtgatc ctgaacaggt gaacggtttt tttaaggaag tagcttctaa aacatctgaa    900
attgacgcgg ttgcagtttt ctccggtgtt ttaaaaaccg gcaagattac agaaatgagc    960
cgtgaagaaa tccgtcaaat gatagatgtc aatttgatcg gttcattaaa tgtggccttg   1020
gcttcttttc cctatttgaa gaagtcatct ggtcatttat tgatggttag ctccagtagt   1080
tattttcgcg ggcgtgctaa ttcagcggtt tattcatctt ccaaagcggc ggtagttaat   1140
ttaacgcaag ccctttctga agaatgggca gaggataata ttgcggtttc ctgtattgct   1200
ccacggcgtg ccaatacgcc gatgcggagg aaggctttcc cgcatgagaa tccggcaatc   1260
tgtcttgacc ccgatattgt cagtcagcag gtgatcgcga tgttggagca tccccagaca   1320
ggtttaatca aacatattta t                                              1341
```

<210> SEQ ID NO 2  
<211> LENGTH: 1341  
<212> TYPE: DNA  
<213> ORGANISM: Zymomonas mobilis

<400> SEQUENCE: 2

```
atggctgttg ccgttatttt gggaggcggg aaaggcaccc gttttggtga tccgctaccc     60
aagcaattca aggtattagg tggaaagccg atcatccaat ataccttgga ggcctttat    120
tctcattcgg cgattgatga aattattgtg acctatccgg ttgaataccg gaaagagatt    180
gcaaagataa ccgcgccttt ttctaaaaaa ccgatccatt tggtggcggg gggtgcttcc    240
cgtatggaaa caaccatggc ggctttggct gcggcgggtg atcgtcatgt taagatttta    300
tttcatgatg cggttcgccc ttttgttccc catgatatca tcagcgatag tttggttgct    360
cttgatcggc atcaggctgt tgatgttgtt attccaacgg ccgatactat cgtttctttg    420
aatgaggcgc aggatcattt actgtctatc cccaaacgta gcctgctacg ccgtggacaa    480
acgccgcaag gttctggggg cgattctctg gcggctgctt atcgggcgat agatcctgaa    540
attcttgacc gttttttccga tgattgcggt gtatttcttt atcaaaatcc tgatgctgat    600
atcggtgtgg tcaccggtga tgataaaaat atcaaaatta cgacaccgat agatttctt    660
ttggctgaac aaatcctcta ttcagggcag gcggctagcc gatcagtggt ttccgaggaa    720
aaaagccaga agtccgtggt tcttttttggc gcttcatcag gattgggcgc ggcggccgct    780
aaagctatgg aagccaaagg ctggcaagtc tttgccgctt cgcgtagcac ggggggtcgat    840
atttgtgatc ctgaacaggt gaatggtttt tttaaggaag tagcctctaa aacatctgaa    900
attgacgcgg ttgcagtttt ttccggtgtt ttgaaaaccg gcaagattac agaaatgagc    960
cgtgaagaaa tccgtcaaat gatagatgtc aatttgatcg gttcattaaa tgtggccttg   1020
acttcttttc cctatttgaa gaagtcattc ggtcatttgt taatggttag ctccagtagt   1080
tattttcgcg ggcgtgccaa ttcagcggtt tattcatctt ccaaagcggc ggtggttaat   1140
ttaacgcaag ccctttctga agaatgggca gaggataata ttgcggtttc ctgtattgct   1200
ccacggcgcg ccaatacgcc gatgcggagg aaggctttcc cgcatgagaa tccggcaatc   1260
tgtcttgacc ccgatattgt cagtcagcag gtgatcgcga tgttggagca tccccagaca   1320
ggtttaatca aacatattta t                                              1341
```

<210> SEQ ID NO 3
<211> LENGTH: 1341
<212> TYPE: DNA
<213> ORGANISM: Zymomonas mobilis

<400> SEQUENCE: 3

| | | | | | | |
|---|---|---|---|---|---|---|
| atggctgttg | ccgttatttt | gggaggcggg | aaaggcaccc | gttttggtga | tccgctaccc | 60 |
| aagcaattca | aggtattagg | tggaaagccg | atcatccaat | ataccttgga | ggccttttat | 120 |
| tctcatccgg | cgattgatga | aattattgtg | acctatccgg | ttgaataccg | gaaagagatt | 180 |
| gcaaagataa | ccgcgccttt | ttctaaaaaa | ccgatccatt | tggtggcggg | gggtgcttcc | 240 |
| cgcatggaaa | caaccatggc | ggctttggct | gcggcgggtg | atcgtcatgt | taagatttta | 300 |
| tttcatgatg | cggttcgccc | ttttgtttct | catgatatca | tcagcgatag | tttagttgct | 360 |
| cttgatcggc | atcaggctgt | tgatgttgtt | attccaacgg | cggatactat | cgtttctttg | 420 |
| aatgaggcgc | aggatcattt | actgtctatc | cccaaacgta | gcctgctacg | ccgtggacaa | 480 |
| acgccgcaag | ttctggggg | cgattctctg | gcggctgctt | atcgggcgat | agatcctgaa | 540 |
| attcttgacc | gttttccga | tgattgcggt | gtatttcttt | atcaaaatcc | tgatgctgat | 600 |
| atcggtgtgg | tcaccggtga | tgataaaaat | atcaaaatta | cgacaccgat | agatttcttt | 660 |
| ttggctgaac | aaatcctcta | ttcagggcag | gcggctagcc | gatcagtggt | ttccgaggaa | 720 |
| aaaagccaga | gtccgtggt | tcttttttgga | gcttcatcag | gattgggcgc | ggcggccgct | 780 |
| aaagctatgg | aagccaaatg | ctggcaagtc | tttgccgctt | cgcgtagcac | ggggtcgac | 840 |
| atttgtgatc | ctgaacaggt | gaatggtttt | tttaaggaag | tagcctctca | acatctgaa | 900 |
| attgacgcgg | ttgcggtttt | ttccggtgtt | ttgaaaaccg | gcaagattac | agaaatgagc | 960 |
| cgtgaagaaa | tccgtcaaat | gatagatgtt | aatttgatcg | gttcattaaa | tgtggccttg | 1020 |
| gcttcttttc | cctatttgaa | gaagtcatcc | ggtcatttgt | tgatggttag | ctccagtagt | 1080 |
| tattttcgcg | ggcgtgctaa | ttcagcggtt | tattcatctt | ccaaagcggc | ggtggttaat | 1140 |
| ttaacgcaag | cccttttctga | agaatgggca | gaggataata | ttgcggtttc | ctgtattgct | 1200 |
| ccacggcgtg | ccaatacgcc | gatgcggagg | aaggctttcc | gcatgagaa | tccggcaatt | 1260 |
| tgtcttgacc | ccgatattgt | cagtcagcag | gtgatcgcga | tgttggagca | tccccagaca | 1320 |
| ggtttaatca | aacatattta | t | | | | 1341 |

<210> SEQ ID NO 4
<211> LENGTH: 1281
<212> TYPE: DNA
<213> ORGANISM: Zymomonas mobilis

<400> SEQUENCE: 4

| | | | | | | |
|---|---|---|---|---|---|---|
| aagcaattca | aggtattagg | tggaaagccg | atcatccaat | ataccttgga | ggccttttat | 60 |
| tctcatccgg | cgattgatga | aattattgtg | acctatccgg | ttgaataccg | gaaagagatt | 120 |
| gcaaagataa | ccgcgccttt | ttctaaaaaa | ccgatccatt | tggtggcggg | gggtgcttcc | 180 |
| cgcatggaaa | caaccatggc | ggctttggct | gcggcgggtg | atcgtcatgt | taagatttta | 240 |
| tttcatgatg | cggttcgccc | ttttgtttct | catgatatca | tcagcgatag | tttagttgct | 300 |
| cttgatcggc | atcaggctgt | tgatgttgtt | attccaacgg | cggatactat | cgtttctttg | 360 |
| aatgaggcgc | aggatcattt | actgtctatc | cccaaacgta | gcctgctacg | ccgtggacaa | 420 |
| acgccgcaag | ttctggggg | cgattctctg | gcggctgctt | atcgggcgat | agatcctgaa | 480 |
| attcttgacc | gttttccga | tgattgcggt | gtatttcttt | atcaaaatcc | tgatgctgat | 540 |

```
atcggtgtgg tcaccggtga tgataaaaat atcaaaatta cgacaccgat agatttcttt      600
ttggctgaac aaatcctcta ttcagggcag gcggctagcc gatcagtggt ttccgaggaa      660
aaaagccaga agtccgtggt tcttttggga gcttcatcag gattgggcgc ggcggccgct      720
aaagctatgg aagccaaatg ctggcaagtc tttgccgctt cgcgtagcac gggggtcgac      780
atttgtgatc ctgaacaggt gaatggtttt tttaaggaag tagcctctca acatctgaa       840 attgacgcgg ttgcgttttt tccggtgtt ttgaaaaccg gcaagattac agaaatgagc       900
cgtgaagaaa tccgtcaaat gatagatgtt aatttgatcg gttcattaaa tgtggccttg      960
gcttcttttc cctatttgaa gaagtcatcc ggtcatttgt tgatggttag ctccagtagt     1020
tattttcgcg ggcgtgctaa ttcagcggtt tattcatctt ccaaagcggc ggtggttaat     1080
ttaacgcaag ccctttctga agaatgggca gaggataata ttgcggtttc ctgtattgct     1140
ccacggcgtg ccaatacgcc gatgcggagg aaggctttcc cgcatgagaa tccggcaatt     1200
tgtcttgacc ccgatattgt cagtcagcag gtgatcgcga tgttggagca tccccagaca     1260
ggtttaatca aacatattta t                                               1281

<210> SEQ ID NO 5
<211> LENGTH: 1341
<212> TYPE: DNA
<213> ORGANISM: Zymomonas mobilis

<400> SEQUENCE: 5
atggctattg ccgttatttt gggaggcggg aaaggcaccc gttttggtga tctgctaccc       60
aagcaattca aggtattagg tggaaagccg atcatccaat ataccttgga ggccttttat      120
tctcatccgg caattgatga aattattgtg acctatccgg ttgaataccg gaaagagatt      180
gcaaagatag ccgcgccttt ttctaaaaaa acgatccatt tggtggcggg gggtgcttcc      240
cgcatggaaa caaccatggc ggctttggct gcggcgggtg atcgtcatgt taagatttta      300
tttcatgatg cggttcgccc ttttgtttcc catgatatca tcagcgatag tttgttgct       360 ctcgatcggc atcaggccgt tgatgttgtt attccaacgg ccgatactat cgtttctttg      420
gatgaggcgc aggatcattt actgtctatc cccaaacgta gcctgctacg ccgtggacaa      480
acgccgcaag gtttctgggg cgattctctg gcggctgctt atcggcgat agatcctgaa       540 attcttgacc gttttttccga tgattgcggt gtatttcttt atcaaaatcc tgatactgat      600
atcggtgtgg tcaccggtga tgataaaaat atcaaaatta cgacaccgat agatttcttt      660
ttggctgaac aaatcctcta ttcagggcag gcagctagcc gatcagtggt ttccgaggga      720
aaaagccaga agtccgtggt tcttttggc gcttcatcag gactgggcgc ggcggccgct      780
aaagctatgg agccaaggg ctggcaagtc tttgccgctt cgcgtaccac ggggtcgat       840 atttgtgatc ctgaacaggt gaacggtttt tttaaggaag tagcttctaa acatctgaa       900 attgacgcgg ttgcagtttt ctccggtgtt ttgaaaaccg gcaagattac agaaatgagc       960
cgtgaagaaa tccgtcaaat gatagatgtc aatttgatcg gttcattaaa tgtggccttg     1020 gcttcttttcc cctatttgaa gaagtcatct ggtcatttgt tgatggttag ctccagtagt     1080
tattttcgcg ggcgtgccaa ttcagcggtt tattcatcgt ccaaagcggc ggtggttaat     1140
ttaacgcaag ccctttccga agaatgggca gaggataata ttgcggtttc ctgtattgct     1200
ccacggcgtg ccaatacgcc gatgcggagg aaggctttcc cgcatgaaaa tccggcgatc     1260
tgtcttgacc ctgatattgt cagtcagcag gtgatcgcga tgttggagca tccccagaca     1320
ggtttaatca aacatattta t                                               1341
```

<210> SEQ ID NO 6
<211> LENGTH: 1341
<212> TYPE: DNA
<213> ORGANISM: Zymomonas mobilis

<400> SEQUENCE: 6

```
atggctgttg ccgttatttt gggaggcggg aaaggcaccc gttttggtga tccgctaccc      60
aagcaattca aggtattagg tggaaagccg atcatccaat ataccttgga ggccttttat     120
tctcatccgg cgattgatga aattattgtg acctatccgg ttgaataccg gaaagagatt     180
gcaaagataa ccgcgccttt ttctaaaaaa ccgatccatt tggtggcggg gggtgcttcc     240
cgcatggaaa caaccatggc ggctttggct gcggcgggtg atcgtcatgt aagatttta      300
tttcatgatg cggttcgccc ttttgtttcc catgatatca tcagcgatag tttggttgct     360
cttgatcggc atcaggccgt tgatgttgtt attccaacgg ccgatactat cgtttctttg     420
aatgaggcgc aggatcattt actgtctatc cccaaacgta gtctgctacg ccgtggacaa     480
acgccgcaag gtttctgggg cgattctctg gcggctgctt atcgggcgat agatcctgaa     540
attcttgacc gttttttccga tgattgcggt gtatttctttt atcaaaatcc tgatgctgat     600
atcggtgtgg tcaccggtga tgataaaaat atcaaaatta cgacaccgat agatttctttt    660
ttggctgaac aaatcctcta ttcagggcag gcggctagcc gatcagtggt ttccgaggaa     720
aaaagccaga gtccgtggt tcttttttggc gcttcatcag gattgggcgc ggcggccgct     780
aaagctatgg aagccaaagg ctggcaagtc tttgccgctt cgcgtagcac ggggtcgat     840
atttgtgatc ctgaacaggt gaatgggtttt ttaaggaag tagcctctaa acatctgaa      900
attgacgcgg ttgcagtttt ctccggtgtt ttgaaaaccg gcaagattac agaaatgagc     960
cgtgaagaaa tccgtcaaat gatagatgtc aatttgatcg gttcattaaa tgtggccttg    1020
gcttctttcc cctatttgaa gaagtcatct ggtcatttat tgatggttag ctccagtagt    1080
tattttcgcg ggcgtgctaa ttcagcggtt tattcatctt ccaaagcggc ggtagttaat    1140
ttaacgcaag cgcttttctga gaatgggca gaggataata ttgcggtttc ttgcattgcc    1200
ccaagacgtg ccaatacacc gatgcgaaga aaagctttcc cgcatgaaga tccagcgatt    1260
tgccttgatc ccgatattgt tagccagcaa gtcgttgcga tgttggaaca ttcccagaca    1320
ggtttaatca aacatatttat t                                             1341
```

<210> SEQ ID NO 7
<211> LENGTH: 1302
<212> TYPE: DNA
<213> ORGANISM: Zymomonas mobilis

<400> SEQUENCE: 7

```
atgacgaaca aaatctcgtc ttcagataat cttttccaatg ctgtttcagc aacggatgac     60
aacgcttccc gtacgccaaa tctgacccgt cgcgctctcg ttggtggtgg tgttggactg    120
gccgcagctg gcgccttagc cagtggtctt caggcagcga cgcttcctgc tggtgccagc    180
caggttccga ccacgcctgc aggtcgcccg atgccttacg cgatccgccc gatgccggaa    240
gatcgtcgtt tcggttatgc tatcgtcggt ctgggtaaat atgcccttaa ccagattta     300
ccgggttttg ccggatgcca gcattcccgc atcgaagctt tggtcagcgg taacgctgaa    360
aaagctaaaa tcgttgccgc tgaatatggc gtcgatcccc gtaaaattta tgattacagc    420
aacttcgaca agatcgctaa agatccaaaa atcgacgctg tttacatcat tttgccaaac    480
```

```
tctttgcatg ctgaatttgc tatccgtgct ttcaaagccg gcaagcatgt tatgtgtgaa    540
aagccgatgg caacctctgt tgctgattgt cagcggatga tcgatgcagc caaggctgct    600
aataaaaagc tgatgatcgg ttaccgttgc cactatgatc caatgaaccg tgcagcggta    660
aaattgatcc gtgaaaacca gttgggtaaa ctgggcatgg ttaccaccga caactcagac    720
gttatggatc agaacgatcc tgcacagcag tggcgtctgc gtcgtgaact cgccggtggc    780
ggttctttga tggatatcgg tatttatggc ttgaacggta cccgttactt gctgggtgaa    840
gaaccgatcg aagtccgtgc ttacacctac agcgatccga atgatgaacg tttcgttgaa    900
gtcgaagatc gtattatttg gcagatgcgc ttcagaagcg gtgctctgtc tcatggtgca    960
tcttcttatt cgaccacgac gacttcacgt ttctcggtgc agggcgacaa agctgttctg   1020
ttgatggatc cggctaccgg atattatcag aatttgattt ctgtccagac cccaggccat   1080
gctaaccagt cgatgatgcc acagttcatc atgccagcga caaccagtt ctctgcacag    1140 ttggatcatc tggctgaagc cgtcatcaat aacaaaccag ttcgtagccc gggtgaagaa   1200
ggtatgcagg atgtgcgcct gattcaggcc atttatgaag cagctcgtac cggtcgcccc   1260
gtcaacacgg attggggtta tgtccgtcag ggtggttatt ga                      1302
```

<210> SEQ ID NO 8
<211> LENGTH: 157
<212> TYPE: PRT
<213> ORGANISM: Zymomonas mobilis

<400> SEQUENCE: 8

```
Met Thr Ser Ala Val Pro Ser Asn Thr Lys Lys Leu Val Ile Ala
1               5                   10                  15

Ser Asp His Ala Ala Phe Glu Leu Lys Ser Thr Leu Ile Thr Trp Leu
            20                  25                  30

Lys Glu Leu Gly His Glu Val Glu Asp Leu Gly Pro His Glu Asn His
        35                  40                  45

Ser Val Asp Tyr Pro Asp Tyr Gly Tyr Lys Leu Ala Val Ala Ile Ala
    50                  55                  60

Glu Lys Thr Ala Asp Phe Gly Ile Ala Leu Cys Gly Ser Gly Ile Gly
65                  70                  75                  80

Ile Ser Ile Ala Val Asn Arg His Pro Ala Ala Arg Cys Ala Leu Ile
                85                  90                  95

Thr Asp Asn Leu Thr Ala Arg Leu Ala Arg Glu His Asn Asn Ala Asn
            100                 105                 110

Val Ile Ala Met Gly Ala Arg Leu Ile Gly Ile Glu Thr Ala Lys Asp
        115                 120                 125

Cys Ile Ser Ala Phe Leu Ala Thr Pro Phe Gly Gly Glu Arg His Val
    130                 135                 140

Arg Arg Ile Asp Lys Leu Ser Asn Pro Gln Phe Asn Ile
145                 150                 155
```

<210> SEQ ID NO 9
<211> LENGTH: 219
<212> TYPE: PRT
<213> ORGANISM: Escherichia coli

<400> SEQUENCE: 9

```
Met Thr Gln Asp Glu Leu Lys Lys Ala Val Gly Trp Ala Ala Leu Gln
1               5                   10                  15

Tyr Val Gln Pro Gly Thr Ile Val Gly Val Gly Thr Gly Ser Thr Ala
            20                  25                  30
```

Ala His Phe Ile Asp Ala Leu Gly Thr Met Lys Gly Gln Ile Glu Gly
            35                  40                  45

Ala Val Ser Ser Ser Asp Ala Ser Thr Glu Lys Leu Lys Ser Leu Gly
        50                  55                  60

Ile His Val Phe Asp Leu Asn Glu Val Asp Ser Leu Gly Ile Tyr Val
65                  70                  75                  80

Asp Gly Ala Asp Glu Ile Asn Gly His Met Gln Met Ile Lys Gly Gly
                85                  90                  95

Gly Ala Ala Leu Thr Arg Glu Lys Ile Ile Ala Ser Val Ala Glu Lys
            100                 105                 110

Phe Ile Cys Ile Ala Asp Ala Ser Lys Gln Val Asp Ile Leu Gly Lys
        115                 120                 125

Phe Pro Leu Pro Val Glu Val Ile Pro Met Ala Arg Ser Ala Val Ala
    130                 135                 140

Arg Gln Leu Val Lys Leu Gly Gly Arg Pro Glu Tyr Arg Gln Gly Val
145                 150                 155                 160

Val Thr Asp Asn Gly Asn Val Ile Leu Asp Val His Gly Met Glu Ile
                165                 170                 175

Leu Asp Pro Ile Ala Met Glu Asn Ala Ile Asn Ala Ile Pro Gly Val
            180                 185                 190

Val Thr Val Gly Leu Phe Ala Asn Arg Gly Ala Asp Val Ala Leu Ile
        195                 200                 205

Gly Thr Pro Asp Gly Val Lys Thr Ile Val Lys
    210                 215

<210> SEQ ID NO 10
<211> LENGTH: 657
<212> TYPE: DNA
<213> ORGANISM: Escherichia coli

<400> SEQUENCE: 10
atgacgcagg atgaattgaa aaaagcagta ggatgggcgg cacttcagta tgttcagccc      60
ggcaccattg ttggtgtagg tacaggttcc accgccgcac actttattga cgcgctcggt     120
acaatgaaag ccagattga aggggccgtt tccagttcag atgcttccac tgaaaaactg     180
aaaagcctcg gcattcacgt ttttgatctc aacgaagtcg acagccttgg catctacgtt     240
gatggcgcag atgaaatcaa cggccacatg caaatgatca aggcggcgg cgcggcgctg     300 acccgtgaaa aaatcattgc ttcggttgca gaaaaattta tctgtattgc agacgcttcc     360
aagcaggttg atattctggg taaattcccg ctgccagtag aagttatccc gatggcacgt     420
agtgcagtgg cgcgtcagct ggtgaaactg gcggtcgtc ggaataccg tcagggcgtg     480 gtgaccgata atggcaacgt gatcctcgac gtccacggca tggaaatcct tgacccgata     540
gcgatggaaa acgccataaa tgcgattcct ggcgtggtga ctgttggctt gtttgctaac     600
cgtggcgcgg acgttgcgct gattggcaca cctgacggtg tcaaaaccat tgtgaaa       657

<210> SEQ ID NO 11
<211> LENGTH: 1023
<212> TYPE: DNA
<213> ORGANISM: Zymomonas mobilis

<400> SEQUENCE: 11
atgaacactt ctacgcaaaa acccgctcat ttcgacaaga tttcgatcaa agggattgat      60
aaatccgcaa cccgtgtagc gttaggcaca tgggctattg gtggctggat gtggggcggc     120

```
actgatgacg atgcctccat taaaaccatt catcgggcga ttgatcttgg tatcaatatc    180
atcgacaccg ctccggctta tggccgtggc catgctgaag aagtcgttgg taaagccatc    240
aaaggtcaac gcgataattt gattattgcg accaaagtcg gccttgattg gactttaacc    300
cccgaccaat cgatgcgccg taacagttca gccagccgta tcaaaaaaga aatcgaagat    360
tctctgcgcc gccttggcac tgattatatc gacctttatc aggtgcattg gccggatccg    420
ctggttccga ttgaagaaac cgcaacaata ttggaagccc tcagaaaaga aggcaaaatc    480
cgttctatcg gcgtttccaa ttattccgtt cagcagatgg acgagttcaa gaaatatgcc    540
gagctggccg tttcgcagtc gccttataat ctgtttgaac gcgaaataga caaagacatc    600
ctgccctatg ccaagaaaaa cgatctggtc gttttaggct atggtgcgct ttgccgtggt    660
ttactttctg gcagaatgac ggcggatcgt gcctttacag gcgatgattt acggaaaaca    720
gacccgaaat tccagaaacc gcgctttgaa cattatctgg ccgcggttga agaactgaag    780
aaactcgcca agagcattaa caataaatcg gtgttggctt tggctatccg ctggatgttg    840
gagcaagggc ccactttagc actttggggc gctcgcaagc cggaacagat cgacggtatt    900
gatgaagttt ttggctggca gatatcggat gaagatctga aacagattga tgctattctg    960
gccaagaata tccccaatcc tatcggtgca gaatttatgg caccccccgcc acgcgataaa   1020
taa                                                                 1023

<210> SEQ ID NO 12
<211> LENGTH: 340
<212> TYPE: PRT
<213> ORGANISM: Zymomonas mobilis

<400> SEQUENCE: 12

Met Asn Thr Ser Thr Gln Lys Pro Ala His Phe Asp Lys Ile Ser Ile
1               5                   10                  15

Lys Gly Ile Asp Lys Ser Ala Thr Arg Val Ala Leu Gly Thr Trp Ala
            20                  25                  30

Ile Gly Gly Trp Met Trp Gly Gly Thr Asp Asp Ala Ser Ile Lys
        35                  40                  45

Thr Ile His Arg Ala Ile Asp Leu Gly Ile Asn Ile Ile Asp Thr Ala
    50                  55                  60

Pro Ala Tyr Gly Arg Gly His Ala Glu Glu Val Val Gly Lys Ala Ile
65                  70                  75                  80

Lys Gly Gln Arg Asp Asn Leu Ile Ile Ala Thr Lys Val Gly Leu Asp
                85                  90                  95

Trp Thr Leu Thr Pro Asp Gln Ser Met Arg Arg Asn Ser Ser Ala Ser
            100                 105                 110

Arg Ile Lys Lys Glu Ile Glu Asp Ser Leu Arg Arg Leu Gly Thr Asp
        115                 120                 125

Tyr Ile Asp Leu Tyr Gln Val His Trp Pro Asp Pro Leu Val Pro Ile
    130                 135                 140

Glu Glu Thr Ala Thr Ile Leu Glu Ala Leu Arg Lys Glu Gly Lys Ile
145                 150                 155                 160

Arg Ser Ile Gly Val Ser Asn Tyr Ser Val Gln Gln Met Asp Glu Phe
                165                 170                 175

Lys Lys Tyr Ala Glu Leu Ala Val Ser Gln Ser Pro Tyr Asn Leu Phe
            180                 185                 190

Glu Arg Glu Ile Asp Lys Asp Ile Leu Pro Tyr Ala Lys Lys Asn Asp
        195                 200                 205
```

```
Leu Val Val Gly Tyr Gly Ala Leu Cys Arg Gly Leu Leu Ser Gly
    210             215                 220
Arg Met Thr Ala Asp Arg Ala Phe Thr Gly Asp Asp Leu Arg Lys Thr
225             230                 235                 240
Asp Pro Lys Phe Gln Lys Pro Arg Phe Glu His Tyr Leu Ala Ala Val
            245                 250                 255
Glu Glu Leu Lys Lys Leu Ala Lys Glu His Tyr Asn Lys Ser Val Leu
        260                 265                 270
Ala Leu Ala Ile Arg Trp Met Leu Glu Gln Gly Pro Thr Leu Ala Leu
    275                 280                 285
Trp Gly Ala Arg Lys Pro Glu Gln Ile Asp Gly Ile Asp Glu Val Phe
290             295                 300
Gly Trp Gln Ile Ser Asp Glu Asp Leu Lys Gln Ile Asp Ala Ile Leu
305             310                 315                 320
Ala Lys Asn Ile Pro Asn Pro Ile Gly Ala Glu Phe Met Ala Pro Pro
                325                 330                 335
Pro Arg Asp Lys
            340

<210> SEQ ID NO 13
<211> LENGTH: 2247
<212> TYPE: DNA
<213> ORGANISM: Zymomonas mobilis

<400> SEQUENCE: 13
atgttcgata ttaaacgcca ggaaatcgat tggggcggaa aaaaactgac actggaaacc    60
ggacaggttg cccgtcaggc agatggcgcc gtcattgcga ccttaggtga acggtcgta   120 ttatgcgcgg taacggcagc aaaaacggta aaagaaggtc aggatttctt tcctttgacc   180
gtccattatc aggaaaaata ttcagcagca ggccgtattc ccgtggcctt tttcaagcgt   240
gaacgtggcg caaccgaacg ggaaacgctg atttcacggt taatcgaccg tccaatccgt   300
cctctgtttc cggaaggttt ctataacgaa accttggtca ttgcgcaggt catgtcctat   360
gacggcgaga tgaaccgga tatcttggcg atgatcgctg cttctgcggc tcttgctctt   420
tccggtgtgc ctttcttggg ccccatcggt gctgcccgtg tgggttatca agatggcgag   480
ttcattctta acccgacctt ggaacagctt gaaaaaagtg atcttgatct ggttgtcggg   540
gctacccgtg atgccgtgat gatggttgaa tcggaagcga atgagcttcc cgaagaagtc   600
atgctcaatg ccgtttcttt tgcgcatgaa tctttacagc cggttatcaa agctatcatc   660
aatctggcag aacaggccgc taagagcct tgggaactgg tcagctatga tgacagcgca   720
ttggctgcca agtcgaaga actctgctac gacaatttcg ataaggccta tcgtctgact   780
cgcaaggctg aacgtgttga cgccttgagc aaggccaaag cggttcttga cgaagccttc   840
ccagaagctg atccgacaga aaagctgcgc atccagaagc ttgcgaagaa gctggaagca   900
aaaatcgtcc gcaccgccat tctgaaagaa ggccggagaa ttgacggacg cgatctgaaa   960
acagttcgcc cgatccgctc tcaggttgga ttcttgcccc gcacgcatgg ttctgccctg  1020
tttacgcgtg tgaaacaca ggctttggtt tcaaccaccc ttggaacggc ggatgctgaa  1080
cagatgatcg acggtttaac cggccttcat tatgaacgct tcatgctgca ttacaacttc  1140
ccccatattt cggtcggtga agttggtcgt tttggtgctc cgggtcgtcg tgaaatcggc  1200
catggtaaac tggcatggcg tgcgcttcat ccggttttgc cgagcaaggc tgatttcccg  1260
tataccatcc gtgttttgtc ggatatcacc gaatctaatg gttcctcttc catggcaacc  1320
```

```
gtttgcggtg gctgccttgc attgatggat gccggtgttc ccttaacgcg tccggtttcc    1380
ggtatcgcca tgggtcttat tctggaaaaa gacggcttcg ctattttgtc cgatatcatg    1440
ggtgatgaag atcacttggg tgatatggac tttaaggtcg ccggtaccga aaaggtatc    1500 accagcctcc agatggacat caaggttgct ggcattaccg aagaaatcat gcagaaagct    1560
ttggaacagg ctaaaggtgg ccgtgctcat atcttgggtg aaatgtccaa agcgctgggt    1620
gaagtccgct ccgaaatttc taatttggca ccgcgcattg aaacaatgag cgtaccaaaa    1680
gacaaaatcc gtgatgttat cggaacgggc ggaaaagtta tccgtgaaat cgtggcgacc    1740
acaggtgcca aggtcgatat cgaagatgac ggcacggttc gtctgtcttc ttctgatccg    1800
gccaatattg aagcagcccg tgaatggatc aatggtattg ttgaagaacc ggaagtaggc    1860
aaaatctata acggtaaagt cgtcaatatc gttgatttcg gtgccttcgt aaacttcatg    1920
ggtggccgtg acggcttggt acatgtttcg gaaatcaaga cgaacgtgt caacaaggtc    1980 agcgatgtcc tgtccgaagg tcaggaagtc aaagtcaagg ttcttgaaat tgacaaccgt    2040
ggcaaggttc gcctgtctat gcgtgttgtc gatcaggaaa ccggcgcaga gctggatgat    2100
aaccgtccgc cacgtgagaa cgcagaacgt cgcggtggtg agcgtcctcg tcgtgatcgg    2160
ggccctcgtc gggaatctgg cgatcgtccg gcaagacgtg atatggaacc ggaatttgct    2220
ccggcattcc tgcgcaaaga tagctaa                                        2247
```

<210> SEQ ID NO 14
<211> LENGTH: 748
<212> TYPE: PRT
<213> ORGANISM: Zymomonas mobilis

<400> SEQUENCE: 14

Met Phe Asp Ile Lys Arg Gln Glu Ile Asp Trp Gly Gly Lys Lys Leu
1               5                   10                  15

Thr Leu Glu Thr Gly Gln Val Ala Arg Gln Ala Asp Gly Ala Val Ile
            20                  25                  30

Ala Thr Leu Gly Glu Thr Val Leu Cys Ala Val Thr Ala Ala Lys
        35                  40                  45

Thr Val Lys Glu Gly Gln Asp Phe Phe Pro Leu Thr Val His Tyr Gln
    50                  55                  60

Glu Lys Tyr Ser Ala Ala Gly Arg Ile Pro Gly Gly Phe Phe Lys Arg
65                  70                  75                  80

Glu Arg Gly Ala Thr Glu Arg Glu Thr Leu Ile Ser Arg Leu Ile Asp
                85                  90                  95

Arg Pro Ile Arg Pro Leu Phe Pro Glu Gly Phe Tyr Asn Glu Thr Leu
            100                 105                 110

Val Ile Ala Gln Val Met Ser Tyr Asp Gly Glu Asn Glu Pro Asp Ile
        115                 120                 125

Leu Ala Met Ile Ala Ala Ser Ala Ala Leu Ala Leu Ser Gly Val Pro
    130                 135                 140

Phe Leu Gly Pro Ile Gly Ala Ala Arg Val Gly Tyr Gln Asp Gly Glu
145                 150                 155                 160

Phe Ile Leu Asn Pro Thr Leu Glu Gln Leu Glu Lys Ser Asp Leu Asp
                165                 170                 175

Leu Val Val Gly Ala Thr Arg Asp Ala Val Met Met Val Glu Ser Glu
            180                 185                 190

Ala Asn Glu Leu Pro Glu Glu Val Met Leu Asn Ala Val Ser Phe Ala
        195                 200                 205

His Glu Ser Leu Gln Pro Val Ile Lys Ala Ile Ile Asn Leu Ala Glu
    210                 215                 220

Gln Ala Ala Lys Glu Pro Trp Glu Leu Val Ser Tyr Asp Asp Ser Ala
225                 230                 235                 240

Leu Ala Ala Lys Val Glu Glu Leu Cys Tyr Asp Asn Phe Asp Lys Ala
                245                 250                 255

Tyr Arg Leu Thr Arg Lys Ala Glu Arg Val Asp Ala Leu Ser Lys Ala
            260                 265                 270

Lys Ala Val Leu Asp Glu Ala Phe Pro Glu Ala Asp Pro Thr Glu Lys
        275                 280                 285

Leu Arg Ile Gln Lys Leu Ala Lys Lys Leu Glu Ala Lys Ile Val Arg
    290                 295                 300

Thr Ala Ile Leu Lys Glu Gly Arg Arg Ile Asp Gly Arg Asp Leu Lys
305                 310                 315                 320

Thr Val Arg Pro Ile Arg Ser Gln Val Gly Phe Leu Pro Arg Thr His
                325                 330                 335

Gly Ser Ala Leu Phe Thr Arg Gly Glu Thr Gln Ala Leu Val Ser Thr
            340                 345                 350

Thr Leu Gly Thr Ala Asp Ala Glu Gln Met Ile Asp Gly Leu Thr Gly
        355                 360                 365

Leu His Tyr Glu Arg Phe Met Leu His Tyr Asn Phe Pro Pro Tyr Ser
    370                 375                 380

Val Gly Glu Val Gly Arg Phe Gly Ala Pro Gly Arg Arg Glu Ile Gly
385                 390                 395                 400

His Gly Lys Leu Ala Trp Arg Ala Leu His Pro Val Leu Pro Ser Lys
                405                 410                 415

Ala Asp Phe Pro Tyr Thr Ile Arg Val Leu Ser Asp Ile Thr Glu Ser
            420                 425                 430

Asn Gly Ser Ser Ser Met Ala Thr Val Cys Gly Gly Cys Leu Ala Leu
        435                 440                 445

Met Asp Ala Gly Val Pro Leu Thr Arg Pro Val Ser Gly Ile Ala Met
    450                 455                 460

Gly Leu Ile Leu Glu Lys Asp Gly Phe Ala Ile Leu Ser Asp Ile Met
465                 470                 475                 480

Gly Asp Glu Asp His Leu Gly Asp Met Asp Phe Lys Val Ala Gly Thr
                485                 490                 495

Glu Lys Gly Ile Thr Ser Leu Gln Met Asp Ile Lys Val Ala Gly Ile
            500                 505                 510

Thr Glu Glu Ile Met Gln Lys Ala Leu Glu Gln Ala Lys Gly Gly Arg
        515                 520                 525

Ala His Ile Leu Gly Glu Met Ser Lys Ala Leu Gly Glu Val Arg Ser
    530                 535                 540

Glu Ile Ser Asn Leu Ala Pro Arg Ile Glu Thr Met Ser Val Pro Lys
545                 550                 555                 560

Asp Lys Ile Arg Asp Val Ile Gly Thr Gly Gly Lys Val Ile Arg Glu
                565                 570                 575

Ile Val Ala Thr Thr Gly Ala Lys Val Asp Ile Glu Asp Asp Gly Thr
            580                 585                 590

Val Arg Leu Ser Ser Ser Asp Pro Ala Asn Ile Glu Ala Ala Arg Glu
        595                 600                 605

Trp Ile Asn Gly Ile Val Glu Glu Pro Glu Val Gly Lys Ile Tyr Asn
    610                 615                 620

Gly Lys Val Val Asn Ile Val Asp Phe Gly Ala Phe Val Asn Phe Met

```
                625                 630                 635                 640
Gly Gly Arg Asp Gly Leu Val His Val Ser Glu Ile Lys Asn Glu Arg
                    645                 650                 655

Val Asn Lys Val Ser Asp Val Leu Ser Glu Gly Gln Glu Val Lys Val
                660                 665                 670

Lys Val Leu Glu Ile Asp Asn Arg Gly Lys Val Arg Leu Ser Met Arg
            675                 680                 685

Val Val Asp Gln Glu Thr Gly Ala Glu Leu Asp Asp Asn Arg Pro Pro
        690                 695                 700

Arg Glu Asn Ala Glu Arg Arg Gly Gly Glu Arg Pro Arg Arg Asp Arg
705                 710                 715                 720

Gly Pro Arg Arg Glu Ser Gly Asp Arg Pro Ala Arg Arg Asp Met Glu
                725                 730                 735

Pro Glu Phe Ala Pro Ala Phe Leu Arg Lys Asp Ser
            740                 745
```

<210> SEQ ID NO 15
<211> LENGTH: 2247
<212> TYPE: DNA
<213> ORGANISM: Zymomonas mobilis

<400> SEQUENCE: 15

```
atgttcgata ttaaacgcca ggaaatcgat tggggcggaa aaaaactgac actggaaacc      60
ggacaggttg cccgtcaggc agatggcgcc gtcattgcga ccttaggtga acggtcgta     120
ttatgcgcgg taacgcagc aaaaacggta aagaaggtc aggatttctt tcctttgacc      180
gtccattatc aggaaaaata ttcagcagca ggccgtattc ccggtggctt tttcaagcgt    240
gaacgtggcg caaccgaacg ggaaacgctg atttcacggt taatcgaccg tccaatccgt   300
cctctgtttc cggaaggttt ctataacgaa accttggtca ttgcgcaggt catgtcctat   360
gacggcgaga tgaaccgga tatcttggcg atgatcgccg cttctgcggc ccttgctctt    420
tccggtgtgc ctttccttgg tcctatcggt gctgcccgtg tgggttatca agatggcgag   480
ttcattctta acccgacctt ggaacagctt gaaaaagtg atcttgatct ggttgtcggg    540
gctacccgtg atgccgtgat gatggttgaa tcggaagcga atgagcttcc cgaagaagtc    600
atgctcaatg ctgtttcttt tgcgcatgaa tctttacagc cggttatcaa agctatcatc   660
aatctggcag aacaggccgc taagagcct tgggaactgg tcagctatga tgacagcgca    720
ttggctgcca agtcgaaga actctgctac gacaatttcg ataaggccta tcgtctgact    780
cgcaaggctg aacgtgttga cgccttgagc aaggccaaag cggttcttga cgaagccttc   840
ccagaagctg atccgacaga aaagctgcgc atccagaagc ttgcgaagaa gctggaagca   900
aaaattgtcc gcaccgccat tctgaaagaa ggccggagaa ttgacggacg cgatctgaaa  960
acagttcgcc cgatccgctc tcaggttgga ttcttgcccc gcacgcatgg ttctgccctg 1020
tttacgcgtg gtgaaacaca ggctttggtt caaccaccc ttggaacggc ggatgctgaa  1080
cagatgatcg acggtttaac cggccttcat tatgaacgct tcatgctgca ttataacttc 1140
cctccttatt cggtcggtga agttggtcgt tttggtgctc cgggtcgtcg tgaaatcggc 1200
catggtaaac tggcatggcg tgcgcttcat ccggttttgc cgagcaaggc tgatttcccg 1260
tataccatcc gcgttttgtc ggatatcacc gaatctaatg gttcctcttc tatggcaacc 1320
gtttgcggtg gctgccttgc attgatggat gccggtgttc ccttaacgcg tccggtttcc 1380
ggtatcgcca tgggtcttat tctagaaaaa gacggcttcg ctattttgtc cgatatcatg 1440
```

-continued

```
ggtgatgaag atcacttggg tgatatggac tttaaggtcg ccggtaccga aaaaggtatc    1500
accagcctcc agatggacat caaggttgct ggcattaccg aagaaatcat gcagaaagct    1560
ttggaacagg ctaaaggtgg ccgtgctcat atcttgggtg aaatgtccaa agcgctgggt    1620
gaagtccgct ccgaaatttc taatttggca ccgcgcattg aaacgatgag cgtaccaaaa    1680
gacaaaatcc gtgatgttat cggaacgggc ggaaaagtta ccgtgaaat cgtggcaacc     1740 acaggtgcca aggtcgatat cgaagatgac ggaacggttc gtctgtcttc ttccgatcct    1800
gccaatattg aagcagcccg tgaatggatc aatggtattg ttgaagaacc ggaagtaggc    1860
aaaatctata acggtaaagt cgtcaatatc gttgatttcg gtgccttcgt aaacttcatg    1920
ggcggccgtg acggcttggt acatgtttcg gaaatcaaga cgaacgtgt caacaaggtc     1980 agcgatgtcc tgtctgaagg tcaggaagtc aaagtcaagg ttcttgaaat tgacaaccgt    2040
ggcaaggttc gcctgtctat gcgtgttgtc gatcaggaaa ccggcgcaga gctggatgat    2100
aaccgtccgc cacgtgagaa cgcagaacgt cgcggtggtg agcgtcctcg tcgtgatcgg    2160
ggccctcgtc gggaatctgg cgatcgtccg gcaagacgtg acatggaacc ggaatttgct    2220
ccggcattcc tgcgcaaaga tagctaa                                        2247
```

<210> SEQ ID NO 16
<211> LENGTH: 748
<212> TYPE: PRT
<213> ORGANISM: Zymomonas mobilis

<400> SEQUENCE: 16

```
Met Phe Asp Ile Lys Arg Gln Glu Ile Asp Trp Gly Gly Lys Lys Leu
1               5                   10                  15

Thr Leu Glu Thr Gly Gln Val Ala Arg Gln Ala Asp Gly Ala Val Ile
            20                  25                  30

Ala Thr Leu Gly Glu Thr Val Leu Cys Ala Val Thr Ala Ala Lys
        35                  40                  45

Thr Val Lys Glu Gly Gln Asp Phe Phe Pro Leu Thr Val His Tyr Gln
    50                  55                  60

Glu Lys Tyr Ser Ala Ala Gly Arg Ile Pro Gly Gly Phe Phe Lys Arg
65                  70                  75                  80

Glu Arg Gly Ala Thr Glu Arg Glu Thr Leu Ile Ser Arg Leu Ile Asp
                85                  90                  95

Arg Pro Ile Arg Pro Leu Phe Pro Glu Gly Phe Tyr Asn Glu Thr Leu
            100                 105                 110

Val Ile Ala Gln Val Met Ser Tyr Asp Gly Glu Asn Glu Pro Asp Ile
        115                 120                 125

Leu Ala Met Ile Ala Ala Ser Ala Ala Leu Ala Leu Ser Gly Val Pro
    130                 135                 140

Phe Leu Gly Pro Ile Gly Ala Ala Arg Val Gly Tyr Gln Asp Gly Glu
145                 150                 155                 160

Phe Ile Leu Asn Pro Thr Leu Glu Gln Leu Glu Lys Ser Asp Leu Asp
                165                 170                 175

Leu Val Val Gly Ala Thr Arg Asp Ala Val Met Met Val Glu Ser Glu
            180                 185                 190

Ala Asn Glu Leu Pro Glu Glu Val Met Leu Asn Ala Val Ser Phe Ala
        195                 200                 205

His Glu Ser Leu Gln Pro Val Ile Lys Ala Ile Ile Asn Leu Ala Glu
    210                 215                 220

Gln Ala Ala Lys Glu Pro Trp Glu Leu Val Ser Tyr Asp Asp Ser Ala
```

```
            225                 230                 235                 240
Leu Ala Ala Lys Val Glu Glu Leu Cys Tyr Asp Asn Phe Asp Lys Ala
                    245                 250                 255

Tyr Arg Leu Thr Arg Lys Ala Glu Arg Val Asp Ala Leu Ser Lys Ala
                260                 265                 270

Lys Ala Val Leu Asp Glu Ala Phe Pro Glu Ala Asp Pro Thr Glu Lys
            275                 280                 285

Leu Arg Ile Gln Lys Leu Ala Lys Lys Leu Glu Ala Lys Ile Val Arg
        290                 295                 300

Thr Ala Ile Leu Lys Glu Gly Arg Arg Ile Asp Gly Arg Asp Leu Lys
305                 310                 315                 320

Thr Val Arg Pro Ile Arg Ser Gln Val Gly Phe Leu Pro Arg Thr His
                    325                 330                 335

Gly Ser Ala Leu Phe Thr Arg Gly Glu Thr Gln Ala Leu Val Ser Thr
                340                 345                 350

Thr Leu Gly Thr Ala Asp Ala Glu Gln Met Ile Asp Gly Leu Thr Gly
            355                 360                 365

Leu His Tyr Glu Arg Phe Met Leu His Tyr Asn Phe Pro Pro Tyr Ser
        370                 375                 380

Val Gly Glu Val Gly Arg Phe Gly Ala Pro Gly Arg Arg Glu Ile Gly
385                 390                 395                 400

His Gly Lys Leu Ala Trp Arg Ala Leu His Pro Val Leu Pro Ser Lys
                    405                 410                 415

Ala Asp Phe Pro Tyr Thr Ile Arg Val Leu Ser Asp Ile Thr Glu Ser
                420                 425                 430

Asn Gly Ser Ser Ser Met Ala Thr Val Cys Gly Gly Cys Leu Ala Leu
            435                 440                 445

Met Asp Ala Gly Val Pro Leu Thr Arg Pro Val Ser Gly Ile Ala Met
        450                 455                 460

Gly Leu Ile Leu Glu Lys Asp Gly Phe Ala Ile Leu Ser Asp Ile Met
465                 470                 475                 480

Gly Asp Glu Asp His Leu Gly Asp Met Asp Phe Lys Val Ala Gly Thr
                    485                 490                 495

Glu Lys Gly Ile Thr Ser Leu Gln Met Asp Ile Lys Val Ala Gly Ile
                500                 505                 510

Thr Glu Glu Ile Met Gln Lys Ala Leu Glu Gln Ala Lys Gly Gly Arg
            515                 520                 525

Ala His Ile Leu Gly Glu Met Ser Lys Ala Leu Gly Glu Val Arg Ser
        530                 535                 540

Glu Ile Ser Asn Leu Ala Pro Arg Ile Glu Thr Met Ser Val Pro Lys
545                 550                 555                 560

Asp Lys Ile Arg Asp Val Ile Gly Thr Gly Gly Lys Val Ile Arg Glu
                    565                 570                 575

Ile Val Ala Thr Thr Gly Ala Lys Val Asp Ile Glu Asp Asp Gly Thr
                580                 585                 590

Val Arg Leu Ser Ser Ser Asp Pro Ala Asn Ile Glu Ala Ala Arg Glu
            595                 600                 605

Trp Ile Asn Gly Ile Val Glu Glu Pro Glu Val Gly Lys Ile Tyr Asn
        610                 615                 620

Gly Lys Val Val Asn Ile Val Asp Phe Gly Ala Phe Val Asn Phe Met
625                 630                 635                 640

Gly Gly Arg Asp Gly Leu Val His Val Ser Glu Ile Lys Asn Glu Arg
                    645                 650                 655
```

```
Val Asn Lys Val Ser Asp Val Leu Ser Glu Gly Gln Glu Val Lys Val
            660                 665                 670

Lys Val Leu Glu Ile Asp Asn Arg Gly Lys Val Arg Leu Ser Met Arg
        675                 680                 685

Val Val Asp Gln Glu Thr Gly Ala Glu Leu Asp Asp Asn Arg Pro Pro
            690                 695                 700

Arg Glu Asn Ala Glu Arg Arg Gly Gly Glu Arg Pro Arg Arg Asp Arg
705                 710                 715                 720

Gly Pro Arg Arg Glu Ser Gly Asp Arg Pro Ala Arg Arg Asp Met Glu
                725                 730                 735

Pro Glu Phe Ala Pro Ala Phe Leu Arg Lys Asp Ser
            740                 745

<210> SEQ ID NO 17
<211> LENGTH: 2247
<212> TYPE: DNA
<213> ORGANISM: Zymomonas mobilis

<400> SEQUENCE: 17
atgttcgata ttaaacgcca ggaaatcgat tggggcggga aaaaactgac actggaaacc       60
ggacaggttg cccgtcaggc agatggcgcc gtcattgcga ccttaggtga acggtcgta      120
ttatgcgcgg taacgcagc aaaaacggta aagaaggtc aggatttctt cctttgacc       180
gtccattatc aggaaaaata ttcagcagca ggccgtattc ccggtggctt tttcaagcgt    240
gaacgtggcg caaccgaacg ggaaacgctg atttcacggt taatcgaccg tccaatccgt    300
cctctgtttc cggaaggttt ctataacgaa accttggtca ttgcgcaggt catgtcctat    360
gacggcgaga tgaaccgga tatcttggcg atgatcgccg cttctgcggc ccttgctctt    420
tccggtgtgc ctttccttgg tcccatcggt gctgcccgtg tgggttatca agatggcgag    480
ttcattctta acccgacctt ggaacagctt gaaaaagtg atcttgatct ggttgtcggg    540
gctacccgtg atgccgtgat gatggttgaa tcggaagcga atgagcttcc cgaagaagtc    600
atgctcaatg ccgtttcttt tgcgcatgaa tctttacagc cggttatcaa agctatcatc    660
aatctggcag aacaggccgc taaagagcct tgggaactgg tcagctatga tgacagcgca    720
ttggctgcca aagtcgaaga actctgctac gacaatttcg ataaggccta tcgtctgact    780
cgtaaggctg agcgtgttga agccttgagc aaggccaaag cggttcttga cgaagccttc    840
ccagaagctg atccgacaga aaagctgcgt atccagaagc tcgcgaagaa gctggaagca    900
aaaatcgtcc gcaccgccat tctgaaagaa ggccggagaa ttgacggacg cgatctgaaa    960
acagttcgcc cgatccgctc tcaggttgga ttcttgcccc gcacgcatgg ttctgctctg   1020
tttacgcgcg gtgaaacaca ggctttggtt caaccaccc ttggaacggc ggatgctgaa    1080
cagatgatcg acggtttaac cggccttcat tatgaacgct tcatgctgca ttataacttc   1140
cctccttatt cggtcggtga agttggtcgt ttggggctc cgggtcgtcg tgaaatcggc    1200
catggtaaac tggcatggcg tgcgcttcat ccggttttgc cgagcaaggc tgatttcccg   1260
tataccatcc gcgttttgtc ggatatcacc gaatctaatg ttcctcttc catggcaacc    1320
gtttgcggtg ctgccttgc cttgatggat gccgtgttc ccttaacgcg tccgttttcc     1380
ggtatcgcca tgggtcttat tctggaaaaa gacggcttcg ctattttgtc ggatatcatg   1440
ggtgatgaag atcacttggg tgatatggac tttaaggtcg ccggtaccga aaaaggtatc   1500
accagcctcc agatggacat caaggttgct ggcattaccg aagaaatcat gcagaaagct   1560
```

-continued

```
ttggaacagg ctaaaggtgg ccgtgctcat atcttgggtg aaatgtccaa agcgctgggt    1620
gaagtccgct ccgaaatttc taatttggca ccgcgcattg aaacaatgag cgtaccaaaa    1680
gacaaaatcc gtgatgttat cggaacgggc ggaaaagtta tccgtgaaat cgtggcgacc    1740
acaggtgcca aggtcgatat cgaagatgac ggcacggttc gtctgtcttc ttccgatccg    1800
gccaatattg aagcagcccg tgaatggatc aatggtattg ttgaagaacc ggaagtaggc    1860
aaaatctata acgtaaagt cgtcaatatc gttgatttcg gtgccttcgt aaacttcatg    1920
ggtggccgtg acggcttggt acatgtttcg gaaatcaaga acgaacgtgt caacaaggtc    1980
agcgatgtcc tgtctgaagg tcaggaagtc aaagtcaagg ttcttgaaat tgacaaccgt    2040
ggcaaggttc gcctgtctat gcgtgttgtc gatcaggaaa ccggcgcaga gctggatgat    2100
aaccgtccgc cacgtgagaa cgcagaacgt cgcggtggtg agcgtcctcg tcgtgatcgg    2160
ggccctcgtc gggaatctgg cgatcgtccg gcaagacgtg acatggaacc ggaatttgct    2220
ccggcattcc tgcgcaaaga tagctaa                                        2247
```

<210> SEQ ID NO 18
<211> LENGTH: 748
<212> TYPE: PRT
<213> ORGANISM: Zymomonas mobilis

<400> SEQUENCE: 18

```
Met Phe Asp Ile Lys Arg Gln Glu Ile Asp Trp Gly Gly Lys Lys Leu
1               5                   10                  15

Thr Leu Glu Thr Gly Gln Val Ala Arg Gln Ala Asp Gly Ala Val Ile
            20                  25                  30

Ala Thr Leu Gly Glu Thr Val Leu Cys Ala Val Thr Ala Ala Lys
        35                  40                  45

Thr Val Lys Glu Gly Gln Asp Phe Phe Pro Leu Thr Val His Tyr Gln
    50                  55                  60

Glu Lys Tyr Ser Ala Ala Gly Arg Ile Pro Gly Gly Phe Phe Lys Arg
65                  70                  75                  80

Glu Arg Gly Ala Thr Glu Arg Glu Thr Leu Ile Ser Arg Leu Ile Asp
                85                  90                  95

Arg Pro Ile Arg Pro Leu Phe Pro Glu Gly Phe Tyr Asn Glu Thr Leu
            100                 105                 110

Val Ile Ala Gln Val Met Ser Tyr Asp Gly Glu Asn Glu Pro Asp Ile
        115                 120                 125

Leu Ala Met Ile Ala Ala Ser Ala Ala Leu Ala Leu Ser Gly Val Pro
    130                 135                 140

Phe Leu Gly Pro Ile Gly Ala Ala Arg Val Gly Tyr Gln Asp Gly Glu
145                 150                 155                 160

Phe Ile Leu Asn Pro Thr Leu Glu Gln Leu Glu Lys Ser Asp Leu Asp
                165                 170                 175

Leu Val Val Gly Ala Thr Arg Asp Ala Val Met Met Val Glu Ser Glu
            180                 185                 190

Ala Asn Glu Leu Pro Glu Glu Val Met Leu Asn Ala Val Ser Phe Ala
        195                 200                 205

His Glu Ser Leu Gln Pro Val Ile Lys Ala Ile Asn Leu Ala Glu
    210                 215                 220

Gln Ala Ala Lys Glu Pro Trp Glu Leu Val Ser Tyr Asp Asp Ser Ala
225                 230                 235                 240

Leu Ala Ala Lys Val Glu Glu Leu Cys Tyr Asp Asn Phe Asp Lys Ala
                245                 250                 255
```

-continued

```
Tyr Arg Leu Thr Arg Lys Ala Glu Arg Val Glu Ala Leu Ser Lys Ala
            260                 265                 270

Lys Ala Val Leu Asp Glu Ala Phe Pro Glu Ala Asp Pro Thr Glu Lys
            275                 280                 285

Leu Arg Ile Gln Lys Leu Ala Lys Lys Leu Glu Ala Lys Ile Val Arg
            290                 295                 300

Thr Ala Ile Leu Lys Glu Gly Arg Arg Ile Asp Gly Arg Asp Leu Lys
305                 310                 315                 320

Thr Val Arg Pro Ile Arg Ser Gln Val Gly Phe Leu Pro Arg Thr His
                    325                 330                 335

Gly Ser Ala Leu Phe Thr Arg Gly Glu Thr Gln Ala Leu Val Ser Thr
                    340                 345                 350

Thr Leu Gly Thr Ala Asp Ala Glu Gln Met Ile Asp Gly Leu Thr Gly
                355                 360                 365

Leu His Tyr Glu Arg Phe Met Leu His Tyr Asn Phe Pro Pro Tyr Ser
            370                 375                 380

Val Gly Glu Val Gly Arg Phe Gly Ala Pro Gly Arg Arg Glu Ile Gly
385                 390                 395                 400

His Gly Lys Leu Ala Trp Arg Ala Leu His Pro Val Leu Pro Ser Lys
                    405                 410                 415

Ala Asp Phe Pro Tyr Thr Ile Arg Val Leu Ser Asp Ile Thr Glu Ser
                    420                 425                 430

Asn Gly Ser Ser Ser Met Ala Thr Val Cys Gly Gly Cys Leu Ala Leu
                435                 440                 445

Met Asp Ala Gly Val Pro Leu Thr Arg Pro Val Ser Gly Ile Ala Met
450                 455                 460

Gly Leu Ile Leu Glu Lys Asp Gly Phe Ala Ile Leu Ser Asp Ile Met
465                 470                 475                 480

Gly Asp Glu Asp His Leu Gly Asp Met Asp Phe Lys Val Ala Gly Thr
                    485                 490                 495

Glu Lys Gly Ile Thr Ser Leu Gln Met Asp Ile Lys Val Ala Gly Ile
                500                 505                 510

Thr Glu Glu Ile Met Gln Lys Ala Leu Glu Gln Ala Lys Gly Gly Arg
            515                 520                 525

Ala His Ile Leu Gly Glu Met Ser Lys Ala Leu Gly Glu Val Arg Ser
530                 535                 540

Glu Ile Ser Asn Leu Ala Pro Arg Ile Glu Thr Met Ser Val Pro Lys
545                 550                 555                 560

Asp Lys Ile Arg Asp Val Ile Gly Thr Gly Gly Lys Val Ile Arg Glu
                    565                 570                 575

Ile Val Ala Thr Thr Gly Ala Lys Val Asp Ile Glu Asp Asp Gly Thr
                580                 585                 590

Val Arg Leu Ser Ser Ser Asp Pro Ala Asn Ile Glu Ala Ala Arg Glu
            595                 600                 605

Trp Ile Asn Gly Ile Val Glu Pro Glu Val Gly Lys Ile Tyr Asn
            610                 615                 620

Gly Lys Val Val Asn Ile Val Asp Phe Gly Ala Phe Val Asn Phe Met
625                 630                 635                 640

Gly Gly Arg Asp Gly Leu Val His Val Ser Glu Ile Lys Asn Glu Arg
                    645                 650                 655

Val Asn Lys Val Ser Asp Val Leu Ser Glu Gly Gln Glu Val Lys Val
                660                 665                 670
```

```
Lys Val Leu Glu Ile Asp Asn Arg Gly Lys Val Arg Leu Ser Met Arg
        675                 680                 685

Val Val Asp Gln Glu Thr Gly Ala Glu Leu Asp Asp Asn Arg Pro Pro
    690                 695                 700

Arg Glu Asn Ala Glu Arg Arg Gly Gly Glu Arg Pro Arg Arg Asp Arg
705                 710                 715                 720

Gly Pro Arg Arg Glu Ser Gly Asp Arg Pro Ala Arg Arg Asp Met Glu
                725                 730                 735

Pro Glu Phe Ala Pro Ala Phe Leu Arg Lys Asp Ser
            740                 745
```

<210> SEQ ID NO 19
<211> LENGTH: 2265
<212> TYPE: DNA
<213> ORGANISM: Zymomonas mobilis

<400> SEQUENCE: 19

| | | | | | |
|---|---|---|---|---|---|
| atgttcgata | ttaaacgcca | ggaaatcgat | tggggcggaa | agaagctgac | gctggaaacc | 60 |
| ggacaggttg | cccgtcaggc | agatggcgcc | gtcatcgcga | ccttaggtga | acggtcgtg | 120 |
| cttgcgcgg | taacagcggc | caaaacggtt | aaagagggac | aggattttt | ccctttaacg | 180 |
| gttcattatc | aagaaaaata | ttcagcagcc | ggtcgtatcc | ccggtggctt | tttcaagcgt | 240 |
| gaacgtggtg | ctagcgaacg | cgaaacttg | gtttcacgct | tgattgatcg | tccaattcgc | 300 |
| cccctttcc | cggacggttt | ttataacgaa | accttactta | tcgctcaggt | catgtcttat | 360 |
| gacggcgaaa | tgaacctga | catcttagcc | atgattgcgg | cctcggctgc | tcttgcgctt | 420 |
| tccggtgtgc | ctttcttggg | cccaattggt | gctgcgcgtg | ttggctatca | agatggcgaa | 480 |
| tatattttaa | atccgacctt | ggctcagctc | gaaaacagcg | atcttgatct | ggtagtcggt | 540 |
| gcaacgcgcg | atgccgtgat | gatggttgaa | tcggaagcaa | aagagctatc | cgaagaaatc | 600 |
| atgcttgatg | cggtttcctt | tgcgcataaa | tctttacagc | ctgttatcaa | ggcgatcatc | 660 |
| aatcttgccg | agcaagccgc | gaaagaaccg | tgggagctct | caagctatga | tgacacagct | 720 |
| ttggctgcaa | aagttgaaga | actttgcaaa | gatagccttg | ataaggccta | tcgtctgacc | 780 |
| aaaaaaagtg | aacgtgtaga | ggctattct | aaggccaaag | ccgtttgga | tgaagctttc | 840 |
| cccgatgctg | atgcctcgga | aaaactacgc | attcagaaat | ggcgaaaaa | acttgaagcc | 900 |
| aaaattgttc | gcactgcgat | cttaaaagaa | ggtcgtcgga | ttgatggtcg | tgatctaaaa | 960 |
| acggttcgtc | ctatccgttc | acaggttggt | ttcttacctc | ggacccatgg | gtctgcgctc | 1020 |
| tttacgcggg | gtgaaaccca | agccttggtt | tccacaaccc | ttggaaccgc | agatgctgag | 1080 |
| caaatgattg | atggcctgaa | tggccttcat | tacgaacgct | ttatgctgca | ttataacttc | 1140 |
| ccaccttatt | ccgttggtga | agtgggtcgt | tttggcgctc | ctggccgtcg | tgaaatcggt | 1200 |
| catggtaaac | tggcatggcg | tgctttacat | cctgtgcttc | ctagcaaggc | tgacttccct | 1260 |
| tatacgatcc | gcgttctatc | cgatattacg | gaatcaaacg | ttcttcctc | gatggcaacg | 1320 |
| gtctgcggtg | gctgtcttgc | tttgatggat | gcgggcgttc | ccttgaagcg | tccggtctcc | 1380 |
| ggcattgcga | tgggccttat | tcttgaaaaa | gatggtttg | ccattctttc | cgatattatg | 1440 |
| ggtgatgaag | atcacttagg | ggatatggac | tttaaggtag | ccggtacaga | agaaggcatt | 1500 |
| accagccttc | agatggacat | taaggttgct | ggtatcactg | aagaaatcat | gggtaaggct | 1560 |
| ttggaacagg | caaagccgg | ccgtgcccat | attttgggtg | aaatgtccaa | agctttgggt | 1620 |
| gaagttcgtt | cggaactttc | gaatttagcg | cctcgtattg | aaacaatgag | cgttcctaaa | 1680 |

```
gacaaaattc gtgatgttat tggaactggc ggtaaagtca ttcgtgagat tgttgcgaca    1740
accggcgcga agttgacatt tgaagatgac ggcaccgtac gcttgtcttc ttctgatccg    1800
gctcagatcg aagctgcccg taattggatt accggtatca tcgaagaacc ggaagtcggc    1860
aaaatttata acgtaaggtt gtcaacatt gttgatttcg gtgcctttgt gaatttcatg     1920
ggtggccgtg atggtctggt tcacgtctct gaaattaaaa acgagcgcgt gaacaaggtc    1980
agtgacgttc tggccgaagg ccaggaagtt aaggttaagg tgcttgaaat tgacaatcgc    2040
ggtaaagtcc gcttgtcaat gcgtgttgtc gatcaggaaa ctggcgcgga actggaagac    2100
aatcgtccgc ctagggaagc tcgtgaagtc agtgatcgcg gtccacgggg tgatcggcct    2160
cgtcgcgatc gtggcccacg tcgcgaaccg cagaatggtt caaaccattc aggccgtgat    2220
atggaacccg aatttgctcc ggcttttta cgaaaagatg attaa                     2265
```

<210> SEQ ID NO 20
<211> LENGTH: 754
<212> TYPE: PRT
<213> ORGANISM: Zymomonas mobilis

<400> SEQUENCE: 20

```
Met Phe Asp Ile Lys Arg Gln Glu Ile Asp Trp Gly Gly Lys Lys Leu
1               5                   10                  15

Thr Leu Glu Thr Gly Gln Val Ala Arg Gln Ala Asp Gly Ala Val Ile
            20                  25                  30

Ala Thr Leu Gly Glu Thr Val Leu Cys Ala Val Thr Ala Ala Lys
        35                  40                  45

Thr Val Lys Glu Gly Gln Asp Phe Phe Pro Leu Thr Val His Tyr Gln
    50                  55                  60

Glu Lys Tyr Ser Ala Ala Gly Arg Ile Pro Gly Gly Phe Phe Lys Arg
65                  70                  75                  80

Glu Arg Gly Ala Ser Glu Arg Glu Thr Leu Val Ser Arg Leu Ile Asp
                85                  90                  95

Arg Pro Ile Arg Pro Leu Phe Pro Asp Gly Phe Tyr Asn Glu Thr Leu
            100                 105                 110

Leu Ile Ala Gln Val Met Ser Tyr Asp Gly Glu Asn Glu Pro Asp Ile
        115                 120                 125

Leu Ala Met Ile Ala Ala Ser Ala Ala Leu Ala Leu Ser Gly Val Pro
    130                 135                 140

Phe Leu Gly Pro Ile Gly Ala Ala Arg Val Gly Tyr Gln Asp Gly Glu
145                 150                 155                 160

Tyr Ile Leu Asn Pro Thr Leu Ala Gln Leu Glu Asn Ser Asp Leu Asp
                165                 170                 175

Leu Val Val Gly Ala Thr Arg Asp Ala Val Met Met Val Glu Ser Glu
            180                 185                 190

Ala Lys Glu Leu Ser Glu Glu Ile Met Leu Asp Ala Val Ser Phe Ala
        195                 200                 205

His Lys Ser Leu Gln Pro Val Ile Lys Ala Ile Asn Leu Ala Glu
    210                 215                 220

Gln Ala Ala Lys Glu Pro Trp Glu Leu Ser Ser Tyr Asp Asp Thr Ala
225                 230                 235                 240

Leu Ala Ala Lys Val Glu Glu Leu Cys Lys Asp Ser Leu Asp Lys Ala
                245                 250                 255

Tyr Arg Leu Thr Lys Lys Ser Glu Arg Val Glu Ala Ile Ser Lys Ala
            260                 265                 270
```

```
Lys Ala Val Leu Asp Glu Ala Phe Pro Asp Ala Asp Ala Ser Glu Lys
            275                 280                 285

Leu Arg Ile Gln Lys Leu Ala Lys Lys Leu Glu Ala Lys Ile Val Arg
        290                 295                 300

Thr Ala Ile Leu Lys Glu Gly Arg Arg Ile Asp Gly Arg Asp Leu Lys
305                 310                 315                 320

Thr Val Arg Pro Ile Arg Ser Gln Val Gly Phe Leu Pro Arg Thr His
                325                 330                 335

Gly Ser Ala Leu Phe Thr Arg Gly Glu Thr Gln Ala Leu Val Ser Thr
            340                 345                 350

Thr Leu Gly Thr Ala Asp Ala Glu Gln Met Ile Asp Gly Leu Asn Gly
        355                 360                 365

Leu His Tyr Glu Arg Phe Met Leu His Tyr Asn Phe Pro Pro Tyr Ser
    370                 375                 380

Val Gly Glu Val Gly Arg Phe Gly Ala Pro Gly Arg Arg Glu Ile Gly
385                 390                 395                 400

His Gly Lys Leu Ala Trp Arg Ala Leu His Pro Val Leu Pro Ser Lys
                405                 410                 415

Ala Asp Phe Pro Tyr Thr Ile Arg Val Leu Ser Asp Ile Thr Glu Ser
            420                 425                 430

Asn Gly Ser Ser Ser Met Ala Thr Val Cys Gly Gly Cys Leu Ala Leu
        435                 440                 445

Met Asp Ala Gly Val Pro Leu Lys Arg Pro Val Ser Gly Ile Ala Met
450                 455                 460

Gly Leu Ile Leu Glu Lys Asp Gly Phe Ala Ile Leu Ser Asp Ile Met
465                 470                 475                 480

Gly Asp Glu Asp His Leu Gly Asp Met Asp Phe Lys Val Ala Gly Thr
                485                 490                 495

Glu Glu Gly Ile Thr Ser Leu Gln Met Asp Ile Lys Val Ala Gly Ile
            500                 505                 510

Thr Glu Glu Ile Met Gly Lys Ala Leu Glu Gln Ala Lys Ala Gly Arg
        515                 520                 525

Ala His Ile Leu Gly Glu Met Ser Lys Ala Leu Gly Glu Val Arg Ser
530                 535                 540

Glu Leu Ser Asn Leu Ala Pro Arg Ile Glu Thr Met Ser Val Pro Lys
545                 550                 555                 560

Asp Lys Ile Arg Asp Val Ile Gly Thr Gly Gly Lys Val Ile Arg Glu
                565                 570                 575

Ile Val Ala Thr Thr Gly Ala Lys Val Asp Ile Glu Asp Asp Gly Thr
            580                 585                 590

Val Arg Leu Ser Ser Ser Asp Pro Ala Gln Ile Glu Ala Ala Arg Asn
        595                 600                 605

Trp Ile Thr Gly Ile Ile Glu Glu Pro Glu Val Gly Lys Ile Tyr Asn
610                 615                 620

Gly Lys Val Val Asn Ile Val Asp Phe Gly Ala Phe Val Asn Phe Met
625                 630                 635                 640

Gly Gly Arg Asp Gly Leu Val His Val Ser Glu Ile Lys Asn Glu Arg
                645                 650                 655

Val Asn Lys Val Ser Asp Val Leu Ala Glu Gly Gln Glu Val Lys Val
            660                 665                 670

Lys Val Leu Glu Ile Asp Asn Arg Gly Lys Val Arg Leu Ser Met Arg
        675                 680                 685

Val Val Asp Gln Glu Thr Gly Ala Glu Leu Glu Asp Asn Arg Pro Pro
```

```
                690               695                700
Arg Glu Ala Arg Glu Val Ser Asp Arg Gly Pro Arg Gly Asp Arg Pro
705                 710                 715                 720

Arg Arg Asp Arg Gly Pro Arg Arg Glu Pro Gln Asn Gly Ser Asn His
              725                 730                 735

Ser Gly Arg Asp Met Glu Pro Glu Phe Ala Pro Ala Phe Leu Arg Lys
              740                 745                 750

Asp Asp

<210> SEQ ID NO 21
<211> LENGTH: 723
<212> TYPE: PRT
<213> ORGANISM: artificial sequence
<220> FEATURE:
<223> OTHER INFORMATION: engineered fusion protein

<400> SEQUENCE: 21

Met Phe Asp Ile Lys Arg Gln Glu Ile Asp Trp Gly Gly Lys Lys Leu
1               5                   10                  15

Thr Leu Glu Thr Gly Gln Val Ala Arg Gln Ala Asp Gly Ala Val Ile
            20                  25                  30

Ala Thr Leu Gly Glu Thr Val Leu Cys Ala Val Thr Ala Ala Lys
        35                  40                  45

Thr Val Lys Glu Gly Gln Asp Phe Phe Pro Leu Thr Val His Tyr Gln
50                  55                  60

Glu Lys Tyr Ser Ala Ala Gly Arg Ile Pro Gly Gly Phe Phe Lys Arg
65                  70                  75                  80

Glu Arg Gly Ala Thr Glu Arg Glu Thr Leu Ile Ser Arg Leu Ile Asp
                85                  90                  95

Arg Pro Ile Arg Pro Leu Phe Pro Glu Gly Phe Tyr Asn Glu Thr Leu
            100                 105                 110

Val Ile Ala Gln Val Met Ser Tyr Asp Gly Glu Asn Glu Pro Asp Ile
        115                 120                 125

Leu Ala Met Ile Ala Ala Ser Ala Ala Leu Ala Leu Ser Gly Val Pro
130                 135                 140

Phe Leu Gly Pro Ile Gly Ala Ala Arg Val Gly Tyr Gln Asp Gly Glu
145                 150                 155                 160

Phe Ile Leu Asn Pro Thr Leu Glu Gln Leu Glu Lys Ser Asp Leu Asp
                165                 170                 175

Leu Val Val Gly Ala Thr Arg Asp Ala Val Met Met Val Glu Ser Glu
            180                 185                 190

Ala Asn Glu Leu Pro Glu Glu Val Met Leu Asn Ala Val Ser Phe Ala
        195                 200                 205

His Glu Ser Leu Gln Pro Val Ile Lys Ala Ile Asn Leu Ala Glu
210                 215                 220

Gln Ala Ala Lys Glu Pro Trp Glu Leu Val Ser Tyr Asp Ser Ala
225                 230                 235                 240

Leu Ala Ala Lys Val Glu Glu Leu Cys Tyr Asp Asn Phe Asp Lys Ala
                245                 250                 255

Tyr Arg Leu Thr Arg Lys Ala Glu Arg Val Asp Ala Leu Ser Lys Ala
            260                 265                 270

Lys Ala Val Leu Asp Glu Ala Phe Pro Glu Ala Asp Pro Thr Glu Lys
        275                 280                 285

Leu Arg Ile Gln Lys Leu Ala Lys Lys Leu Glu Ala Lys Ile Val Arg
290                 295                 300
```

```
Thr Ala Ile Leu Lys Glu Gly Arg Arg Ile Asp Gly Arg Asp Leu Lys
305                 310                 315                 320

Thr Val Arg Pro Ile Arg Ser Gln Val Gly Phe Leu Pro Arg Thr His
            325                 330                 335

Gly Ser Ala Leu Phe Thr Arg Gly Glu Thr Gln Ala Leu Val Ser Thr
            340                 345                 350

Thr Leu Gly Thr Ala Asp Ala Glu Gln Met Ile Asp Gly Leu Thr Gly
            355                 360                 365

Leu His Tyr Glu Arg Phe Met Leu His Tyr Asn Phe Pro Pro Tyr Ser
        370                 375                 380

Val Gly Glu Val Gly Arg Phe Gly Ala Pro Gly Arg Arg Glu Ile Gly
385                 390                 395                 400

His Gly Lys Leu Ala Trp Arg Ala Leu His Pro Val Leu Pro Ser Lys
                405                 410                 415

Ala Asp Phe Pro Tyr Thr Ile Arg Val Leu Ser Asp Ile Thr Glu Ser
            420                 425                 430

Asn Gly Ser Ser Ser Met Ala Thr Val Cys Gly Gly Cys Leu Ala Leu
        435                 440                 445

Met Asp Ala Gly Val Pro Leu Thr Arg Pro Val Ser Gly Ile Ala Met
    450                 455                 460

Gly Leu Ile Leu Glu Lys Asp Gly Phe Ala Ile Leu Ser Asp Ile Met
465                 470                 475                 480

Gly Asp Glu Asp His Leu Gly Asp Met Asp Phe Lys Val Ala Gly Thr
                485                 490                 495

Glu Lys Gly Ile Thr Ser Leu Gln Met Asp Ile Lys Val Ala Gly Ile
            500                 505                 510

Thr Glu Glu Ile Met Gln Lys Ala Leu Glu Gln Ala Lys Gly Gly Arg
            515                 520                 525

Ala His Ile Leu Gly Glu Met Ser Lys Ala Leu Gly Glu Val Arg Ser
    530                 535                 540

Glu Ile Ser Asn Leu Ala Pro Arg Ile Glu Thr Met Ser Val Pro Lys
545                 550                 555                 560

Asp Lys Ile Arg Asp Val Ile Gly Thr Gly Lys Val Ile Arg Glu
                565                 570                 575

Ile Val Ala Thr Thr Gly Ala Lys Val Asp Ile Glu Asp Asp Gly Thr
                580                 585                 590

Val Arg Leu Ser Ser Ser Asp Pro Ala Asn Ile Glu Ala Ala Arg Glu
        595                 600                 605

Trp Ile Asn Gly Ile Val Glu Glu Pro Glu Val Gly Lys Ile Tyr Asn
    610                 615                 620

Gly Lys Val Val Asn Ile Val Asp Phe Gly Ala Phe Val Asn Phe Met
625                 630                 635                 640

Gly Gly Arg Asp Gly Leu Val His Val Ser Glu Ile Lys Asn Glu Arg
                645                 650                 655

Val Asn Lys Val Ser Asp Val Leu Ser Glu Gly Gln Glu Val Lys Val
            660                 665                 670

Lys Val Leu Glu Ile Asp Asn Arg Gly Lys Val Arg Leu Ser Met Arg
        675                 680                 685

Val Val Asp Gln Glu Thr Gly Ala Glu Leu Asp Asp Asn Arg Pro Pro
    690                 695                 700

Arg Glu Asn Ala Glu Pro Val Ser Tyr Thr His Leu Asn Pro Glu Ala
705                 710                 715                 720
```

Leu Val Gly

<210> SEQ ID NO 22
<211> LENGTH: 697
<212> TYPE: PRT
<213> ORGANISM: artificial sequence
<220> FEATURE:
<223> OTHER INFORMATION: engineered fusion protien

<400> SEQUENCE: 22

Met Phe Asp Ile Lys Arg Gln Glu Ile Asp Trp Gly Gly Lys Lys Leu
1               5                   10                  15

Thr Leu Glu Thr Gly Gln Val Ala Arg Gln Ala Asp Gly Ala Val Ile
            20                  25                  30

Ala Thr Leu Gly Glu Thr Val Val Leu Cys Ala Val Thr Ala Ala Lys
        35                  40                  45

Thr Val Lys Glu Gly Gln Asp Phe Phe Pro Leu Thr Val His Tyr Gln
    50                  55                  60

Glu Lys Tyr Ser Ala Ala Gly Arg Ile Pro Gly Gly Phe Phe Lys Arg
65                  70                  75                  80

Glu Arg Gly Ala Thr Glu Arg Glu Thr Leu Ile Ser Arg Leu Ile Asp
                85                  90                  95

Arg Pro Ile Arg Pro Leu Phe Pro Glu Gly Phe Tyr Asn Glu Thr Leu
            100                 105                 110

Val Ile Ala Gln Val Met Ser Tyr Asp Gly Glu Asn Glu Pro Asp Ile
        115                 120                 125

Leu Ala Met Ile Ala Ala Ser Ala Ala Leu Ala Leu Ser Gly Val Pro
    130                 135                 140

Phe Leu Gly Pro Ile Gly Ala Ala Arg Val Gly Tyr Gln Asp Gly Glu
145                 150                 155                 160

Phe Ile Leu Asn Pro Thr Leu Glu Gln Leu Glu Lys Ser Asp Leu Asp
                165                 170                 175

Leu Val Val Gly Ala Thr Arg Asp Ala Val Met Met Val Glu Ser Glu
            180                 185                 190

Ala Asn Glu Leu Pro Glu Glu Val Met Leu Asn Ala Val Ser Phe Ala
        195                 200                 205

His Glu Ser Leu Gln Pro Val Ile Lys Ala Ile Ile Asn Leu Ala Glu
    210                 215                 220

Gln Ala Ala Lys Glu Pro Trp Glu Leu Val Ser Tyr Asp Asp Ser Ala
225                 230                 235                 240

Leu Ala Ala Lys Val Glu Glu Leu Cys Tyr Asp Asn Phe Asp Lys Ala
                245                 250                 255

Tyr Arg Leu Thr Arg Lys Ala Glu Arg Val Asp Ala Leu Ser Lys Ala
            260                 265                 270

Lys Ala Val Leu Asp Glu Ala Phe Pro Glu Ala Asp Pro Thr Glu Lys
        275                 280                 285

Leu Arg Ile Gln Lys Leu Ala Lys Lys Leu Glu Ala Lys Ile Val Arg
    290                 295                 300

Thr Ala Ile Leu Lys Glu Gly Arg Arg Ile Asp Gly Arg Asp Leu Lys
305                 310                 315                 320

Thr Val Arg Pro Ile Arg Ser Gln Val Gly Phe Leu Pro Arg Thr His
                325                 330                 335

Gly Ser Ala Leu Phe Thr Arg Gly Glu Thr Gln Ala Leu Val Ser Thr
            340                 345                 350

Thr Leu Gly Thr Ala Asp Ala Glu Gln Met Ile Asp Gly Leu Thr Gly

```
                355                 360                 365
Leu His Tyr Glu Arg Phe Met Leu His Tyr Asn Phe Pro Pro Tyr Ser
            370                 375                 380

Val Gly Glu Val Gly Arg Phe Gly Ala Pro Gly Arg Glu Ile Gly
385                 390                 395                 400

His Gly Lys Leu Ala Trp Arg Ala Leu His Pro Val Leu Pro Ser Lys
                405                 410                 415

Ala Asp Phe Pro Tyr Thr Ile Arg Val Leu Ser Asp Ile Thr Glu Ser
            420                 425                 430

Asn Gly Ser Ser Ser Met Ala Thr Val Cys Gly Gly Cys Leu Ala Leu
            435                 440                 445

Met Asp Ala Gly Val Pro Leu Thr Arg Pro Val Ser Gly Ile Ala Met
        450                 455                 460

Gly Leu Ile Leu Glu Lys Asp Gly Phe Ala Ile Leu Ser Asp Ile Met
465                 470                 475                 480

Gly Asp Glu Asp His Leu Gly Asp Met Asp Phe Lys Val Ala Gly Thr
                485                 490                 495

Glu Lys Gly Ile Thr Ser Leu Gln Met Asp Ile Lys Val Ala Gly Ile
            500                 505                 510

Thr Glu Glu Ile Met Gln Lys Ala Leu Glu Gln Ala Lys Gly Gly Arg
        515                 520                 525

Ala His Ile Leu Gly Glu Met Ser Lys Ala Leu Gly Glu Val Arg Ser
530                 535                 540

Glu Ile Ser Asn Leu Ala Pro Arg Ile Glu Thr Met Ser Val Pro Lys
545                 550                 555                 560

Asp Lys Ile Arg Asp Val Ile Gly Thr Gly Gly Lys Val Ile Arg Glu
                565                 570                 575

Ile Val Ala Thr Thr Gly Ala Lys Val Asp Ile Glu Asp Asp Gly Thr
            580                 585                 590

Val Arg Leu Ser Ser Ser Asp Pro Ala Asn Ile Glu Ala Ala Arg Glu
        595                 600                 605

Trp Ile Asn Gly Ile Val Glu Glu Pro Glu Val Gly Lys Ile Tyr Asn
610                 615                 620

Gly Lys Val Val Asn Ile Val Asp Phe Gly Ala Phe Val Asn Phe Met
625                 630                 635                 640

Gly Gly Arg Asp Gly Leu Val His Val Ser Glu Ile Lys Asn Glu Arg
                645                 650                 655

Val Asn Lys Val Ser Asp Val Leu Ser Glu Gly Gln Glu Val Lys Val
            660                 665                 670

Lys Val Leu Glu Ile Asp Asn Arg Gly Lys Val Arg Leu Ser Met Arg
        675                 680                 685

Val Val Asp Gln Glu Thr Gly Leu Val
            690                 695

<210> SEQ ID NO 23
<211> LENGTH: 378
<212> TYPE: PRT
<213> ORGANISM: artificial sequence
<220> FEATURE:
<223> OTHER INFORMATION: engineered fusion protein

<400> SEQUENCE: 23

Met Phe Asp Ile Lys Arg Gln Glu Ile Asp Trp Gly Gly Lys Lys Leu
1               5                   10                  15

Thr Leu Glu Thr Gly Gln Val Ala Arg Gln Ala Asp Gly Ala Val Ile
```

```
            20                  25                  30
Ala Thr Leu Gly Glu Thr Val Val Leu Cys Ala Val Thr Ala Ala Lys
        35                  40                  45

Thr Val Lys Glu Gly Gln Asp Phe Pro Leu Thr Val His Tyr Gln
    50                  55                  60

Glu Lys Tyr Ser Ala Ala Gly Arg Ile Pro Gly Phe Phe Lys Arg
65                  70                  75                  80

Glu Arg Gly Ala Thr Glu Arg Glu Thr Leu Ile Ser Arg Leu Ile Asp
                85                  90                  95

Arg Pro Ile Arg Pro Leu Phe Pro Glu Gly Phe Tyr Asn Glu Thr Leu
            100                 105                 110

Val Ile Ala Gln Val Met Ser Tyr Asp Gly Glu Asn Glu Pro Asp Ile
        115                 120                 125

Leu Ala Met Ile Ala Ala Ser Ala Ala Leu Ala Leu Ser Gly Val Pro
    130                 135                 140

Phe Leu Gly Pro Ile Gly Ala Ala Arg Val Gly Tyr Gln Asp Gly Glu
145                 150                 155                 160

Phe Ile Leu Asn Pro Thr Leu Glu Gln Leu Glu Lys Ser Asp Leu Asp
                165                 170                 175

Leu Val Val Gly Ala Thr Arg Asp Ala Val Met Met Val Glu Ser Glu
            180                 185                 190

Ala Asn Glu Leu Pro Glu Glu Val Met Leu Asn Ala Val Ser Phe Ala
        195                 200                 205

His Glu Ser Leu Gln Pro Val Ile Lys Ala Ile Ile Asn Leu Ala Glu
    210                 215                 220

Gln Ala Ala Lys Glu Pro Trp Glu Leu Val Ser Tyr Asp Asp Ser Ala
225                 230                 235                 240

Leu Ala Ala Lys Val Glu Glu Leu Cys Tyr Asp Asn Phe Asp Lys Ala
                245                 250                 255

Tyr Arg Leu Thr Arg Lys Ala Glu Arg Val Asp Ala Leu Ser Lys Ala
            260                 265                 270

Lys Ala Val Leu Asp Glu Ala Phe Pro Glu Ala Asp Pro Thr Glu Lys
        275                 280                 285

Leu Arg Ile Gln Lys Leu Ala Lys Lys Leu Glu Ala Lys Ile Val Arg
    290                 295                 300

Thr Ala Ile Leu Lys Glu Gly Arg Arg Ile Asp Gly Arg Asp Leu Lys
305                 310                 315                 320

Thr Val Arg Pro Ile Arg Ser Gln Val Gly Phe Leu Pro Arg Thr His
                325                 330                 335

Gly Ser Ala Leu Phe Thr Arg Gly Glu Thr Gln Ala Leu Val Ser Thr
            340                 345                 350

Thr Leu Gly Thr Ala Asp Ala Glu Gln Met Ile Asp Gly Leu Thr Gly
        355                 360                 365

Thr Ser Val Thr Glu Asp His Phe Ala Glu
    370                 375

<210> SEQ ID NO 24
<211> LENGTH: 49
<212> TYPE: PRT
<213> ORGANISM: artificial sequence
<220> FEATURE:
<223> OTHER INFORMATION: engineered fusion protein

<400> SEQUENCE: 24

Met Phe Asp Ile Lys Arg Gln Glu Ile Asp Trp Gly Gly Lys Lys Leu
```

```
1               5                   10                  15
Thr Leu Glu Thr Gly Gln Val Ala Arg Gln Ala Asp Gly Ala Val Ile
                20                  25                  30
Asn Ala Glu Pro Val Ser Tyr Thr His Leu Asn Pro Glu Ala Leu Val
                35                  40                  45
Gly
```

<210> SEQ ID NO 25
<211> LENGTH: 1500
<212> TYPE: DNA
<213> ORGANISM: Escherichia coli

<400> SEQUENCE: 25

```
atgacgattt tgataatta tgaagtgtgg tttgtcattg gcagccagca tctgtatggc     60
ccggaaaccc tgcgtcaggt cacccaacat gccgagcacg tcgttaatgc gctgaatacg    120
gaagcgaaac tgccctgcaa actggtgttg aaaccgctgg caccacgcc ggatgaaatc     180
accgctattt gccgcgacgc gaattacgac gatcgttgcg ctggtctggt ggtgtggctg    240
cacaccttct ccccggccaa atgtggatc aacggcctga ccatgctcaa caaaccgttg     300
ctgcaattcc acacccagtt caacgcggcg ctgccgtggg acagtatcga tatggacttt    360
atgaacctga ccagactgc acatggcggt cgcgagttcg gcttcattgg cgcgcgtatg    420
cgtcagcaac atgccgtggt taccggtcac tggcaggata acaagcccca tgagcgtatc    480
ggctcctgga tgcgtcaggc ggtctctaaa caggataccc gtcatctgaa agtctgccga    540
tttggcgata catgcgtga agtggcggtc accgatggcg ataaagttgc cgcacagatc     600
aagttcggtt ctccgtcaa tacctgggcg gttggcgatc tggtgcaggt ggtgaactcc    660
atcagcgacg gcgatgttaa cgcgctggtc gatgagtacg aaagctgcta caccatgacg    720
cctgccacac aaatccacgg caaaaaacga cagaacgtgc tggaagcggc gcgtattgag    780
ctggggatga gcgtttcct ggaacaaggt ggcttccacg cgttcaccac cacctttgaa     840
gatttgcacg gtctgaaaca gcttcctggt ctggccgtac agcgtctgat gcagcagggt    900
tacggctttg cgggcgaagg cgactggaaa actgccgccc tgcttcgcat catgaaggtg    960
atgtcaaccg gtctgcaggg cggcacctcc tttatggagg actacaccta tcacttcgag   1020
aaaggtaatg acctggtgct cggctcccat atgctgaag tctgcccgtc gatcgccgca    1080
gaagagaaac cgatcctcga cgttcagcat ctcggtattg gtggtaagga cgatcctgcc   1140
cgcctgatct tcaataccca aaccggccca gcgattgtcg ccagcttgat tgatctcggc   1200
gatcgttacc gtctactggt taactgcatc gacacggtga aaacaccgca ctccctgccg   1260
aaactgccgg tggcgaatgc gctgtggaaa gcgcaaccgg atctgccaac tgcttccgaa   1320
gcgtggatcc tcgctggtgg cgcgcaccat accgtcttca gccatgcact gaacctcaac   1380
gatatgcgcc aattcgccga gatgcacgac attgaaatca cggtgattga taacgacaca   1440
cgcctgccag cgtttaaaga cgcgctgcgc tggaacgaag tgtattacgg atttcgtcgc   1500
```

<210> SEQ ID NO 26
<211> LENGTH: 500
<212> TYPE: PRT
<213> ORGANISM: Escherichia coli

<400> SEQUENCE: 26

```
Met Thr Ile Phe Asp Asn Tyr Glu Val Trp Phe Val Ile Gly Ser Gln
1               5                   10                  15
```

-continued

His Leu Tyr Gly Pro Glu Thr Leu Arg Gln Val Thr Gln His Ala Glu
         20                  25                  30

His Val Val Asn Ala Leu Asn Thr Glu Ala Lys Leu Pro Cys Lys Leu
             35                  40                  45

Val Leu Lys Pro Leu Gly Thr Thr Pro Asp Glu Ile Thr Ala Ile Cys
 50                  55                  60

Arg Asp Ala Asn Tyr Asp Asp Arg Cys Ala Gly Leu Val Val Trp Leu
 65                  70                  75                  80

His Thr Phe Ser Pro Ala Lys Met Trp Ile Asn Gly Leu Thr Met Leu
                 85                  90                  95

Asn Lys Pro Leu Leu Gln Phe His Thr Gln Phe Asn Ala Ala Leu Pro
                100                 105                 110

Trp Asp Ser Ile Asp Met Asp Phe Met Asn Leu Asn Gln Thr Ala His
            115                 120                 125

Gly Gly Arg Glu Phe Gly Phe Ile Gly Ala Arg Met Arg Gln Gln His
        130                 135                 140

Ala Val Val Thr Gly His Trp Gln Asp Lys Gln Ala His Glu Arg Ile
145                 150                 155                 160

Gly Ser Trp Met Arg Gln Ala Val Ser Lys Gln Asp Thr Arg His Leu
                165                 170                 175

Lys Val Cys Arg Phe Gly Asp Asn Met Arg Glu Val Ala Val Thr Asp
            180                 185                 190

Gly Asp Lys Val Ala Ala Gln Ile Lys Phe Gly Phe Ser Val Asn Thr
        195                 200                 205

Trp Ala Val Gly Asp Leu Val Gln Val Val Asn Ser Ile Ser Asp Gly
210                 215                 220

Asp Val Asn Ala Leu Val Asp Glu Tyr Glu Ser Cys Tyr Thr Met Thr
225                 230                 235                 240

Pro Ala Thr Gln Ile His Gly Lys Lys Arg Gln Asn Val Leu Glu Ala
                245                 250                 255

Ala Arg Ile Glu Leu Gly Met Lys Arg Phe Leu Glu Gln Gly Gly Phe
            260                 265                 270

His Ala Phe Thr Thr Thr Phe Glu Asp Leu His Gly Leu Lys Gln Leu
        275                 280                 285

Pro Gly Leu Ala Val Gln Arg Leu Met Gln Gln Gly Tyr Gly Phe Ala
290                 295                 300

Gly Glu Gly Asp Trp Lys Thr Ala Ala Leu Leu Arg Ile Met Lys Val
305                 310                 315                 320

Met Ser Thr Gly Leu Gln Gly Gly Thr Ser Phe Met Glu Asp Tyr Thr
                325                 330                 335

Tyr His Phe Glu Lys Gly Asn Asp Leu Val Leu Gly Ser His Met Leu
            340                 345                 350

Glu Val Cys Pro Ser Ile Ala Ala Glu Glu Lys Pro Ile Leu Asp Val
        355                 360                 365

Gln His Leu Gly Ile Gly Gly Lys Asp Pro Ala Arg Leu Ile Phe
370                 375                 380

Asn Thr Gln Thr Gly Pro Ala Ile Val Ala Ser Leu Ile Asp Leu Gly
385                 390                 395                 400

Asp Arg Tyr Arg Leu Leu Val Asn Cys Ile Asp Thr Val Lys Thr Pro
                405                 410                 415

His Ser Leu Pro Lys Leu Pro Val Ala Asn Ala Leu Trp Lys Ala Gln
            420                 425                 430

Pro Asp Leu Pro Thr Ala Ser Glu Ala Trp Ile Leu Ala Gly Gly Ala

```
                   435                 440                 445
His His Thr Val Phe Ser His Ala Leu Asn Leu Asn Asp Met Arg Gln
    450                 455                 460

Phe Ala Glu Met His Asp Ile Glu Ile Thr Val Ile Asp Asn Asp Thr
465                 470                 475                 480

Arg Leu Pro Ala Phe Lys Asp Ala Leu Arg Trp Asn Glu Val Tyr Tyr
                485                 490                 495

Gly Phe Arg Arg
            500

<210> SEQ ID NO 27
<211> LENGTH: 1698
<212> TYPE: DNA
<213> ORGANISM: Escherichia coli

<400> SEQUENCE: 27
```

| | | | | | |
|---|---|---|---|---|---|
| atggcgattg | caattggcct | cgattttggc | agtgattctg | tgcgagcttt | ggcggtggac | 60 |
| tgcgctaccg | gtgaagagat | cgccaccagc | gtagagtggt | atccccgttg | cagaaaggg | 120 |
| caatttgtg | atgccccgaa | taaccagttc | cgtcatcatc | cgcgtgacta | cattgagtca | 180 |
| atggaagcg | cactgaaaac | cgtgcttgca | gagcttagcg | tcgaacagcg | cgcagctgtg | 240 |
| gtcgggattg | gcgttgacag | taccggctcg | acgcccgcac | cgattgatgc | cgacggaaac | 300 |
| gtgctggcgc | tgcgcccgga | gtttgccgaa | acccgaacg | cgatgttcgt | attgtggaaa | 360 |
| gaccacactg | cggttgaaga | agcggaagag | attacccgtt | tgtgccacgc | gccgggcaac | 420 |
| gttgactact | cccgctacat | tggtggtatt | tattccagcg | aatggttctg | gcaaaaatc | 480 |
| ctgcatgtga | ctcgccagga | cagcgccgtg | gcgcaatctg | ccgcatcgtg | gattgagctg | 540 |
| tgcgactggg | tgccagctct | gctttccggt | accacccgcc | cgcaggatat | cgtcgcgga | 600 |
| cgttgcagcg | ccgggcataa | atctctgtgg | cacgaaagct | ggggcggcct | gccgccagcc | 660 |
| agtttctttg | atgagctgga | cccgatcctc | aatcgccatt | tgccttcccc | gctgttcact | 720 |
| gacacttgga | ctgccgatat | tccggtgggc | accttatgcc | cggaatgggc | gcagcgtctc | 780 |
| ggcctgcctg | aaagcgtggt | gatttccggc | ggcgcgtttg | actgccatat | gggcgcagtt | 840 |
| ggcgcaggcg | cacagcctaa | cgcactggta | aaagttatcg | gtacttccac | tgcgacatt | 900 |
| ctgattgccg | acaaacagag | cgttggcgag | cgggcagtta | aaggtatttg | cggtcaggtt | 960 |
| gatggcagcg | tggtgcctgg | atttatcggt | ctggaagcag | gccaatcggc | gtttggtgat | 1020 |
| atctacgcct | ggtttggtcg | cgtactcggc | tggccgctgg | aacagcttgc | cgcccagcat | 1080 |
| ccggaactga | aaacgcaaat | caacgccagc | cagaaacaac | tgcttccggc | gctgaccgaa | 1140 |
| gcatgggcca | aaaatccgtc | tctggatcac | ctgccggtgg | tgctcgactg | gtttaacggc | 1200 |
| cgccgcacac | cgaacgctaa | ccaacgcctg | aaagggtga | ttaccgatct | taacctcgct | 1260 |
| accgacgctc | cgctgctgtt | cggcggtttg | attgctgcca | ccgcctttgg | cgcacgcgca | 1320 |
| atcatggagt | gctttaccga | tcaggggatc | gccgttaata | acgtgatggc | actgggcggc | 1380 |
| atcgcgcgga | aaaccaggt | cattatgcag | gcctgctgcg | acgtgctgaa | tcgcccgctg | 1440 |
| caaattgttg | cctctgacca | gtgctgtgcg | ctcggtgcgg | cgattttgc | tgccgtcgcc | 1500 |
| gcgaaagtgc | acgcagacat | cccatcagct | cagcaaaaaa | tggccagtgc | ggtagagaaa | 1560 |
| accctgcaac | cgtgcagcga | gcaggcacaa | cgctttgaac | agctttatcg | ccgctatcag | 1620 |
| caatgggcga | tgacgccga | acaacactat | cttccaactt | ccgccccggc | acaggctgcc | 1680 |
| caggccgttg | cgactcta | | | | | 1698 |

<210> SEQ ID NO 28
<211> LENGTH: 566
<212> TYPE: PRT
<213> ORGANISM: Escherichia coli

<400> SEQUENCE: 28

```
Met Ala Ile Ala Ile Gly Leu Asp Phe Gly Ser Asp Ser Val Arg Ala
1               5                   10                  15

Leu Ala Val Asp Cys Ala Thr Gly Glu Ile Ala Thr Ser Val Glu
            20                  25                  30

Trp Tyr Pro Arg Trp Gln Lys Gly Gln Phe Cys Asp Ala Pro Asn Asn
        35                  40                  45

Gln Phe Arg His His Pro Arg Asp Tyr Ile Glu Ser Met Glu Ala Ala
    50                  55                  60

Leu Lys Thr Val Leu Ala Glu Leu Ser Val Glu Gln Arg Ala Ala Val
65                  70                  75                  80

Val Gly Ile Gly Val Asp Ser Thr Gly Ser Thr Pro Ala Pro Ile Asp
                85                  90                  95

Ala Asp Gly Asn Val Leu Ala Leu Arg Pro Glu Phe Ala Glu Asn Pro
            100                 105                 110

Asn Ala Met Phe Val Leu Trp Lys Asp His Thr Ala Val Glu Glu Ala
        115                 120                 125

Glu Glu Ile Thr Arg Leu Cys His Ala Pro Gly Asn Val Asp Tyr Ser
    130                 135                 140

Arg Tyr Ile Gly Gly Ile Tyr Ser Ser Glu Trp Phe Trp Ala Lys Ile
145                 150                 155                 160

Leu His Val Thr Arg Gln Asp Ser Ala Val Ala Gln Ser Ala Ala Ser
                165                 170                 175

Trp Ile Glu Leu Cys Asp Trp Val Pro Ala Leu Leu Ser Gly Thr Thr
            180                 185                 190

Arg Pro Gln Asp Ile Arg Arg Gly Arg Cys Ser Ala Gly His Lys Ser
        195                 200                 205

Leu Trp His Glu Ser Trp Gly Gly Leu Pro Pro Ala Ser Phe Phe Asp
    210                 215                 220

Glu Leu Asp Pro Ile Leu Asn Arg His Leu Pro Ser Pro Leu Phe Thr
225                 230                 235                 240

Asp Thr Trp Thr Ala Asp Ile Pro Val Gly Thr Leu Cys Pro Glu Trp
                245                 250                 255

Ala Gln Arg Leu Gly Leu Pro Glu Ser Val Val Ile Ser Gly Gly Ala
            260                 265                 270

Phe Asp Cys His Met Gly Ala Val Gly Ala Gly Ala Gln Pro Asn Ala
        275                 280                 285

Leu Val Lys Val Ile Gly Thr Ser Thr Cys Asp Ile Leu Ile Ala Asp
    290                 295                 300

Lys Gln Ser Val Gly Glu Arg Ala Val Lys Gly Ile Cys Gly Gln Val
305                 310                 315                 320

Asp Gly Ser Val Val Pro Gly Phe Ile Gly Leu Glu Ala Gly Gln Ser
                325                 330                 335

Ala Phe Gly Asp Ile Tyr Ala Trp Phe Gly Arg Val Leu Gly Trp Pro
            340                 345                 350

Leu Glu Gln Leu Ala Ala Gln His Pro Glu Leu Lys Thr Gln Ile Asn
        355                 360                 365

Ala Ser Gln Lys Gln Leu Leu Pro Ala Leu Thr Glu Ala Trp Ala Lys
```

Asn Pro Ser Leu Asp His Leu Pro Val Val Leu Asp Trp Phe Asn Gly
385                 390                 395                 400

Arg Arg Thr Pro Asn Ala Asn Gln Arg Leu Lys Gly Val Ile Thr Asp
            405                 410                 415

Leu Asn Leu Ala Thr Asp Ala Pro Leu Leu Phe Gly Gly Leu Ile Ala
            420                 425                 430

Ala Thr Ala Phe Gly Ala Arg Ala Ile Met Glu Cys Phe Thr Asp Gln
            435                 440                 445

Gly Ile Ala Val Asn Asn Val Met Ala Leu Gly Gly Ile Ala Arg Lys
450                 455                 460

Asn Gln Val Ile Met Gln Ala Cys Cys Asp Val Leu Asn Arg Pro Leu
465                 470                 475                 480

Gln Ile Val Ala Ser Asp Gln Cys Cys Ala Leu Gly Ala Ala Ile Phe
            485                 490                 495

Ala Ala Val Ala Ala Lys Val His Ala Asp Ile Pro Ser Ala Gln Gln
            500                 505                 510

Lys Met Ala Ser Ala Val Glu Lys Thr Leu Gln Pro Cys Ser Glu Gln
            515                 520                 525

Ala Gln Arg Phe Glu Gln Leu Tyr Arg Arg Tyr Gln Gln Trp Ala Met
            530                 535                 540

Ser Ala Glu Gln His Tyr Leu Pro Thr Ser Ala Pro Gln Ala Ala
545                 550                 555                 560

Gln Ala Val Ala Thr Leu
                565

<210> SEQ ID NO 29
<211> LENGTH: 693
<212> TYPE: DNA
<213> ORGANISM: Escherichia coli

<400> SEQUENCE: 29
atgttagaag atctcaaacg ccaggtatta gaagccaacc tggcgctgcc aaaacacaac      60
ctggtcacgc tcacatgggg caacgtcagc gccgttgatc gcgagcgcgg cgtctttgtg     120
atcaaacctt ccggcgtcga ttacagcgtc atgaccgctg acgatatggt cgtggttagc     180
atcgaaaccg gtgaagtggt tgaaggtacg aaaaagccct cctccgacac gccaactcac     240
cggctgctct atcaggcatt cccctccatt ggcggcattg tgcatacgca ctcgcgccac     300
gccaccatct gggcgcaggc gggtcagtcg attccagcaa ccggcaccac ccacgccgac     360
tatttctacg gcaccattcc ctgtacccgc aaaatgaccg acgcagaaat caacggcgaa     420
tatgagtggg aaaccggtaa cgtcatcgta gaacctttg aaaaacaggg tatcgatgca     480
gcgcaaatgc ccggcgttct ggtccattcc cacggcccgt tgcatgggg caaaaatgcc     540
gaagatgcgg tgcataacgc catcgtgctg gaagaggtcg cttatatggg gatattctgc     600
cgtcagttag cgccgcagtt accggatatg cagcaaacgc tgctggataa acactatctg     660
cgtaagcatg gcgcgaaggc atattacggg cag                                  693

<210> SEQ ID NO 30
<211> LENGTH: 231
<212> TYPE: PRT
<213> ORGANISM: Escherichia coli

<400> SEQUENCE: 30

Met Leu Glu Asp Leu Lys Arg Gln Val Leu Glu Ala Asn Leu Ala Leu

```
              1               5              10              15
            Pro Lys His Asn Leu Val Thr Leu Thr Trp Gly Asn Val Ser Ala Val
                           20                  25                  30

Asp Arg Glu Arg Gly Val Phe Val Ile Lys Pro Ser Gly Val Asp Tyr
                       35                  40                  45

Ser Val Met Thr Ala Asp Asp Met Val Val Ser Ile Glu Thr Gly
             50                  55                  60

Glu Val Val Glu Gly Thr Lys Lys Pro Ser Ser Asp Thr Pro Thr His
             65                  70                  75                  80

Arg Leu Leu Tyr Gln Ala Phe Pro Ser Ile Gly Gly Ile Val His Thr
                           85                  90                  95

His Ser Arg His Ala Thr Ile Trp Ala Gln Ala Gly Gln Ser Ile Pro
                          100                 105                 110

Ala Thr Gly Thr Thr His Ala Asp Tyr Phe Tyr Gly Thr Ile Pro Cys
                          115                 120                 125

Thr Arg Lys Met Thr Asp Ala Glu Ile Asn Gly Glu Tyr Glu Trp Glu
                          130                 135                 140

Thr Gly Asn Val Ile Val Glu Thr Phe Glu Lys Gln Gly Ile Asp Ala
            145                 150                 155                 160

Ala Gln Met Pro Gly Val Leu Val His Ser His Gly Pro Phe Ala Trp
                          165                 170                 175

Gly Lys Asn Ala Glu Asp Ala Val His Asn Ala Ile Val Leu Glu Glu
                          180                 185                 190

Val Ala Tyr Met Gly Ile Phe Cys Arg Gln Leu Ala Pro Gln Leu Pro
                          195                 200                 205

Asp Met Gln Gln Thr Leu Leu Asp Lys His Tyr Leu Arg Lys His Gly
                          210                 215                 220

Ala Lys Ala Tyr Tyr Gly Gln
            225                 230

<210> SEQ ID NO 31
<211> LENGTH: 304
<212> TYPE: DNA
<213> ORGANISM: artificial sequence
<220> FEATURE:
<223> OTHER INFORMATION: mutant promoter

<400> SEQUENCE: 31
gttcgatcaa caacccgaat cctatcgtaa tgatgttttg cccgatcagc ctcaatcgac      60
aattttacgc gtttcgatcg aagcagggac gacaattggc tgggaacggt atacttgaat     120
aaatggtctt cgttatggta ttgatgtttt tggtgcatcg gccccggcga atgatctata     180
tgctcatttc ggcttgaccg cagtcggcat cacgaacaag gtgttggccg cgatcgccgg     240
taagtcggca cgttaaaaaa tagctatgga atataatagc tactaataag ttaggagaat     300
aaac                                                                   304

<210> SEQ ID NO 32
<211> LENGTH: 903
<212> TYPE: DNA
<213> ORGANISM: artificial sequence
<220> FEATURE:
<223> OTHER INFORMATION: chimeric gene construction

<400> SEQUENCE: 32
ccatggcgag ctcgttcgat caacaacccg aatcctatcg taatgatgtt tgcccgatc       60 agcctcaatc gacaatttta cgcgtttcga tcgaagcagg gacgacaatt ggctgggaac     120
```

```
ggtatactgg aataaatggt cttcgttatg gtattgatgt ttttggtgca tcggccccgg     180
cgaatgatct atatgctcat ttcggcttga ccgcagtcgg catcacgaac aaggtgttgg     240
ccgcgatcgc cggtaagtcg gcacgttaaa aaatagctat ggaatataat agctacttaa     300
taagttagga gaataaacgt gacctctgct gtgccatcaa atacgaaaaa aaagctggtg     360
attgcttccg atcacgcagc atttgagttg aaatcaacct tgattacttg gctgaaagag     420
cttggtcatg aggtcgaaga ccttggccct catgaaaacc attcagtcga ttatcccgat     480
tacggttata agctggctgt cgctatcgca gaaaaaaccg ctgatttcgg tattgcttta     540
tgtggctcgg aatcggtat ctcgatcgct gtcaatcgcc atccggctgc ccgttgcgct     600
ttgattacgg ataaccttac cgcccgtttg gcaagagaac ataacaatgc caatgttatc     660
gctatgggtg cgagattgat cggcattgaa accgctaagg attgtatttc agctttcctt     720
gcaacgccgt ttggaggtga acgtcatgtt cgccgtatcg ataaactttc gaatcctcag     780
ttcaatatct agctcgaggc ggcctgaacg tactgcaagt cctgacgtca ctgtgcagtc     840
cgttggcccg gttatcggta gcgataccgg gcattttttt aaggaacgat cgatagcggc     900
cgc                                                                  903

<210> SEQ ID NO 33
<211> LENGTH: 6715
<212> TYPE: DNA
<213> ORGANISM: artificial sequence
<220> FEATURE:
<223> OTHER INFORMATION: constructed plasmid

<400> SEQUENCE: 33
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcggggctgg cttaactatg cggcatcaga gcagattgta ctgagagtgc     180
accatatgcg gtgtgaaata ccgcacagat gcgtaaggag aaaataccgc atcaggcgcc     240
attcgccatt caggctgcgc aactgttggg aagggcgatc ggtgcgggcc tcttcgctat     300
tacgacagct gtctcttata cacatctcaa ccatcatcga tgaattttct cggggatttt     360
gagtcagcat tacaggttat aaaagcgatc gcaccggatg tcattttccg tcagatgcct     420
tgggaagtga atacgccgga acctttccag acgcagcatc tcaattttgc tcgcctgtgc     480
tatgtccctt attatggctt gaacattctg gaaaaattga cagcggaaga aaacgagcaa     540
gatttttctg ctgaccagta ttttcatcgt atgtgttggc ggatgtattg cgagaatgag     600
ccactgtatc agcgcatgaa agaaaaatca ttgcgcggcg gtgataatat cgtggtgagc     660
ggtcatccca gcttgaccg tctatgggaa tcccgcaaaa atccggaatg gccgatcaaa     720
tcggaaggtg agaagaaatt ccgtctgata tgggcgcctc atcacaccat gggaatggt     780 tggcttgatt ttggtatttt cccgcagact ttcggcgata tgttgcaatg gcagaagat     840 gcgcaagata tcgaatttgt tttgcggcca catcccttgc tgtttaattc cctgttattt     900
tataagctat ttaatgagca gcaggtcgag caattcaaga aattatggaa ccgtttgccg     960
aataccgctt tgagtgaagg tggggattat ggttctttat agcggcttc tgatggaatg    1020 attaccgagg gagtcagctt ccttgctgaa tatcagatat tccatgataa accgttgatc    1080
tttttggata gccaacgtca tcgtggattt aatgcagtgg gtgaaaaaat tatgcgtggc    1140
acctataatg caaccactat tcaggcggca cgggaaattg tcgattctta tcgtcaaaaa    1200
```

```
gggaatgacc ccttggccga tattcgaaaa gaaaattttg atatgatgat gccttggccg      1260
gggaaagcgg ctgaacggat tgtggatgat attcaggcga atattgcctt ataaaacctc      1320
aatccctgta attttgattt aataggccgg agaagattgg cgcgccggtc tttagcaagg      1380
ctgtcagatg atatctggca gccttgtagg atattttgt gctgaatagc gcagcttatg       1440
ggaagaaatc gggattaaac agatggccgt ttgaaatcct ctctttccaa aaagagatac      1500
cgtttaactc cgcccgaata attttcgat gtccttatgg cctagtttaa cccatgtcgg       1560
gcgaccatga ttacattggc cgctatgggg cgtgatttcc atttcccgca gcaaagcgtt      1620
catttcagcg attgaaagta aacgacccgc tctgactgat ccgtggcagg ccatggtcgc      1680
aacaatatgg tcgaattttt cctttagcag taagctttga tcataggcgg cgatttcggc      1740
cgcaaggtct tttatcatgg ccttgacttc gcaattaccg agcatcgcag ggtcgcccg       1800 aaccaaaata gcttcatggc cgaagcgttc ggtttcaagc cccattgctg cgaattcatc      1860
ctgcctttgt tcgaacagat cgcaagagac ctcatccatt tcgacaacat ctggcataag     1920
caatctttgg ctagtgactt ggccgttttg caatgctcgc cgcatccgtt ccataaccag      1980
tctttcatgt gcggcatgtt gatcgacaat gaccaatcca tctttggatt cggctataat     2040
ataggtggcc gcgatttggc ctcttgctag tcccagtggg aaatcgcttt gttctgaact     2100
gtctgtcgcg ctattgcgtc ccataggcgg caagggtgat tttgttgcag cactccatag     2160
gtcagaggct gtgccttggg gcgttgggat tgaagtagct ttgggtgctt ctattgtgcg     2220
acttttgaaa agaaggcctg aatctgaaag ggattgtctt gattcatggc taggcacggc     2280
ttttgaaggc gcagccagct cgctgctttt ttgccatttt cccatggctt gaacatcagg     2340
ccggccgctt gtatcagaca taaaaaagcc gccctgtctt gcgacagtga cggcttgttt      2400
tatatccgct cttatttatc gcgtggcggg ggtgccataa attctgcacc gataggattg      2460
gggatattct tggccagaat agcatcaatc tgtttcagat cttcatccga tatctgccag     2520
ccaaaaactt catcaatacc gtcgatctgt tccggcttgc gagcgcccca aagtgctaaa      2580
gtgggccctt gctccaacat ccagcggata gccaaagcca acaccgattt attgtaatgc      2640
tctttggcga gtttcttcag ttcttcaacc gcggccagat aatgttcaaa gcgcggtttc      2700
tggaatttcg ggtctgtttt ccgtaaatca tcgcctgtaa aggcacgatc cgccgtcatt      2760
ctgccagaaa gtaaaccacg gcaaagcgca ccatagccta aaacgaccag atcgtttttc      2820
ttggcatagg gcaggatgtc tttgtctatt tcgcgttcaa acagattata aggcgactgc      2880
gaaacggcca gctcggcata tttcttgaac tcgtccatct gctgaacgga ataattggaa      2940
acgccgatag aacggatttt gccttctttt ctgagggctt ccaatattgt tgcggtttct      3000
tcaatcggaa ccagcggatc cggccaatgc acctgataaa ggtcgatata atcagtgcca      3060
aggcggcgca gagaatcttc gatttctttt ttgatacggc tggctgaact gttacggcgc      3120
atcgattggt cggggttaa agtccaatca aggccgactt tggtcgcaat aatcaaatta      3180
tcgcgttgac ctttgatggc tttaccaacg acttcttcag catggccacg gccataagcc      3240
ggagcggtgt cgatgatatt gataccaaga tcaatcgccc gatgaatggt tttaatggag      3300
gcatcgtcat cagtgccgcc ccacatccag ccaccaatag cccatgtgcc taacgctaca      3360
cgggttgcgg atttatcaat ccctttgatc gaaatcttgt cgaaatgagc gggttttgc       3420 gtagaagtgt tcatatcgaa accttctta aaatcttta gacgagtctc ttttgaact        3480 cagtccgtca atgatctatc cttccttgac gcataaggca attccactgt tgcaatgaat      3540
atattgctta tggtgaaacg ttatcgcttc tcatgcgatt ctatagttag gataaactga      3600
```

```
ttattgttac gtattgagta actggttaat taacttattc aggcgtagca accaggcgtt    3660
taagggcacc aataactgcc ttaaaaaaat tacgccccgc cctgccactc atcgcagtac    3720
tgttgtaatt cattaagcat tctgccgaca tggaagccat cacaaacggc atgatgaacc    3780
tgaatcgcca gcggcatcag caccttgtcg ccttgcgtat aatatttgcc catggtgaaa    3840 acggggggcga agaagttgtc catattggcc acgtttaaat caaaactggt gaaactcacc    3900
cagggattgg ctgagacgaa aaacatattc tcaataaacc ctttagggaa ataggccagg    3960
ttttcaccgt aacacgccac atcttgcgaa tatatgtgta gaaactgccg gaaatcgtcg    4020
tggtattcac tccagagcga tgaaaacgtt tcagtttgct catggaaaac ggtgtaacaa    4080
gggtgaacac tatcccatat caccagctca ccgtctttca ttgccatacg gaattccgga    4140
tgagcattca tcaggcgggc aagaatgtga ataaaggccg gataaaactt gtgcttattt    4200
ttctttacgg tctttaaaaa ggccgtaata tccagctgaa cggtctggtt ataggtacat    4260
tgagcaactg actgaaatgc ctcaaaatgt tctttacgat gccattggga tatatcaacg    4320
gtggtatatc cagtgatttt tttctccatt ttagcttcct tagctcctga aaatctcgat    4380
aactcaaaaa atacgcccgg tagtgatctt atttcattat ggtgaaagtt ggaacctctt    4440
acgtgccgat caacgtctca ttttcgccaa aagttggccc agggcttccc ggtatcaaca    4500
gggacaccag gatttattta ttctgcgaag tgatcttccg tcacgcggcc gcataacttc    4560
gtatagcata cattatacga agttatgcga tcgcaagctt gccaacgact acgcactagc    4620
caacaagagc ttcaggggttg agatgtgtat aagagacagc tgtcttaatg aatcggccaa    4680
cgcgcgggga gaggcggttt gcgtattggg cgctcttccg cttcctcgct cactgactcg    4740
ctgcgctcgg tcgttcggct gcggcgagcg gtatcagctc actcaaaggc ggtaatacgg    4800
ttatccacag aatcagggga taacgcagga agaacatgt gagcaaaagg ccagcaaaag    4860
gccaggaacc gtaaaaaggc cgcgttgctg gcgttttttcc ataggctccg ccccctgac    4920 gagcatcaca aaaatcgacg ctcaagtcag aggtggcgaa acccgacagg actataaaga    4980
taccaggcgt ttccccctgg aagctccctc gtgcgctctc ctgttccgac cctgccgctt    5040
accggatacc tgtccgcctt tctcccttcg ggaagcgtgg cgctttctca tagctcacgc    5100
tgtaggtatc tcagttcggt gtaggtcgtt cgctccaagc tgggctgtgt gcacgaaccc    5160
cccgttcagc ccgaccgctg cgccttatcc ggtaactatc gtcttgagtc caacccggta    5220
agacacgact tatcgccact ggcagcagcc actggtaaca ggattagcag agcgaggtat    5280
gtaggcggtg ctacagagtt cttgaagtgg tggcctaact acggctacac tagaaggaca    5340
gtatttggta tctgcgctct gctgaagcca gttaccttcg gaaaaagagt tggtagctct    5400
tgatccggca aacaaaccac cgctggtagc ggtggttttt ttgtttgcaa gcagcagatt    5460
acgcgcagaa aaaaggatc tcaagaagat cctttgatct tttctacggg gtctgacgct    5520
cagtggaacg aaaactcacg ttaagggatt ttggtcatga gattatcaaa aaggatcttc    5580
acctagatcc ttttaaatta aaaatgaagt tttaaatcaa tctaaagtat atatgagtaa    5640
acttggtctg acagttacca atgcttaatc agtgaggcac ctatctcagc gatctgtcta    5700
tttcgttcat ccatagttgc ctgactcccc gtcgtgtaga taactacgat acgggagggc    5760
ttaccatctg gccccagtgc tgcaatgata ccgcgagacc cacgctcacc ggctccagat    5820
ttatcagcaa taaccagcc agccggaagg gccgagcgca gaagtggtcc tgcaactttta    5880 tccgcctcca tccagtctat taattgttgc cgggaagcta gagtaagtag ttcgccagtt    5940
```

```
aatagtttgc gcaacgttgt tgccattgct acaggcatcg tggtgtcacg ctcgtcgttt    6000
ggtatggctt cattcagctc cggttcccaa cgatcaaggc gagttacatg atcccccatg    6060
ttgtgcaaaa aagcggttag ctccttcggt cctccgatcg ttgtcagaag taagttggcc    6120
gcagtgttat cactcatggt tatggcagca ctgcataatt ctcttactgt catgccatcc    6180
gtaagatgct tttctgtgac tggtgagtac tcaaccaagt cattctgaga atagtgtatg    6240
cggcgaccga gttgctcttg cccggcgtca atacgggata ataccgcgcc acatagcaga    6300
actttaaaag tgctcatcat tggaaaacgt tcttcgggc gaaaactctc aaggatctta    6360
ccgctgttga gatccagttc gatgtaaccc actcgtgcac ccaactgatc ttcagcatct    6420
tttactttca ccagcgtttc tgggtgagca aaaacaggaa ggcaaaatgc cgcaaaaaag    6480
ggaataaggg cgacacggaa atgttgaata ctcatactct tcctttttca atattattga    6540
agcatttatc agggttattg tctcatgagc ggatacatat ttgaatgtat ttagaaaaat    6600
aaacaaatag gggttccgcg cacatttccc cgaaaagtgc cacctgacgt ctaagaaacc    6660
attattatca tgacattaac ctataaaaat aggcgtatca cgaggccctt tcgtc          6715

<210> SEQ ID NO 34
<211> LENGTH: 22
<212> TYPE: DNA
<213> ORGANISM: artificial sequence
<220> FEATURE:
<223> OTHER INFORMATION: primer

<400> SEQUENCE: 34
cgtcatcgtg gatttaatgc ag                                              22

<210> SEQ ID NO 35
<211> LENGTH: 19
<212> TYPE: DNA
<213> ORGANISM: artificial sequence
<220> FEATURE:
<223> OTHER INFORMATION: primer

<400> SEQUENCE: 35
cttgaaaccg aacgcttcg                                                  19

<210> SEQ ID NO 36
<211> LENGTH: 12704
<212> TYPE: DNA
<213> ORGANISM: artificial sequence
<220> FEATURE:
<223> OTHER INFORMATION: constructed plasmid

<400> SEQUENCE: 36
ctagtgttcg atcaacaacc cgaatcctat cgtaatgatg ttttgcccga tcagcctcaa    60
tcgacaattt tacgcgtttc gatcgaagca gggacgacaa ttggctggga acggtatact    120
ggaataaatg gtcttcgtta tggtattgat gttttggtg catcggcccc ggcgaatgat    180
ctatatgctc atttcggctt gaccgcagtc ggcatcacga acaaggtgtt ggccgcgatc    240
gccggtaagt cggcacgtta aaaaatagct atggaatata atagctacta ataagttagg    300
agaataaaca tgacggacaa attgacctcc cttcgtcagt acaccaccgt agtggccgac    360
actggggaca tcgcggcaat gaagctgtat caaccgcagg atgccacaac caacccttct    420
ctcattctta acgcagcgca gattccggaa taccgtaagt tgattgatga tgctgtcgcc    480
tgggcgaaac agcagagcaa cgatcgcgcg cagcagatcg tggacgcgac cgacaaactg    540
gcagtaaata ttggtctgga aatcctgaaa ctggttccgg gccgtatctc aactgaagtt    600
```

```
gatgcgcgtc tttcctatga caccgaagcg tcaattgcga aagcaaaacg cctgatcaaa    660
ctctacaacg atgctggtat tagcaacgat cgtattctga tcaaactggc ttctacctgg    720
cagggtatcc gtgctgcaga acagctggaa aaagaaggca tcaactgtaa cctgaccctg    780
ctgttctcct tcgctcaggc tcgtgcttgt gcggaagcgg gcgtgttcct gatctcgccg    840
tttgttggcc gtattcttga ctggtacaaa gcgaataccg ataagaaaga gtacgctccg    900
gcagaagatc cgggcgtggt ttctgtatct gaaatctacc agtactacaa agagcacggt    960
tatgaaaccg tggttatggg cgcaagcttc cgtaacatcg gcgaaattct ggaactggca   1020
ggctgcgacc gtctgaccat cgcaccggca ctgctgaaag agctggcgga gagcgaaggg   1080
gctatcgaac gtaaactgtc ttacaccggc gaagtgaaag cgcgtccggc gcgtatcact   1140
gagtccgagt tcctgtggca gcacaaccag gatccaatgg cagtagataa actggcggaa   1200
ggtatccgta agtttgctat tgaccaggaa aaactggaaa aaatgatcgg cgatctgctg   1260
taatctagac gatctggagt caaaatgtcc tcacgtaaag agcttgccaa tgctattcgt   1320
gcgctgagca tggacgcagt acagaaagcc aaatccggtc acccgggggc ccctatgggt   1380
atggctgaca ttgccgaagt cctgtggcgt gatttcctga acacaaccc gcagaatccg    1440
tcctgggctg accgtgaccg cttcgtgctg tccaacggcc acggctccat gctgatctac   1500
agcctgctgc acctcaccgg ttacgatctg ccgatggaag aactgaaaaa cttccgtcag   1560
ctgcactcta aaactccggg tcacccggaa gtgggttaca ccgctggtgt ggaaaccacc   1620
accggtccgc tgggtcaggg tattgccaac gcagtcggta tggcgattgc agaaaaaacg   1680
ctggcggcgc agtttaaccg tccgggccac gacattgtcg accactacac ctacgccttc   1740
atgggcgacg gctgcatgat ggaaggcatc tcccacgaag tttgctctct ggcgggtacg   1800
ctgaagctgg gtaaactgat tgcattctac gatgacaacg gtatttctat cgatggtcac   1860
gttgaaggct ggttcaccga cgacaccgca atgcgtttcg aagcttacgg ctggcacgtt   1920
attcgcgaca tcgacggtca tgacgcggca tctatcaaac gcgcagtaga agaagcgcgc   1980
gcagtgactg acaaaccttc cctgctgatg tgcaaaacca tcatcggttt cggttccccg   2040
aacaaagccg gtacccacga ctcccacggt gcgccgctgg gcgacgctga aattgccctg   2100
acccgcgaac aactgggctg gaaatatgcg ccgttcgaaa tcccgtctga aatctatgct   2160
cagtgggatg cgaaagaagc aggccaggcg aaagaatccg catggaacga gaaattcgct   2220
gcttacgcga aagcttatcc gcaggaagcc gctgaattta cccgccgtat gaaaggcgaa   2280
atgccgtctg acttcgacgc taaagcgaaa gagttcatcg ctaaactgca ggctaatccg   2340
gcgaaaatcg ccagccgtaa agcgtctcag aatgctatcg aagcgttcgg tccgctgttg   2400
ccggaattcc tcggcggttc tgctgacctg gcgccgtcta acctgaccct gtggtctggt   2460
tctaaagcaa tcaacgaaga tgctgcgggt aactacatcc actacggtgt tcgcgagttc   2520
ggtatgaccg cgattgctaa cggtatctcc ctgcacggtg gcttcctgcc gtacacctcc   2580
accttcctga tgttcgtgga atacgcacgt aacgccgtac gtatggctgc gctgatgaaa   2640
cagcgtcagg tgatggttta cacccacgac tccatcggtc tgggcgaaga cgggccgact   2700
caccagccgg ttgagcaggt cgcttctctg cgcgtaaccc cgaacatgtc tacatggcgt   2760
ccgtgtgacc aggttgaatc cgcggtcgcg tggaaatacg tgttgagcg tcaggacggc   2820
ccgaccgcac tgatcctctc ccgtcagaac ctggcgcagc aggaacgaac tgaagagcaa   2880
ctggcaaaca tcgcgcgcgg tggttatgtg ctgaaagact gcgccggtca gccggaactg   2940
```

-continued

```
attttcatcg ctaccggttc agaagttgaa ctggctgttg ctgcctacga aaaactgact    3000
gccgaaggcg tgaaagcgcg cgtggtgtcc atgtcgtcta ccgacgcatt tgacaagcag    3060
gatgctgctt accgtgaatc cgtactgccg aaagcggtta ctgcacgcgt tgctgtagaa    3120
gcgggtattg ctgactactg gtacaagtat gttggcctga acggtgctat cgtcggtatg    3180
accaccttcg gtgaatctgc tccggcagag ctgctgtttg aagagttcgg cttcactgtt    3240
gataacgttg ttgcgaaagc aaaagaactg ctgtaattag catttcgggt aaaaaaggtc    3300
gcttcggcga ccttttttat taccttgata atgtccgttt gcgcggcgcg ccccagttac    3360
tcaatacgta acaataatca gtttatccta actatagaat cgcatgagaa gcgataacgt    3420
ttcaccataa gcaatatatt cattgcaaca gtggaattgc cttatgcgtc aaggaaggat    3480
agatcattga cggactgagt tcaaaaagag actcgtctaa aagattttaa gaaaggtttc    3540
gatatgacct ctgctgtgcc atcaaatacg aaaaaaaagc tggtgattgc ttccgatcac    3600
gcagcatttg agttgaaatc aaccttgatt acttggctga aagagcttgg tcatgaggtc    3660
gaagaccttg gccctcatga aaaccattca gtcgattatc ccgattacgg ttataagctg    3720
gctgtcgcta tcgcagaaaa aaccgctgat ttcggtattg cttttatgtgg ctcgggaatc    3780 ggtatctcga tcgctgtcaa tcgccatccg gctgcccgtt gcgctttgat tacggataac    3840
cttaccgccc gtttggcaag agaacataac aatgccaatg ttatcgctat gggtgcgaga    3900
ttgatcggca ttgaaaccgc taaggattgt atttcagctt ccttgcaac gccgtttgga    3960 ggtgaacgtc atgttcgccg tatcgataaa cttttcgaatc ctcagttcaa tatctagata    4020
agttaggaga ataaacatga gtaaattacc cctgattgct ccctctatcc tttcggcgga    4080
ttttgcccat ttgggagatg aggtcgcggc gatagatcag gccggtgccg attggatcca    4140
tattgatgtg atggatggcc atttcgtgcc gaatatcacc ataggcccca tggttgtgaa    4200
ggctttgcgt ccctatagcc aaaagccttt tgatgtccat ttgatgattg cgcctgtcga    4260
tcaatatatc gaggcttttt ctgaagcggg tgctgatatt atcagtttcc atcccgaagc    4320
gggcgcgcat ccccatcgca ctattcagca tatcaaatca ttgggcaaaa aagcgggatt    4380 agttttaat ccggcgaccc ctttaagctg gcttgattat ctaatggatg atcttgatct    4440
gattatggtg atgagcgtta accccggttt tggcggccaa aaatttatca aaacccaatt    4500
agaaaagatt aaagatatcc gtcaaagaat taccgcctct gggcgggata tccgcttgga    4560
agtggatggc ggaattgatg ccacgactgc accgcttgcc gtcgaagccg gtgccgatgt    4620
tttggtcgcg ggaacggcca gctttaaagg cggcgcaaca tgttacaccg ataatatcag    4680
gatattgcgt aaatcatgat taattaactc gaggcggcct gaacgtactg caagtcctga    4740
cgtcactgtg cagtccgttg gcccggttat cggtagcgat accgggcatt tttttaagga    4800
acgatcgata gaattcgcgg ccggcccggc aagacgtgat atggaaccgg aatttgctcc    4860
ggcattcctg cgcaaagata gctaatatct ttcatatttt gtatcgaaaa aggagggtct    4920
ttaaagatcc tccttttttt tgcataaaaa gaaggccata gaacaaacag tgataaagac    4980
agtctcaaac tgtcttttta tagaaaatac cagaatattg tatctggggg aggatgcatg    5040
gtcttaatcc ggaatacccc ggtcatgcac aggatgttag agcttttgcc tttatggcaa    5100
aataaaccat ggctcgggaa tatctgcgct ttgatttttg taggatgtgc cttccttgtc    5160
cgtagtatta tttgggcattt tttaccggca ggttatcctt tcgtgacctt tatgccgaca    5220
atgcttgtgg ttactttcct ctttgggaca agaccgggta ttatcgcggc tattcttagc    5280
ttgatggttg cgccttattt tatcgaagaa ggaagccgat ttaacggtgt attggtctgg    5340
```

```
tttctttgcc tgctagaaac agtcactgat atgggattgg tgattgcgct acagcaaggt   5400
aattaccgcc tccagaaaaa gcgtgcctat aatcagatgc tggctgaacg caatgagttg   5460
ctgtttcatg aattacagca tcgcatttca ataacttac aggttattgc gtcattattg    5520
cggatgcaaa gccgcagcat caccgatgaa aaagccaagg aagctattga tgcctctgtt   5580
cgtcggattc atatgatcgg tgaattacag cgggcgcttt atattaaaaa cgggaatcag   5640
cttggggcaa aattgatcct tgatcgcttg atcaaagagg tcattgcgtc cagtaatctc   5700
ccgaacatcc gctataaaat agaagctgaa gacctgatct taccgtcaga tatggcaatc   5760
cctttagcgc ttgtatctgc tgaatccgtt tcaaacgcgt tagagcatgg ctttaaaggc   5820
gatcataaag acgcgtttat tgaaattaag cttcaaaaaa ttagcgggca aatcgaactt   5880
accatttcca ataatggcaa acctcttccc caaggctttt ccttgaaaa ggtcgatagc    5940 ttaggcctga aaattgcggc tatgtttgcc cgacaattca aggaaaatt caccttaagt    6000 aatcagccta accgttatgt ggtttctagc cttattttgc cttgcggtta ggcggccgcc   6060
taattccgga tgagcattca tcaggcgggc aagaatgtga ataaaggccg ataaaacttt   6120 gtgcttatt ttcttacgg tctttaaaaa ggccgtaata tccagctgaa cggtctggtt      6180
ataggtacat tgagcaactg actgaaatgc ctcaaaatgt tctttacgat gccattggga   6240
tatatcaacg gtggtatatc cagtgatttt tttctccatt ttagcttcct tagctcctga   6300
aaatctcgat aactcaaaaa atacgcccgg tagtgatctt atttcattat ggtgaaagtt   6360
ggaacctctt acgtgccgat caacgtctca ttttcgccaa aagttggccc agggcttccc   6420
ggtatcaaca gggacaccag gatttattta ttctgcgaag tgatcttccg tcacaggtat   6480
ttattcggcg caaagtgcgt cgggtgatgc tgccaactta ctgatttagt gtatgatggt   6540 gttttgagg tgctccagtg gcttctgttt ctatcagctg tccctcctgt tcagctactg     6600
acggggtggt gcgtaacggc aaaagcaccg ccggacatca gcgctagcgg agtgtatact   6660
ggcttactat gttggcactg atgagggtgt cagtgaagtg cttcatgtgg caggagaaaa   6720
aaggctgcac cggtgcgtca gcagaatatg tgatacagga tatattccgc ttcctcgctc   6780
actgactcgc tacgctcggt cgttcgactg cggcgagcgg aaatggctta cgaacggggc   6840
ggagatttcc tggaagatgc caggaagata cttaacaggg aagtgagagg gccgcggcaa   6900
agccgttttt ccataggctc cgcccccctg acaagcatca cgaaatctga cgctcaaatc   6960
agtggtggcg aaacccgaca ggactataaa gataccaggc gtttccccct ggcggctccc   7020
tcgtgcgctc tcctgttcct gcctttcggt ttaccggtgt cattccgctg ttatggccgc   7080
gtttgtctca ttccacgcct gacactcagt tccgggtagg cagttcgctc caagctggac   7140
tgtatgcacg aaccccccgt tcagtccgac cgctgcgcct tatccggtaa ctatcgtctt   7200
gagtccaacc cggaaagaca tgcaaaagca ccactggcag cagccactgg taattgattt   7260
agaggagtta gtcttgaagt catgcgccgg ttaaggctaa actgaaagga caagttttgg   7320
tgactgcgct cctccaagcc agttaccctcg gttcaaagag ttggtagctc agagaacctt   7380
cgaaaaaccg ccctgcaagg cggttttttc gttttcagag caagagatta gcgcagacc    7440 aaaacgatct caagaagatc atcttattaa tcagataaaa tatttctaga tttcagtgca   7500
atttatctct tcaaatgtag cacctgaagt cagccccata cgatataagt tgtaattctc   7560
atgtttgaca gcttatcatc gatgtgacgg aagatcactt cgcagaataa ataaatcctg   7620
gtgtccctgt tgataccggg aagccctggg ccaacttttg gcgaaaatga gacgttgatc   7680
```

```
ggcacgtaag aggttccaac tttcaccata atgaaataag atcactaccg ggcgtatttt    7740
ttgagttatc gagattttca ggagctaagg aagctaaaat ggagaaaaaa atcactggat    7800
ataccaccgt tgatatatcc caatggcatc gtaaagaaca ttttgaggca tttcagtcag    7860
ttgctcaatg tacctataac cagaccgttc agctggatat tacggccttt ttaaagaccg    7920
taaagaaaaa taagcacaag ttttatccgg cctttattca cattcttgcc cgcctgatga    7980
atgctcatcc ggaattccgt atggcaatga agacggtga gctggtgata tgggatagtg    8040
ttcacccttg ttacaccgtt ttccatgagc aaactgaaac gttttcatcg ctctggagtg    8100
aataccacga cgatttccgg cagtttctac acatatattc gcaagatgtg gcgtgttacg    8160
gtgaaaacct ggcctatttc cctaaagggt ttattgagaa tatgtttttc gtctcagcca    8220
atccctgggt gagtttcacc agttttgatt taaacgtggc caatatggac aacttcttcg    8280
cccccgtttt caccatgggc aaatattata cgcaaggcga caaggtgctg atgccgctgg    8340
cgattcaggt tcatcatgcc gtttgtgatg gcttccatgt cggcagaatg cttaatgaat    8400
tacaacagta ctgcgatgag tggcagggcg gggcgtaatt tttttaaggc agttattggt    8460
gcccttaaac gcctggttgc tacgcctgaa taagtcgacc tttgtagtct tggcctgttg    8520
tgtgcatgag caaatcaatg gcaccacccc ctccttttg agctgaatgg tcataaaatt    8580
tataattatc tatcgtaatt cggaatctat gttcagggtc tcgccattgc ttttgtctg     8640
ctgggtcaag ttccatgcct aaggttttta agacatcaga aagaggtatt gcacgcatgc    8700
tatcagcttt tcttctagct aatgacaggg cttcctctgc tctatctgct cgttttttt    8760
cttccacata tctcgccgct ttgtcagcca gcggctgtat tacggaaagt gccgattttt    8820
gggcttttag gcgttctttt tctgcccatt cttccttatt tgtaaaaatt gagggtggga    8880
tgggtgcctg aatcttggga tctagctgta aagttttgtt gatatttccg taatgtcttt    8940
ggactctttg atgcgttgct tttgaacctt ttacgcctct ggccagccct agaggctcca    9000
tagaagccgc ataatccgtc tggagggcag aaagggcttt tcgaccatca aaccatctcg    9060
atgcgtttaa acggcctgta tcggggtctc taggcaccat aaagccggtt aagtggggtg    9120
ttgtttcatc agcatgtagc tgaagagata caaggttgtt ttctccaaag gtttgttccg    9180
cccattgctg ggtgattgtt ttccagtgtt cgagttttc aggagtggcc tgttttgacc     9240
attctggaga cataccaaag aacagttcta tggcctgcac accgtttttt ctaagaggct    9300
ttcccgtttc tttctgaatt ttattcagca tagatttaac atctgctgat gggtcagtag    9360
agcctttgag tatttcgttt agttcttttc tatctgggtc agcgttttgt gtttcgcggc    9420
ctcgcgtcat atgcaggctc gcggctttaa tcgtgccaac tgttttatgt ttttcaaacc    9480
taaagattgc atagttcggc atgttttaac tgctttaatt tgagaaaaga ccagaggaaa    9540
taatccagcc tatatttctt tccctagtag cgaactggaa ttgttttcc gaaggaaaaa     9600
agcaattccg tagtgagtac tgaatttatt ctgattcgtc ttgcttttgg agcgtctttt    9660
tgcgttctat aactgttgtg aaagctacgc ggtcgccatt gaaaacgaaa ttaggattaa    9720
taaaatacca tccttggcga acatgctttg caatgatttt agcttttct aattcggcta     9780
gacctcttgc aaaggtagct tgagatagtg ccagtttttt ttcttgtgcg ttaagaaagt    9840
cctctaaaac gaatttgtct aaagggacga ggtctttgct gatgcctttg tcttgaagta    9900
tccaaaccag aacgctgaaa gcttttattc cagcggctcc tagttcaaaa gttagcgcga    9960
tattggtgct aaataatttt acaaattctt cactatcaac acgtctgtaa gtcgtcacat   10020
gagtgccttg catctcacca gtggcttgat tgaccagaat gttatcatct cgtcctaatc   10080
```

```
gagataactg aaccctctga cttttaactg gcacaaccat accttcgatg aaaggattct   10140
cgtcatatct gattggctgc tttctcaatt ttgtcgccat atttgataaa cctttaatca   10200
aaaaaaccac attttttgat tatacctatt catcgaatga ggcaaggtct atcaatttta   10260
ccccttttt  tgatagacgg tttaatcaat attgatagac cccttcacag attctgaaaa   10320
tcgacttccc tattttaggg atattttcac gattcccttt cttagttctt cctagtgggg   10380
aaattcgttg aatcctgcct cggaaaaacc atgagaaagc tgttggttat atacacgggc   10440
aaagccaccc tattttagc  tactggggaa agagataagg cagggtattt gtaaaattaa   10500
aaccggattt ttcgctttac ggtttgttta ggcgcaactg tcttttaag  accgcgttta   10560
accatcaaaa gatcgttcca atcttttccg tgtatcatct gttctttagg tgggagccag   10620
ttttcaactt tttttgttgg aaacgcggct ttaatcgctc cgactaatag cgatgctgct   10680
ctttgtccta cagcatccca atcataggca atatggacag aagatgcctt tcaacgatt   10740
tttcggagag ttttagtaag agacgttctt acgccgctgg tgcttaataa ttttacgcca   10800
gctttaattt tttctgggct taaaaagccg actactgaaa tcgcgtctat cgcactttca   10860
gcgatataaa gatcatactt ttcgtcattt tttacattga tgctgccagt aaaatgggct   10920
tcgcgactgc ttcccaaggc taacccttta aaaccactgc ttgttccgcg taattctgcg   10980
ccctgaagtg tatctttatc gtcatacatc aagaaggcta cattaccgcg atcatctgtt   11040
cggatagagt caggaatatt gttaaatgat attcctcggg cagcgttggg tcctggccac   11100
gggtgcgcat gatcgtgctc ctgtcgttga ggacccggct aggctggcgg ggttgcctta   11160
ctggttagca gaatgaatca ccgatacgcg agcgaacgtg aagcgactgc tgctgcaaaa   11220
cgtctgcgac ctgagcaaca acatgaatgg tcttcggttt ccgtgtttcg taaagtctgg   11280
aaacgcggaa gtcccctacg tgctgctgaa gttgcccgca acagagagtg gaaccaaccg   11340
gtgataccac gatactatga ctgagagtca acgccatggg agctccctat cgtctgactc   11400
gcaaggctga acgtgttgac gccttgagca aggccaaagc ggttcttgac gaagccttcc   11460
cagaagctga tccgacagaa aagctgcgca tccagaagct tgcgaagaag ctggaagcaa   11520
aaatcgtccg caccgccatt ctgaaagaag gccggagaat tgacggacgc gatctgaaaa   11580
cagttcgccc gatccgctct caggttggat tcttgccccg cacgcatggt tctgccctgt   11640
ttacgcgtgg tgaaacacag gctttggttt caaccaccct tggaacgcg  gatgctgaac   11700
agatgatcga cggtttaacc ggccttcatt atgaacgctt catgctgcat tacaacttcc   11760
ccccatattc ggtcggtgaa gttggtcgtt ttggtgctcc gggtcgtcgt gaaatcggcc   11820
atggtaaact ggcatggcgt gcgcttcatc cggttttgcc gagcaaggct gatttcccgt   11880
ataccatccg tgttttgtcg gatatcaccg aatctaatgg ttcctcttcc atggcaaccg   11940
tttgcggtgg ctgccttgca ttgatggatg ccggtgttcc cttaacgcgt ccggtttccg   12000
gtatcgccat gggtcttatt ctggaaaaag acggcttcgc tattttgtcc gatatcatgg   12060
gtgatgaaga tcacttgggt gatatggact ttaaggtcgc cggtaccgaa aaaggtatca   12120
ccagcctcca gatggacatc aaggttgctg gcattaccga agaaatcatg cagaaagctt   12180
tggaacaggc taaaggtggc cgtgctcata tcttgggtga atgtccaaa  gcgctgggtg   12240
aagtccgctc cgaaatttct aatttggcac cgcgcattga acaatgagc  gtaccaaaag   12300
acaaaatccg tgatgttatc ggaacgggcg gaaaagttat ccgtgaaatc gtggcgacca   12360
caggtgccaa ggtcgatatc gaagatgacg gcacggttcg tctgtcttct tctgatccgg   12420
```

```
ccaatattga agcagcccgt gaatggatca atggtattgt tgaagaaccg gaagtaggca    12480
aaatctataa cggtaaagtc gtcaatatcg ttgatttcgg tgccttcgta aacttcatgg    12540
gtggccgtga cggcttggta catgtttcgg aaatcaagaa cgaacgtgtc aacaaggtca    12600
gcgatgtcct gtccgaaggt caggaagtca aagtcaaggt tcttgaaatt gacaaccgtg    12660
gcaaggttcg cctgtctatg cgtgttgtcg atcaggaaac cgga                     12704
```

<210> SEQ ID NO 37
<211> LENGTH: 1318
<212> TYPE: DNA
<213> ORGANISM: artificial sequence
<220> FEATURE:
<223> OTHER INFORMATION: constructed fragment for integration into
      Z. m pnp gene

<400> SEQUENCE: 37

```
cctatcgtct gactcgcaag gctgaacgtg ttgacgcctt gagcaaggcc aaagcggttc      60
ttgacgaagc cttcccagaa gctgatccga cagaaaagct cgcatccag aagcttgcga      120 agaagctgga agcaaaaatc gtccgcaccg ccattctgaa agaaggccgg agaattgacg     180
gacgcgatct gaaaacagtt cgcccgatcc gctctcaggt tggattcttg ccccgcacgc    240
atggttctgc cctgtttacg cgtggtgaaa cacaggcttt ggtttcaacc acccttggaa    300
cggcggatgt gaacagatg atcgacggtt taaccggcct tcattatgaa cgcttcatgc     360
tgcattacaa cttcccccca tattcggtcg gtgaagttgg tcgttttggt gctccgggtc    420
gtcgtgaaat cggccatggt aaactggcat ggcgtgcgct tcatccggtt ttgccgagca    480
aggctgattt cccgtatacc atccgtgttt tgtcggatat caccgaatct aatggttcct    540
cttccatggc aaccgtttgc ggtggctgcc ttgcattgat ggatgccggt gttcccttaa    600
cgcgtccggt ttccggtatc gccatgggtc ttattctgga aaaagacggc ttcgctattt    660
tgtccgatat catgggtgat gaagatcact gggtgatat ggactttaag gtcgccggta    720
ccgaaaaagg tatcaccagc ctccagatgg acatcaaggt tgctggcatt accgaagaaa    780
tcatgcagaa agctttggaa caggctaaag gtggccgtgc tcatatcttg ggtgaaatgt    840
ccaaagcgct gggtgaagtc cgctccgaaa tttctaattt ggcaccgcgc attgaaacaa    900
tgagcgtacc aaaagacaaa atccgtgatg ttatcggaac gggcggaaaa gttatccgtg    960
aaatcgtggc gaccacaggt gccaaggtcg atatcgaaga tgacggcacg gttcgtctgt    1020
cttcttctga tccggccaat attgaagcag cccgtgaatg gatcaatggt attgttgaag    1080
aaccggaagt aggcaaaatc tataacggta aagtcgtcaa tatcgttgat tcggtgcct     1140 tcgtaaactt catgggtggc cgtgacggct tggtacatgt tcggaaatc aagaacgaac    1200 gtgtcaacaa ggtcagcgat gtcctgtccg aaggtcagga agtcaaagtc aaggttcttg    1260
aaattgacaa ccgtggcaag gttcgcctgt ctatgcgtgt tgtcgatcag gaaaccgg     1318
```

<210> SEQ ID NO 38
<211> LENGTH: 1225
<212> TYPE: DNA
<213> ORGANISM: artificial sequence
<220> FEATURE:
<223> OTHER INFORMATION: constructed fragment for integration into the
      Z. m pnp gene

<400> SEQUENCE: 38

```
cggcaagacg tgatatggaa ccggaatttg ctccggcatt cctgcgcaaa gatagctaat      60
atctttcata ttttgtatcg aaaaaggagg gtctttaaag atcctccttt tttttgcata    120
```

```
aaaagaaggc catagaacaa acagtgataa agacagtctc aaactgtctt tttatagaaa    180
ataccagaat attgtatctg ggggaggatg catggtctta atccggaata ccccggtcat    240
gcacaggatg ttagagcttt tgcctttatg gcaaaataaa ccatggctcg ggaatatctg    300
cgctttgatt tttgtaggat gtgccttcct tgtccgtagt attattgggc attttttacc    360
ggcaggttat cctttcgtga cctttatgcc gacaatgctt gtggttactt tcctctttgg    420
gacaagaccg ggtattatcg cggctattct tagcttgatg gttgcgcctt attttatcga    480
agaaggaagc cgatttaacg gtgtattggt ctggtttctt tgcctgctag aaacagtcac    540
tgatatggga ttggtgattg cgctacagca aggtaattac cgcctccaga aaaagcgtgc    600
ctataatcag atgctggctg aacgcaatga gttgctgttt catgaattac agcatcgcat    660
ttcaaataac ttacaggtta ttgcgtcatt attgcggatg caaagccgca gcatcaccga    720
tgaaaaagcc aaggaagcta ttgatgcctc tgttcgtcgg attcatatga tcggtgaatt    780
acagcgggcg cttatatta aaaacgggaa tcagcttggg gcaaaattga tccttgatcg    840
cttgatcaaa gaggtcattg cgtccagtaa tctcccgaac atccgctata aaatagaagc    900
tgaagacctg atcttaccgt cagatatggc aatccctta gcgcttgtat ctgctgaatc    960
cgtttcaaac gcgttagagc atggctttaa aggcgatcat aaagacgcgt ttattgaaat   1020
taagcttcaa aaaattagcg ggcaaatcga acttaccatt tccataatg gcaaacctct   1080 tccccaaggc ttttcccttg aaaaggtcga tagcttaggc ctgaaaattg cggctatgtt   1140
tgcccgacaa ttcaaaggaa aattcaccct aagtaatcag cctaaccgtt atgtggtttc   1200
tagccttatt ttgccttgcg gttag                                         1225

<210> SEQ ID NO 39
<211> LENGTH: 38
<212> TYPE: DNA
<213> ORGANISM: artificial sequence
<220> FEATURE:
<223> OTHER INFORMATION: primer

<400> SEQUENCE: 39
cgccatggga gctccctatc gtctgactcg caaggctg                             38

<210> SEQ ID NO 40
<211> LENGTH: 40
<212> TYPE: DNA
<213> ORGANISM: artificial sequence
<220> FEATURE:
<223> OTHER INFORMATION: primer

<400> SEQUENCE: 40
gggttgttga tcgaacgagc gcgatcgcaa gcttgccaac                           40

<210> SEQ ID NO 41
<211> LENGTH: 40
<212> TYPE: DNA
<213> ORGANISM: artificial sequence
<220> FEATURE:
<223> OTHER INFORMATION: primer

<400> SEQUENCE: 41
gttggcaagc ttgcgatcgc gctcgttcga tcaacaaccc                           40

<210> SEQ ID NO 42
<211> LENGTH: 39
<212> TYPE: DNA
```

<213> ORGANISM: artificial sequence
<220> FEATURE:
<223> OTHER INFORMATION: primer

<400> SEQUENCE: 42
catcttacta ctagttcctt aaaaaaatgc ccggtatcg                    39

<210> SEQ ID NO 43
<211> LENGTH: 2340
<212> TYPE: DNA
<213> ORGANISM: artificial sequence
<220> FEATURE:
<223> OTHER INFORMATION: constructed fragment

<400> SEQUENCE: 43

| | | | | | |
|---|---|---|---|---|---|
| gcgccatggg | agctccctat | cgtctgactc | gcaaggctga | acgtgttgac | gccttgagca | 60 |
| aggccaaagc | ggttcttgac | gaagccttcc | cagaagctga | tccgacagaa | aagctgcgca | 120 |
| tccagaagct | tgcgaagaag | ctggaagcaa | aaatcgtccg | caccgccatt | ctgaaagaag | 180 |
| gccggagaat | tgacggacgc | gatctgaaaa | cagttcgccc | gatccgctct | caggttggat | 240 |
| tcttgccccg | cacgcatggt | tctgccctgt | ttacgcgtgg | tgaaacacag | gctttggttt | 300 |
| caaccaccct | tggaacggcg | gatgctgaac | agatgatcga | cggtttaacc | ggccttcatt | 360 |
| atgaacgctt | catgctgcat | tacaacttcc | ccccatattc | ggtcggtgaa | gttggtcgtt | 420 |
| ttggtgctcc | gggtcgtcgt | gaaatcggcc | atggtaaact | ggcatggcgt | gcgcttcatc | 480 |
| cggttttgcc | gagcaaggct | gatttcccgt | ataccatccg | tgttttgtcg | gatatcaccg | 540 |
| aatctaatgg | ttcctcttcc | atggcaaccg | tttgcggtgg | ctgccttgca | ttgatggatg | 600 |
| ccggtgttcc | cttaacgcgt | ccggtttccg | gtatcgccat | gggtcttatt | ctggaaaaag | 660 |
| acggcttcgc | tattttgtcc | gatatcatgg | gtgatgaaga | tcacttgggt | gatatggact | 720 |
| taaggtcgc | cggtaccgaa | aaaggtatca | ccagcctcca | gatggacatc | aaggttgctg | 780 |
| gcattaccga | agaaatcatg | cagaaagctt | tggaacaggc | taaaggtggc | cgtgctcata | 840 |
| tcttgggtga | aatgtccaaa | gcgctgggtg | aagtccgctc | gaaatttct | aatttggcac | 900 |
| cgcgcattga | acaatgagc | gtaccaaaag | acaaaatccg | tgatgttatc | ggaacgggcg | 960 |
| gaaaagttat | ccgtgaaatc | gtggcgacca | caggtgccaa | ggtcgatatc | gaagatgacg | 1020 |
| gcacggttcg | tctgtcttct | ctgatccgg | ccaatattga | agcagcccgt | gaatggatca | 1080 |
| atggtattgt | tgaagaaccg | gaagtaggca | aaatctataa | cggtaaagtc | gtcaatatcg | 1140 |
| ttgatttcgg | tgccttcgta | aacttcatgg | gtggccgtga | cggcttggta | catgtttcgg | 1200 |
| aaatcaagaa | cgaacgtgtc | aacaaggtca | gcgatgtcct | gtccgaaggt | caggaagtca | 1260 |
| aagtcaaggt | tcttgaaatt | gacaaccgtg | gcaaggttcg | cctgtctatg | cgtgttgtcg | 1320 |
| atcaggaaac | cggcgcagag | ctggatgata | accgtccgcc | acgtgagaac | gcagaacctg | 1380 |
| tctcttatac | acatctcaac | cctgaagctc | ttgttggcta | gtgcgtagtc | gttggcaagc | 1440 |
| ttgcgatcgc | gctcgttcga | tcaacaaccc | gaatcctatc | gtaatgatgt | tttgcccgat | 1500 |
| cagcctcaat | cgacaatttt | acgcgtttcg | atcgaagcag | ggacgacaat | tggctgggaa | 1560 |
| cggtatactg | gaataaatgg | tcttcgttat | ggtattgatg | ttttggtgc | atcggccccg | 1620 |
| gcgaatgatc | tatatgctca | tttcggcttg | accgcagtcg | gcatcacgaa | caaggtgttg | 1680 |
| gccgcgatcg | ccggtaagtc | ggcacgttaa | aaaatagcta | tggaatataa | tagctactta | 1740 |
| ataagttagg | agaataaacg | tgacctctgc | tgtgccatca | aatacgaaaa | aaagctggt | 1800 |
| gattgcttcc | gatcacgcag | catttgagtt | gaaatcaacc | ttgattactt | ggctgaaaga | 1860 |

```
gcttggtcat gaggtcgaag accttggccc tcatgaaaac cattcagtcg attatcccga   1920
ttacggttat aagctggctg tcgctatcgc agaaaaaacc gctgatttcg gtattgcttt   1980
atgtggctcg ggaatcggta tctcgatcgc tgtcaatcgc catccggctg cccgttgcgc   2040
tttgattacg gataacctta ccgcccgttt ggcaagagaa cataacaatg ccaatgttat   2100
cgctatgggt gcgagattga tcggcattga aaccgctaag gattgtattt cagctttcct   2160
tgcaacgccg tttggaggtg aacgtcatgt tcgccgtatc gataaactt tcgaatcctca    2220 gttcaatatc tagctcgagg cggcctgaac gtactgcaag tcctgacgtc actgtgcagt   2280
ccgttggccc ggttatcggt agcgataccg ggcattttt taaggaacta gtagtaagat     2340
```

<210> SEQ ID NO 44
<211> LENGTH: 4434
<212> TYPE: DNA
<213> ORGANISM: artificial sequence
<220> FEATURE:
<223> OTHER INFORMATION: constructed fragment containing Pgap-araBAD
    operon

<400> SEQUENCE: 44

```
actagttcga tcaacaaccc gaatcctatc gtaatgatgt tttgcccgat cagcctcaat     60
cgacaatttt acgcgtttcg atcgaagcag ggacgacaat tggctgggaa cggtatactg    120
gaataaatgg tcttcgttat ggtattgatg tttttggtgc atcggccccg gcgaatgatc    180
tatatgctca tttcggcttg accgcagtcg gcatcacgaa caaggtgttg ccgcgatcg     240 ccggtaagtc ggcacgttaa aaaatagcta tggaatataa tagctactta ataagttagg    300
agaataaaca tggcgattgc aattggcctc gatttggca gtgattctgt gcgagctttg     360
gcggtggact cgctaccgg tgaagagatc gccaccagcg tagagtggta tcccgttgg     420 cagaaagggc aattttgtga tgccccgaat aaccagttcc gtcatcatcc gcgtgactac    480
attgagtcaa tggaagcggc actgaaaacc gtgcttgcag agcttagcgt cgaacagcgc    540
gcagctgtgg tcgggattgg cgttgacagt accggctcga cgcccgcacc gattgatgcc    600
gacggaaacg tgctggcgct gcgcccggag tttgccgaaa acccgaacgc gatgttcgta    660
ttgtggaaag accacactgc ggttgaagaa gcggaagaga ttacccgttt gtgccacgcg    720
ccgggcaacg ttgactactc ccgctacatt ggtggtattt attccagcga atggttctgg    780
gcaaaaatcc tgcatgtgac tcgccaggac agcgccgtgg cgcaatctgc cgcatcgtgg    840
attgagctgt gcgactgggt gccagctctg ctttccggta ccacccgccc gcaggatatt    900
cgtcgcggac gttgcagcgc cgggcataaa tctctgtggc acgaaagctg ggcggcctg     960 ccgccagcca gtttctttga tgagctggac ccgatcctca atcgccattt gccttccccg   1020
ctgttcactg acacttggac tgccgatatt ccggtgggca ccttatgccc ggaatgggcg   1080
cagcgtctcg gcctgcctga aagcgtggtg atttccggcg gcgcgtttga ctgccatatg   1140
ggcgcagttg gcgcaggcgc acagcctaac gcactggtaa aagttatcgg tacttccacc   1200
tgcgacattc tgattgccga caaacagagc gttggcgagc gggcagttaa aggtatttgc   1260
ggtcaggttg atggcagcgt ggtgcctgga tttatcggtc tggaagcagg ccaatcggcg   1320
tttggtgata tctacgcctg gtttggtcgc gtactcggct ggcgctggaa cagcttgcc    1380 gcccagcatc cggaactgaa acgcaaatc aacgccagcc agaaacaact gcttccggcg    1440
ctgaccgaag catgggccaa aaatccgtct ctggatcacc tgccggtggt gctcgactgg   1500
tttaacggcc gccgcacacc gaacgctaac caacgcctga aggggtgat taccgatctt    1560
```

```
aacctcgcta ccgacgctcc gctgctgttc ggcggtttga ttgctgccac cgcctttggc    1620
gcacgcgcaa tcatggagtg ctttaccgat cagggatcg ccgttaataa cgtgatggca     1680
ctgggcggca tcgcgcggaa aaaccaggtc attatgcagg cctgctgcga cgtgctgaat    1740
cgcccgctgc aaattgttgc ctctgaccag tgctgtgcgc tcggtgcggc gattttgct    1800 gccgtcgccg cgaaagtgca cgcagacatc ccatcagctc agcaaaaaat ggccagtgcg    1860
gtagagaaaa ccctgcaacc gtgcagcgag caggcacaac gctttgaaca gctttatcgc    1920
cgctatcagc aatgggcgat gagcgccgaa caacactatc ttccaacttc cgccccggca    1980
caggctgccc aggccgttgc gactctataa ggacacgata atgacgattt ttgataatta    2040
tgaagtgtgg tttgtcattg gcagccagca tctgtatggc ccggaaaccc tgcgtcaggt    2100
cacccaacat gccgagcacg tcgttaatgc gctgaatacg gaagcgaaac tgccctgcaa    2160
actggtgttg aaaccgctgg gcaccacgcc ggatgaaatc accgctattt ccgcgacgc    2220 gaattacgac gatcgttgcg ctggtctggt ggtgtggctg cacaccttct ccccggccaa    2280
aatgtggatc aacggcctga ccatgctcaa caaaccgttg ctgcaattcc acacccagtt    2340
caacgcggcg ctgccgtggg acagtatcga tatggacttt atgaacctga ccagactgc    2400 acatggcggt cgcgagttcg gcttcattgg cgcgcgtatg cgtcagcaac atgccgtggt    2460
taccggtcac tggcaggata acaagcccca tgagcgtatc ggctcctgga tgcgtcaggc    2520
ggtctctaaa caggataccc gtcatctgaa agtctgccga tttggcgata acatgcgtga    2580
agtggcggtc accgatggcg ataaagttgc cgcacagatc aagttcggtt ctccgtcaa    2640 tacctgggcg gttggcgatc tggtgcaggt ggtgaactcc atcagcgacg gcgatgttaa    2700
cgcgctggtc gatgagtacg aaagctgcta ccatgacg cctgccacac aaatccacgg     2760
caaaaaacga cagaacgtgc tggaagcggc gcgtattgag ctggggatga agcgtttcct    2820
ggaacaaggt ggcttccacg cgttcaccac cacctttgaa gatttgcacg gtctgaaaca    2880
gcttcctggt ctggccgtac agcgtctgat gcagcagggt tacggctttg cgggcgaagg    2940
cgactggaaa actgccgccc tgcttcgcat catgaaggtg atgtcaaccg gtctgcaggg    3000
cggcacctcc tttatggagg actacaccta tcacttcgag aaaggtaatg acctggtgct    3060
cggctcccat atgctggaag tctgcccgtc gatcgccgca aagagaaac cgatcctcga    3120 cgttcagcat ctcggtattg gtggtaagga cgatcctgcc cgcctgatct caatacccca    3180
aaccggccca gcgattgtcg ccagcttgat tgatctcggc gatcgttacc gtctactggt    3240
taactgcatc gacacggtga aaacaccgca ctccctgccg aaactgccgg tggcgaatgc    3300
gctgtggaaa gcgcaaccgg atctgccaac tgcttccgaa gcgtggatcc tcgctggtgg    3360
cgcgcaccat accgtcttca gccatgcact gaacctcaac gatatgcgcc aattcgccga    3420
gatgcacgac attgaaatca cggtgattga taacgacaca cgcctgccag cgtttaaaga    3480
cgcgctgcgc tggaacgaag tgtattacgg atttcgtcgc taagtctaga gaaggagtca    3540
acatgttaga agatctcaaa cgccaggtat tagaagccaa cctggcgctg ccaaaacaca    3600
acctggtcac gctcacatgg ggcaacgtca gcgccgttga tcgcgagcgc ggcgtctttg    3660
tgatcaaacc ttccggcgtc gattacagcg tcatgaccgc tgacgatatg gtcgtggtta    3720
gcatcgaaac cggtgaagtg gttgaaggta cgaaaaagcc ctcctccgac acgccaactc    3780
accggctgct ctatcaggca ttcccctcca ttggcggcat tgtgcatacg cactcgcgcc    3840
acgccaccat ctgggcgcag gcgggtcagt cgattccagc aaccggcacc acccacgccg    3900
```

```
actatttcta cggcaccatt ccctgtaccc gcaaaatgac cgacgcagaa atcaacggcg    3960
aatatgagtg ggaaaccggt aacgtcatcg tagaaacctt tgaaaaacag ggtatcgatg    4020
cagcgcaaat gcccggcgtt ctggtccatt cccacggccc gtttgcatgg ggcaaaaatg    4080
ccgaagatgc ggtgcataac gccatcgtgc tggaagaggt cgcttatatg gggatattct    4140
gccgtcagtt agcgccgcag ttaccggata tgcagcaaac gctgctggat aaacactatc    4200
tgcgtaagca tggcgcgaag gcatattacg ggcagtaatg actgtataaa accacagcca    4260
atcaaacgaa accaggctat actcaagcct ggttttttga tggattttca gcgtggcgca    4320
ggcaggtttt atcttaaccc gacactggcg ggacaccccg caagggacag aagtctcctt    4380
ctggctggcg acggacaacg ggccaagctt ggaagggcga attcgcggcc ggcc          4434
```

ENHANCING D-XYLOSE AND L-ARABINOSE UTILIZATION IN ZYMOMONAS CELLS

FIELD OF THE INVENTION

The invention relates to the fields of microbiology and genetic engineering. More specifically, inactivation of a gene in the *Zymomonas* genome improves D-xylose utilization in a *Zymomonas* strain that is engineered for D-xylose utilization and improves both D-xylose and L-arabinose utilization in a *Zymomonas* strain that is engineered for both D-xylose and L-arabinose utilization.

BACKGROUND OF THE INVENTION

Production of ethanol by microorganisms provides an alternative energy source to fossil fuels and is therefore an important area of current research. It is desirable that microorganisms producing ethanol, as well as other useful products, be capable of using D-xylose and L-arabinose as carbon sources since these are the predominant pentose sugars in hydrolyzed lignocellulosic materials, which can provide an abundantly available source of carbon substrate for biocatalysts to use in fermentation.

*Zymomonas mobilis* and other bacterial ethanologens which do not naturally utilize D-xylose or L-arabinose may be genetically engineered for utilization of these sugars. To provide for D-xylose utilization, strains have been engineered to express genes encoding the following proteins: 1) D-xylose isomerase, which catalyzes the conversion of D-xylose to D-xylulose; 2) xylulokinase, which phosphorylates D-xylulose to form D-xylulose 5-phosphate; 3) transketolase; and 4) transaldolase (U.S. Pat. No. 5,514,583, U.S. Pat. No. 6,566,107; Zhang et al. (1995) Science 267:240-243). To provide for arabinose utilization, genes encoding the following proteins have been introduced: 1) L-arabinose isomerase to convert L-arabinose to L-ribulose, 2) L-ribulokinase to convert L-ribulose to L-ribulose 5-phosphate, and 3) L-ribulose-5-phosphate 4-epimerase to convert L-ribulose 5-phosphate to D-xylulose 5-phosphate (U.S. Pat. No. 5,843,760).

Following introduction of the D-xylose utilization pathway genes, utilization of D-xylose is typically not optimal. *Zymomonas* strains genetically engineered for D-xylose utilization have been adapted for growth on D-xylose containing medium to obtain strains with improved use of D-xylose (U.S. Pat. No. 7,223,575 and U.S. Pat. No. 7,741,119). Further genetic modifications of the *Zymomonas* genome which improve D-xylose utilization have been disclosed in US 2013-0157331 and US 2013-0157332.

There remains a need for *Zymomonas* strains that have effective utilization of D-xylose and/or L-arabinose, and in addition of both D-xylose and L-arabinose, to enhance ethanol production, particularly in a medium containing hydrolyzed lignocellulosic biomass.

SUMMARY OF THE INVENTION

The invention provides recombinant *Zymomonas* cells that have been engineered to utilize D-xylose and recombinant *Zymomonas* cells that have been engineered to utilize both D-xylose and L-arabinose, and that have in addition the inactivation of a locus of the *Zymomonas* genome identified as ZMO0353.

Accordingly, the invention provides a recombinant D-xylose utilizing *Zymomonas* cell comprising at least one genetic modification of an endogenous gene comprising a coding region having at least 95% nucleotide sequence identity to SEQ ID NO:1, wherein expression of a functional protein by the gene is disrupted.

In one embodiment the recombinant D-xylose utilizing *Zymomonas* cell is in addition an L-arabinose utilizing cell.

In another embodiment the D-xylose utilizing or D-xylose and L-arabinose utilizing cell further comprises at least one of the following:
a) reduced glucose-fructose oxidoreductase activity;
b) increased expression of ribose-5-phosphate isomerase having classification EC 5.3.1.6; and
c) at least one genetic modification in the sequence of an endogenous gene encoding polynucleotide phosphorylase that shortens the coding region resulting in expression of a C-terminal truncated protein.

In yet another embodiment the invention provides a process for producing ethanol comprising:
a) providing the any of the recombinant cells described above; and
b) culturing the cell of (a) in a medium comprising at least one of D-xylose and L-arabinose whereby the at least one of D-xylose and L-arabinose is converted to ethanol.

BRIEF DESCRIPTION OF THE DRAWINGS AND SEQUENCE DESCRIPTIONS

Figure 1:
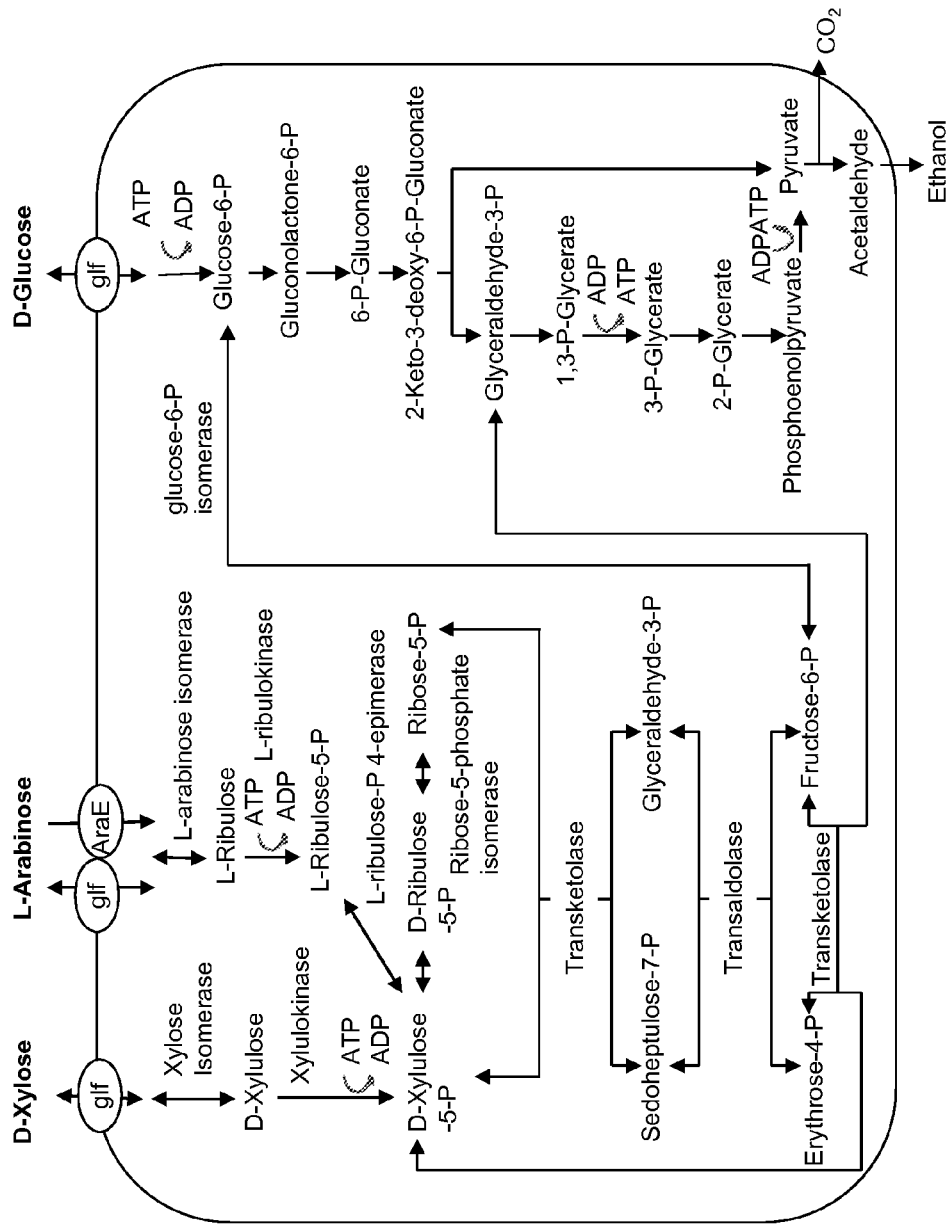
FIG. 1 shows a diagram of metabolic pathways for D-xylose and L-arabinose utilization, and ethanol production, where glf means D-glucose-facilitated diffusion transporter.

The invention can be more fully understood from the following detailed description and the accompanying sequence descriptions which form a part of this application.

The following sequences conform with 37 C.F.R. 1.821-1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (2009) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

SEQ ID NO:1 is the nucleotide sequence of the ZMO0353 ORF of *Z. mobilis* ZM4.

SEQ ID NO:2 is the nucleotide sequence of the ZMO0353 ORF of *Z. mobilis* subsp. *mobilis* NCIMB11163.

SEQ ID NO:3 is the nucleotide sequence of the ZMO0353 ORF of *Z. mobilis* subsp. *mobilis* str. CP4, also called NRRL B-14023.

SEQ ID NO:4 is the nucleotide sequence of the ZMO0353 ORF of *Z. mobilis* subsp. *mobilis* str. NRRL B-12526.

SEQ ID NO:5 is the nucleotide sequence of the ZMO0353 ORF of *Z. mobilis* subsp. *mobilis*, ATCC 29191.

SEQ ID NO:6 is the nucleotide sequence of the ZMO0353 ORF of *Z. mobilis* subsp. *mobilis*, ATCC 10988.

SEQ ID NO:7 is the complete nucleotide sequence of the wild type GFOR coding region from *Z. mobilis*.

SEQ ID NO:8 is the amino acid sequence of RPI from *Z. mobilis* ZM4.

SEQ ID NO:9 is the amino acid sequence of RPI from *E. coli*.

SEQ ID NO:10 is the nucleotide sequence encoding RPI from *E. coli*.

SEQ ID NO:11 is the nucleotide sequence of the ZMO0976 coding region of *Z. mobilis* ZM4....

SEQ ID NO:12 is the amino acid sequence of the protein encoded by the ZMO0976 coding region of *Z. mobilis* ZM4....

SEQ ID NO:13 is the nucleotide sequence of the pnp coding region from *Zymomonas mobilis* strain ZM4.

SEQ ID NO:14 is the amino acid sequence of the pnp encoded polynucleotide phosphorylase from *Zymomonas mobilis* strain ZM4.

SEQ ID NO:15 is the nucleotide sequence of the pnp coding region from *Zymomonas mobilis* strain NCIMB 11163.

SEQ ID NO:16 is the amino acid sequence of the pnp encoded polynucleotide phosphorylase from *Zymomonas mobilis* strain NCIMB 11163.

SEQ ID NO:17 is the nucleotide sequence of the pnp coding region from *Zymomonas mobilis* strain ATCC 10988.

SEQ ID NO:18 is the amino acid sequence of the pnp encoded polynucleotide phosphorylase from *Zymomonas mobilis* strain ATCC 10988.

SEQ ID NO:19 is the nucleotide sequence of the pnp coding region from *Zymomonas mobilis pomaceae* ATCC 29192.

SEQ ID NO:20 is the amino acid sequence of the pnp encoded polynucleotide phosphorylase from *Zymomonas mobilis* strain ATCC 29192.

SEQ ID NO:21 is the amino acid sequence of the modified pnp encoded fusion protein of the I strain, having 709 native N-terminal amino acids and 14 additional C-terminal amino acids.

SEQ ID NO:22 is the amino acid sequence of a modified pnp encoded fusion protein having 695 native N-terminal amino acids and 2 additional C-terminal amino acids.

SEQ ID NO:23 is the amino acid sequence of a modified pnp encoded fusion protein having 368 native N-terminal amino acids and 10 additional C-terminal amino acids.

SEQ ID NO:24 is the amino acid sequence of a modified pnp encoded fusion protein having 32 native N-terminal amino acids and 17 additional C-terminal amino acids.

SEQ ID NOs:25 and 26 are the amino acid sequence and coding region, respectively, for the araA gene of *E. coli*.

SEQ ID NOs:27 and 28 are the amino acid sequence and coding region, respectively, for the araB gene of *E. coli*.

SEQ ID NOs:29 and 30 are the amino acid sequence and coding region, respectively, for the araD gene of *E. coli*.

SEQ ID NO:31 is the nucleotide sequence of the Super GAP promoter, also called $P_{gapS}$.

SEQ ID NO:32 is the nucleotide sequence of the RPI expression cassette.

SEQ ID NO:33 is the nucleotide sequence of the plasmid designated p323del.

SEQ ID NOs:34-36 and 40-43 are primers.

SEQ ID NO:37 is the nucleotide sequence of the 1,318 bp PNP-L fragment.

SEQ ID NO:38 is the nucleotide sequence of the 1,225 bp PNP-R fragment.

SEQ ID NO:39 SpeI-FseI DNA fragment containing a chimeric $P_{gap}$-araBAD operon.

SEQ ID NO:44 is the nucleotide sequence of the 2340 bp PCR-amplified chimeric DNA molecule from the I strain which contains a portion of the transposon-interrupted pnp gene region of the I strain genome (including the ME that caused a frameshift near the 3' end of the pnp gene, which resulted in a truncated pnp protein in the I strain, fused to the Pgap-Rpi expression cassette.

DETAILED DESCRIPTION

The following definitions may be used for the interpretation of the claims and specification:

As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but may include other elements not expressly listed or inherent to such composition, mixture, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances (i.e. occurrences) of the element or component. Therefore "a" or "an" should be read to include one or at least one, and the singular word form of the element or component also includes the plural unless the number is obviously meant to be singular.

The term "invention" or "present invention" as used herein is a non-limiting term and is not intended to refer to any single embodiment of the particular invention but encompasses all possible embodiments as described in the specification and the claims.

As used herein, the term "about" modifying the quantity of an ingredient or reactant of the invention employed refers to variation in the numerical quantity that can occur, for example, through typical measuring and liquid handling procedures used for making concentrates or use solutions in the real world; through inadvertent error in these procedures; through differences in the manufacture, source, or purity of the ingredients employed to make the compositions or carry out the methods; and the like. The term "about" also encompasses amounts that differ due to different equilibrium conditions for a composition resulting from a particular initial mixture. Whether or not modified by the term "about", the claims include equivalents to the quantities. In one embodiment, the term "about" means within 10% of the reported numerical value, preferably within 5% of the reported numerical value.

"Gene" refers to a nucleic acid fragment that expresses a specific protein or functional RNA molecule, which may optionally include regulatory sequences preceding (5' non-coding sequences) and following (3' non-coding sequences) the coding sequence. "Native gene" or "wild type gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes.

"Promoter" or "Initiation control regions" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. Promoters which cause a gene to be expressed in a cell type at most times are commonly referred to as "constitutive promoters".

The term "expression", as used herein, refers to the transcription and stable accumulation of coding (mRNA) or functional RNA derived from a gene. Expression may also refer to translation of mRNA into a polypeptide. "Overexpression" refers to the production of a gene product in transgenic organisms that exceeds levels of production in normal or non-transformed organisms.

The term "transformation" as used herein, refers to the transfer of a nucleic acid fragment into a host organism, resulting in genetically stable inheritance. The transferred nucleic acid may be in the form of a plasmid maintained in the host cell, or some transferred nucleic acid may be integrated into the genome of the host cell. Host organisms containing the transferred nucleic acid fragments are referred to as "transgenic" or "recombinant" or "transformed" organisms or "transformants".

The terms "plasmid" and "vector" as used herein, refer to an extra chromosomal element often carrying genes which are not part of the central metabolism of the cell, and usually in the form of circular double-stranded DNA molecules. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "selectable marker" means an identifying factor, usually an antibiotic or chemical resistance gene, that is able to be selected for based upon the marker gene's effect, i.e., resistance to an antibiotic, wherein the effect is used to track the inheritance of a nucleic acid of interest and/or to identify a cell or organism that has inherited the nucleic acid of interest.

As used herein the term "codon degeneracy" refers to the nature of the genetic code permitting variation of the nucleotide sequence without affecting the amino acid sequence of an encoded polypeptide. The skilled artisan is well aware of the "codon-bias" exhibited by a specific host cell in usage of nucleotide codons to specify a given amino acid. Therefore, when synthesizing a gene for improved expression in a host cell, it may be desirable to design the gene such that its frequency of codon usage approaches the frequency of preferred codon usage of the host cell.

The term "codon-optimized" as it refers to genes or coding regions of nucleic acid molecules for transformation of various hosts, refers to the alteration of codons in the gene or coding regions of the nucleic acid molecules to optimize the production of the polypeptide encoded by the DNA without altering the sequence of the polypeptide.

The term "adapted for growth on D-xylose" refers to a cell or strain isolated after prolonged growth in medium containing D-xylose. Adaptation may include a period of growth in medium containing D-xylose and D-glucose, and then a period of growth in medium containing only D-xylose, each medium being a D-xylose-containing medium. Typically the prolonged period of growth is at least about four days.

The term "adapted strain" refers to a microorganism that has been selected for growth on a particular carbon source in order to improve its ability use that carbon source for the production of products. An "arabinose adapted strain" for example is a strain of microorganism that has been selected for growth on arabinose as a carbon source.

The term "xylose metabolic pathway" or "xylose utilization metabolic pathway" refers to a series of enzymes (encoded by genes) that metabolize D-xylose through to D-fructose-6-phosphate and/or glyceraldehyde-3-phosphate and include 1) D-xylose isomerase, which catalyzes the conversion of D-xylose to D-xylulose; 2) xylulokinase, which phosphorylates D-xylulose to form D-xylulose 5-phosphate; 3) transketolase; and 4) transaldolase.

The term "D-xylose isomerase" or "xylose isomerase" refers to an enzyme that catalyzes the interconversion of D-xylose and D-xylulose. Enzymes classified as EC 5.3.1.5 are known to be xylose isomerases (XI). Some enzymes with xylose isomerase activity may catalyze other reactions in addition to the interconversion of D-xylose and D-xylulose, and may be classified based on their other activity.

The term "xylose" refers to D-xylose.

The term "arabinose" refers to L-arabinose.

The term "ribose-5-phosphate isomerase" or "RPI" refers to an enzyme that catalyzes the interconversion of D-ribulose 5-phosphate and D-ribose 5-phosphate. Enzymes classified as EC 5.3.1.6 are known to be ribose-5-phosphate isomerases. Some enzymes with ribose-5-phosphate isomerase activity may catalyze other reactions in addition to the interconversion of D-ribulose 5-phosphate and D-ribose 5-phosphate, and may be classified based on their other activity.

The term "L-arabinose isomerase" refers to an enzyme that catalyzes the interconversion of L-arabinose and L-ribulose. Enzymes classified as EC 5.3.1.4 are known to be L-arabinose isomerases. Some enzymes with L-arabinose isomerase activity may catalyze other reactions in addition to the interconversion of L-arabinose and L-ribulose, and may be classified based on their other activity.

The term "L-ribulose kinase" refers to an enzyme that catalyzes the conversion of L-ribulose to L-ribulose 5-phosphate. Enzymes classified as EC 2.7.1.16 are known to be L-ribulose kinases. Some enzymes with L-ribulose kinase activity may catalyze other reactions in addition to the conversion of L-ribulose to L-ribulose 5-phosphate, and may be classified based on their other activity.

The term "L-ribulose-5-phosphate 4-epimerase" refers to an enzyme that catalyzes the interconversion of L-ribulose 5-phosphate and D-xylulose 5-phosphate. Enzymes classified as EC 5.1.3.22 are known to be L-ribulose-5-phosphate 4-epimerases. Some enzymes with L-ribulose-5-phosphate 4-epimerase activity may catalyze other reactions in addition to the interconversion of L-ribulose 5-phosphate and D-xylulose 5-phosphate, and may be classified based on their other activity.

The term "carbon substrate" or "fermentable carbon substrate" refers to a carbon source capable of being metabolized by microorganisms. A type of carbon substrate is "fermentable sugars" which refers to oligosaccharides and monosaccharides that can be used as a carbon source by a microorganism in a fermentation process.

The term "lignocellulosic" refers to a composition comprising both lignin and cellulose. Lignocellulosic material may also comprise hemicellulose.

The term "cellulosic" refers to a composition comprising cellulose and additional components, including hemicellulose.

The term "saccharification" refers to the production of fermentable sugars from polysaccharides.

The term "pretreated biomass" means biomass that has been subjected to thermal, physical and/or chemical pretreatment to increase the availability of polysaccharides in the biomass to saccharification enzymes.

"Biomass" refers to any cellulosic or lignocellulosic material and includes materials comprising cellulose, and optionally further comprising hemicellulose, lignin, starch, oligosaccharides and/or monosaccharides. Biomass may also comprise additional components, such as protein and/or lipid. Biomass may be derived from a single source, or biomass can comprise a mixture derived from more than one source; for example, biomass could comprise a mixture of corn cobs and corn stover, or a mixture of grass and leaves. Biomass includes, but is not limited to, bioenergy crops, agricultural residues, municipal solid waste, industrial solid waste, sludge from paper manufacture, yard waste, wood and forestry waste. Examples of biomass include, but are not limited to, corn cobs, crop residues such as corn husks, corn stover, grasses, wheat, wheat straw, barley straw, hay, rice straw, switchgrass, waste paper, sugar cane bagasse, sorghum, components obtained from milling of grains, trees, branches, roots, leaves, wood chips, sawdust, shrubs and bushes, vegetables, fruits, flowers and animal manure.

"Biomass hydrolysate" refers to the product resulting from saccharification of biomass. The biomass may also be pretreated or pre-processed prior to saccharification.

The term "heterologous" means not naturally found in the location of interest. For example, a heterologous gene refers to a gene that is not naturally found in the host organism, but that is introduced into the host organism by gene transfer. For example, a heterologous nucleic acid molecule that is present in a chimeric gene is a nucleic acid molecule that is not naturally found associated with the other segments of the chimeric gene, such as the nucleic acid molecules having the coding region and promoter segments not naturally being associated with each other.

As used herein, an "isolated nucleic acid molecule" is a polymer of RNA or DNA that is single- or double-stranded, optionally containing synthetic, non-natural or altered nucleotide bases. An isolated nucleic acid molecule in the form of a polymer of DNA may be comprised of one or more segments of cDNA, genomic DNA or synthetic DNA.

The term "percent identity", as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in: 1.) *Computational Molecular Biology* (Lesk, A. M., Ed.) Oxford University: NY (1988); 2.) *Biocomputing: Informatics and Genome Projects* (Smith, D. W., Ed.) Academic: NY (1993); 3.) *Computer Analysis of Sequence Data, Part I* (Griffin, A. M., and Griffin, H. G., Eds.) Humania: NJ (1994); 4.) *Sequence Analysis in Molecular Biology* (von Heinje, G., Ed.) Academic (1987); and 5.) *Sequence Analysis Primer* (Gribskov, M. and Devereux, J., Eds.) Stockton: NY (1991).

Preferred methods to determine identity are designed to give the best match between the sequences tested. Methods to determine identity and similarity are codified in publicly available computer programs. Sequence alignments and percent identity calculations may be performed using the MegAlign program of the LASERGENE bioinformatics computing suite (DNASTAR Inc., Madison, Wis.).

Multiple alignment of the sequences is performed using the "Clustal method of alignment" which encompasses several varieties of the algorithm including the "Clustal V method of alignment" corresponding to the alignment method labeled Clustal V (described by Higgins and Sharp, *CABIOS*. 5:151-153 (1989); Higgins, D. G. et al., *Comput. Appl. Biosci.*, 8:189-191 (1992)) and found in the MegAlign v8.0 program of the LASERGENE bioinformatics computing suite (DNASTAR Inc.). For multiple alignments, the default values correspond to GAP PENALTY=10 and GAP LENGTH PENALTY=10. Default parameters for pairwise alignments and calculation of percent identity of protein sequences using the Clustal method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. After alignment of the sequences using the Clustal V program, it is possible to obtain a "percent identity" by viewing the "sequence distances" table in the same program.

Additionally the "Clustal W method of alignment" is available and corresponds to the alignment method labeled Clustal W (described by Higgins and Sharp, *CABIOS*. 5:151-153 (1989); Higgins, D. G. et al., *Comput. Appl. Biosci.* 8:189-191(1992); Thompson, J. D. et al, Nucleic Acid Research, 22 (22): 4673-4680, 1994) and found in the MegAlign v8.0 program of the LASERGENE bioinformatics computing suite (DNASTAR Inc.). Default parameters for multiple alignment (stated as protein/nucleic acid (GAP PENALTY=10/15, GAP LENGTH PENALTY=0.2/6.66, Delay Divergen Seqs (%)=30/30, DNA Transition Weight=0.5, Protein Weight Matrix=Gonnet Series, DNA Weight Matrix=IUB). After alignment of the sequences using the Clustal W program, it is possible to obtain a "percent identity" by viewing the "sequence distances" table in the same program.

It is well understood by one skilled in the art that many levels of sequence identity are useful in identifying polypeptides, from other species, wherein such polypeptides have the same or similar function or activity. Useful examples of percent identities include, but are not limited to: 50%, 55%, 60%, 65%, 70%, 75%, 80%, 85%, 90%, or 95%, or any integer percentage from 50% to 100% may be useful in identifying polypeptides of interest, such as 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99%. Suitable nucleic acid fragments also have any of the above identities, and typically encode a polypeptide having at least 50 amino acids, preferably at least 100 amino acids, and more preferably at least 125 amino acids.

The term "sequence analysis software" refers to any computer algorithm or software program that is useful for the analysis of nucleotide or amino acid sequences. "Sequence analysis software" may be commercially available or independently developed. Typical sequence analysis software will include, but is not limited to: 1) the GCG suite of programs (Wisconsin Package Version 9.0, Genetics Computer Group (GCG), Madison, Wis.); 2) BLASTP, BLASTN, BLASTX (Altschul et al., J. Mol. Biol., 215:403-410 (1990)); 3) DNASTAR (DNASTAR, Inc. Madison, Wis.); 4) Vector NTI® (Life Technologies), 5) Sequencher (Gene Codes Corporation, Ann Arbor, Mich.); and 6) the FASTA program incorporating the Smith-Waterman algorithm (W. R. Pearson, Comput. Methods Genome Res., [Proc. Int. Symp.] (1994), Meeting Date 1992, 111-20. Editor(s): Suhai, Sandor. Plenum: New York, N.Y.). Within the context of this application it will be understood that where sequence analysis software is used for analysis, that the results of the analysis will be based on the "default values" of the program referenced, unless otherwise specified. As used herein "default values" will mean any set of values or parameters that originally load with the software when first initialized.

Standard recombinant DNA and molecular cloning techniques used herein are well known in the art and are described by Sambrook, J. and Russell, D., *Molecular Cloning: A Laboratory Manual*, Third Edition, Cold Spring Harbor Laboratory Press, Cold Spring Harbor, N.Y. (2001); and by Silhavy, T. J., Bennan, M. L. and Enquist, L. W., *Experiments with Gene Fusions*, Cold Spring Harbor Laboratory Press, Cold Spring Harbor, N.Y. (1984); and by Ausubel, F. M. et. al., *Short Protocols in Molecular Biology*, 5$^{th}$ Ed. Current Protocols, John Wiley and Sons, Inc., N.Y., 2002.

The present invention relates to *Zymomonas* cells that have enhanced D-xylose utilization. The cells may in addition have enhanced L-arabinose utilization. The present *Zymomonas* cells are useful for production of ethanol.

Endogenous ZMO0353 Gene Modification

The present invention is directed to cells of engineered *Zymomonas* strains, which are recombinant cells, which utilize at least one of D-xylose and L-arabinose, that have a modified endogenous gene containing a coding region having at least 95% nucleotide sequence identity to SEQ ID NO:1. The sequence of SEQ ID NO:1 is labeled as the ZMO0353 ORF (open reading frame) in the genomic sequence of the *Zymomonas mobilis* ZM4 strain (strain ATCC 31821; genomic sequence GenBank accession number AE008692 (Seo et al., Nat. Biotechnol. 23 (1), 63-68 (2005)) and NCBI Reference: NC_006526.2). Modification of the ZMO0353 ORF that disrupted expression of a functional protein was found herein to improve D-xylose utilization in cells of engineered *Zymomonas* strains that utilize D-xylose, or D-xylose and L-arabinose. In addition, use of arabinose was improved in cells of engineered *Zymomonas* strains that utilize D-xylose and L-arabinose.

The ZMO0353 coding region is annotated as encoding a 4-diphosphocytidyl-2C-methyl-D-erythritol synthase. An enzyme homologous to the protein encoded by ZMO0353, however, was found by Follens et al. ((1999) J. of Bacteriology 181:2001-2007) to have both ribulose-5-phosphate reductase and CDP-ribitol pyrophosphorylase activities. This enzyme was further characterized as having D-ribulose phosphate reduction activity (Zolli et al. (2001) Biochemistry 40:5041-5048).

The genomes of other strains of *Zymomonas mobilis* each have an endogenous gene that is equivalent to the ZMO0535 ORF. For example, the *Zymomonas mobilis* subsp. *mobilis* NCIMB11163 has an ORF (SEQ ID NO:2) which has 99% identity to SEQ ID NO:1, the *Zymomonas mobilis* subsp. *mobilis* str. CP4, also called NRRL B-14023, has an ORF (SEQ ID NO:3) which has 98% identity to SEQ ID NO:1, *Zymomonas mobilis* subsp. *mobilis* str. NRRL B-12526 has an ORF (SEQ ID NO:4) which has 98% identity to SEQ ID NO:1, *Zymomonas mobilis* subsp. *mobilis*, ATCC 29191, has an ORF (SEQ ID NO:5) which has 98% identity to SEQ ID NO:1, and *Zymomonas mobilis* subsp. *mobilis*, ATCC 10988, has an ORF (SEQ ID NO:6) which has 97% identity to SEQ ID NO:1. Thus it is expected that every strain of *Zymomonas mobilis* has a coding region with at least about 95%, 96%, 97%, 98%, 99%, or 100% nucleotide sequence identity to SEQ ID NO:1, and these coding regions are included when referring herein to ZMO0353. In the present cells, expression of a functional protein by a gene that contains a coding region identified as ZMO0353 is disrupted.

Disruption of expression of a functional protein by a gene that contains a coding region identified as ZMO0353 may be achieved by any method known to one skilled in the art such as methods that affect its expression of mRNA or protein, or the function or stability of the encoded protein. Genetic modifications may be, for example, insertion, deletion, or mutation in the coding region, or other region of the gene such as the promoter. Methods include, but are not limited to, deletion of the entire or a portion of the gene, inserting a DNA fragment into the gene (in either the promoter or coding region) so that the encoded protein cannot be expressed, introducing a mutation into the coding region which adds a stop codon or frame shift such that a functional protein is not expressed, and introducing one or more mutations into the coding region to alter amino acids so that a non-functional protein is expressed. All of these methods may be readily practiced by one skilled in the art making use of the known target ZMO0353 coding sequence (such as SEQ ID NO:1), as well as the *Zymomonas* DNA sequences that surrounds this target sequence, such as sequences that are available in the complete *Z. mobilis* genome sequence (for example, GenBank Accession AE008692 for ZM4).

A particularly suitable method for creating a genetic modification in a ZMO0353 containing target gene is to delete the coding sequence from the genome as exemplified herein in Examples 1 and 2. A plasmid is constructed which contains genomic sequence regions that lie adjacent to the target coding region. A *Zymomonas* cell is transformed with the plasmid and two recombination events occur with the first integrating the entire plasmid, and the second deleting the plasmid sequences and the target coding region.

Deletion of the ZMO0353 sequence in *Z. mobilis* was shown herein in Example 3 to increase D-xylose utilization in D-xylose utilizing cells of *Z. mobilis*. as compared to cells that lack the ZMO0353 deletion and are otherwise identical. When grown in medium starting with 96.1 g/L of D-xylose, one culture showed a 13.2% increase in D-xylose utilization after 23 hours, and a 19.6% increase after 46 hours. D-xylose utilization by the deletion strain remained greater than that of the strain lacking the deletion throughout the 144 hour experiment, with a 3.3% increase in D-xylose utilization at 144 hours. A second culture showed a greater increase in xylose utilization.

Cultures of cells which are D-xylose utilizing *Z. mobilis* cells having a deletion of ZMO0353, starting with an $OD_{600}$ of 0.05, used at least about 56 g/L of D-xylose when grown at 33° C. with shaking for 46 hours in medium initially containing about 96 g/L of D-xylose. In various embodiments cultures of cells having at least one genetic modification of an endogenous gene comprising a coding region having nucleotide sequence identity of at least 95% to SEQ ID NO:1, wherein expression of a functional protein by the gene is disrupted, use at least about 56, 58, 60, 62, 64, 66, 68, 70 or more g/L of D-xylose when grown in these conditions.

Deletion of the ZMO0353 sequence in *Z. mobilis* was shown herein in Example 6 to increase D-xylose utilization and L-arabinose utilization in D-xylose and L-arabinose utilizing cells of *Z. mobilis*. When grown in medium starting with 96.8 g/L D-xylose, D-xylose utilization was on average more than seven times higher after 24 hours and more than four times higher after 67 hours in the deletion strain cultures as compared to cultures of an otherwise identical strain lacking the deletion. In cultures growing on 48.8 g/L L-arabinose, L-arabinose utilization was on average more than doubled after 24 hours and still more than 50% greater after 67 hours in cultures or the deletion strain as compared to cultures of an otherwise identical strain lacking the deletion.

The increase in utilization of D-glucose or L-arabinose in D-xylose utilizing or D-xylose and L-rabinose utilizing cells will vary depending on factors such as other genetic modifications in the cells, growth media, culture conditions, and time of analysis. The increase in xylose utilization by the present cells, as compared to cells identical except lacking the ZMO0353 modification, is at least about 1%, 5%, 8%, 10%, 12%, 20%, 25%, 50%, 75%, 100%, or greater. The increase in L-arabinose utilization by the present cells, as compared to cells that are identical except lacking the ZMO0353 modification, is at least about 1%, 5%, 8%, 10%, 12%, 20%, 25%, 50%, 75%, 100%, or greater.

Cultures of cells which are D-xylose and L-arabinose utilizing *Z. mobilis* cells having a deletion of ZMO0353, starting with an $OD_{600}$ of 0.06, used at least about 28 g/L of L-arabinose when grown at 33° C. with shaking for 43 hours in medium initially containing about 49 g/L of L-arabinose. In various embodiments cultures of cells having at least one genetic modification of an endogenous gene comprising a coding region having nucleotide sequence identity of at least 95% to SEQ ID NO:1, wherein expression of a functional protein by the gene is disrupted, use at least about 28, 30, 32, 34, 36, 38, 40, or more g/L of L-arabinose when grown in these conditions.

Cultures of cells which are D-xylose and L-arabinose utilizing *Z. mobilis* cells having a deletion of ZMO0353, starting with an $OD_{600}$ of 0.06, used at least about 20 g/L of D-xylose when grown at 33° C. with shaking for 43 hours in medium initially containing about 97 g/L of D-xylose. In various embodiments cultures of cells having at least one genetic modification of an endogenous gene comprising a coding region having nucleotide sequence identity of at least 95% to SEQ ID NO:1, wherein expression of a functional protein by the gene is disrupted, use at least about 20, 25, 30, 35, 40, 45, 50, 55, 60, 65, 70, 75, 80, 85, or more g/L of D-xylose when grown in these conditions.

In various embodiments, the cells use L-arabinose and D-xylose in any combination of the amounts given for use of each above, such as at least about 20 g/L of D-xylose and at least about 28 g/L of L-arabinose, under the culture conditions given above.

In addition, as shown in Example 6 herein, ethanol production was improved in ZMO0353 deletion strains as well. With growth on 96.8 g/L D-xylose, ethanol production was increased proportionally to the increase in the amount of xylose utilized in cultures of the deletion strain compared to those from an otherwise identical strain lacking the deletion. Increases in ethanol production varied between 2.4-fold to 6-fold, and greater. With growth on 48.8 g/L L-arabinose, ethanol production also increased proportionally to the increase in arabinose utilization in cultures of the deletion strain compared to those of an otherwise identical strain lacking the deletion. Increases in ethanol production varied between 18% and 58%, and greater.

The increase in ethanol production by the present cells will vary depending on factors such as other genetic modifications in the cells, growth media, culture conditions, and time of analysis. The increase in ethanol production by the present cells, as compared to cells identical except lacking the ZMO0353 modification, is at least about 1%, 5%, 10%, 15%. 20%, 25%, 50%, 75%, 100%, 200%, or greater.

D-Xylose Utilizing *Zymomonas*

Any genetic modifications that confer the ability to use D-xylose may be present in the present recombinant D-xylose utilizing *Zymomonas* cell. *Zymomonas* cells naturally produce ethanol using D-glucose, D-fructose and/or sucrose as fermentation substrates, but D-xylose is not metabolized. Strains of ethanol-producing *Zymomonas*, such as *Z. mobilis* have been engineered for D-xylose fermentation to ethanol. Typically four coding regions have been introduced into *Z. mobilis* for expression of four enzymes involved in D-xylose metabolism to create a D-xylose utilization metabolic pathway (see FIG. 1) as described in U.S. Pat. No. 5,514,583, U.S. Pat. No. 5,712,133, U.S. Pat. No. 6,566,107, WO 95/28476, Feldmann et al. ((1992) Appl Microbiol Biotechnol 38: 354-361), and Zhang et al. ((1995) Science 267:240-243). The enzymes include D-xylose isomerase which catalyzes the conversion of D-xylose to D-xylulose, and xylulokinase which phosphorylates D-xylulose to form D-xylulose 5-phosphate. Additionally expressed are transketolase and transaldolase, two enzymes of the pentose phosphate pathway that convert xylulose 5-phosphate to intermediates that couple pentose metabolism to the glycolytic Entner-Douderoff pathway permitting the metabolism of D-xylose to ethanol (see FIG. 1). DNA sequences encoding these enzymes may be obtained from any of numerous microorganisms that are able to metabolize D-xylose, such as enteric bacteria, and some yeasts and fungi. Sources for the coding regions may include *Xanthomonas, Klebsiella, Escherichia, Rhodobacter, Flavobacterium, Acetobacter, Gluconobacter, Rhizobium, Agrobacterium, Salmonella, Pseudomonads*, and *Zymomonas*.

Because the sequences of these proteins and their coding regions are well known, suitable proteins and coding regions may be readily identified in D-xylose utilizing microorganisms, such as those listed above, by one skilled in the art on the basis of enzyme activity, E.C. number, and/or sequence similarity using bioinformatics, and also by experimental methods as described below for L-arabinose utilization pathway genes.

The encoding DNA sequences are operably linked to promoters that result in expression in *Zymomonas* cells such as the promoter of *Z. mobilis* glyceraldehyde-3-phosphate dehydrogenase (GAP promoter), *Z. mobilis* enolase (ENO promoter), and of the *Actinoplanes missouriensis* xylose isomerase encoding gene (GI promoter, Pgi). A mutant GAP promoter with increased expression as disclosed in U.S. Pat. No. 7,989,206, which is incorporated herein by reference, is also useful for expression in *Zymomonas*. The coding regions may individually be expressed from promoters, or two or more coding regions may be joined in an operon with expression from the same promoter. The resulting chimeric genes may be introduced into *Zymomonas* cells and maintained on a plasmid, or integrated into the genome using, for example, homologous recombination, site-directed integration, or random integration.

Vectors are well known in the art. Particularly useful for expression in *Zymomonas* are vectors that can replicate in both *E. coli* and *Zymomonas*, such as pZB188 which is described in U.S. Pat. No. 5,514,583. Vectors may include plasmids for autonomous replication in a cell, and plasmids for carrying constructs to be integrated into the cell genome. Plasmids for DNA integration may include transposons, regions of nucleic acid sequence homologous to the target cell genome, site-directed integration sequences, or other sequences supporting integration. In homologous recombination, DNA sequences flanking a target integration site are placed bounding the desired chimeric gene and optionally a selectable marker, leading to insertion of the chimeric gene into the target genomic site.

Examples of strains engineered to express a D-xylose utilization metabolic pathway include CP4(pZB5) (U.S. Pat. No. 5,514,583), ATCC31821/pZB5 (U.S. Pat. No. 6,566,107), 8b (US 20030162271; Mohagheghi et al., (2004) Biotechnol. Lett. 25; 321-325), and ZW658 (ATTCC # PTA-7858) with derivatives ZW800, ZW801-4 (U.S. Pat. No. 7,741,119), and ZW705 (U.S. Pat. No. 8,247,208). Cells of *Zymomonas* that are engineered for expression of the D-xylose utilization metabolic pathway also may be adapted in D-xylose-containing medium, since cells engineered with the D-xylose metabolic pathway may demonstrate improved D-xylose utilization after a period of adaptation in D-xylose-containing medium. Adaptation on D-xylose-containing medium is described in U.S. Pat. No. 7,223,575 and U.S. Pat. No. 7,741,119, which are incorporated herein by reference.

In one embodiment D-xylose utilizing *Zymomonas* cells are as described above. In other embodiments, one or more additional modifications that improve D-xylose utilization are present in the cells. Additional modifications that improve D-xylose utilization that may be present in a D-xylose utilizing *Zymomonas* cell include those described as follows. A genetic modification may be present in the cell that reduces glucose-fructose oxidoreductase (GFOR) activity as disclosed in U.S. Pat. No. 7,741,119, which is incorporated herein by reference. Reduced expression of GFOR may be by any method known to one skilled in the art such as those described in U.S. Pat. No. 7,741,119 and those described below for disrupting the gene containing the ZMO0353 coding region. The sequence of the coding region for GFOR in the ZM4 strain of *Zymomonas mobilis* is SEQ ID NO:7. Equivalent sequences of 95%, 96%, 97%, 98%, or 99% sequence identities may be present in other *Zymomonas* strains. DNA sequences surrounding the GFOR coding sequence are also useful in some modification procedures (described below) such as those available for *Z. mobilis* in the complete genome sequence (GenBank Accession #AE008692).

A genetic modification may be present in the cell which increases ribose-5-phosphate isomerase (RPI) activity, as disclosed in US patent publication 2012-0156746, which is incorporated herein by reference. Increased RPI expression may be accomplished by any method known to one skilled in the art. For example, a modification may be made to increase expression of the endogenous RPI encoding gene, such as with a promoter that is more highly active than the native promoter, or by expressing a heterologous gene encoding any protein or polypeptide with ribose-5-phosphate isomerase activity in *Zymomonas*. There are two groups of ribose-5-phosphate isomerase enzymes that are called RPI-A and RPI-B, as described in US patent publication 2012-0156746, either of which may be expressed. Examples of endogenous and heterologous RPIs are, respectively, from the *Z. mobilis* strain ZM4 with amino acid sequence of SEQ ID NO:8, and from *E. coli* with amino acid and coding sequences of SEQ ID NOs:9 and 10, respectively. Additional sequences that may be expressed to increase RPI activity include those identified in US patent publication 2012-0156746 and those identified by BLAST analysis by one skilled in the art.

A genetic modification may be present in the cell that reduces aldose reductase activity, specifically an enzyme that converts xylose to xylitol in the presence of a cofactor such as NADPH (which is converted to NADP) or NADH (which is converted to NAD). An enzyme which uses NADPH in this reaction is referred to as NADPH-dependent xylose reductase and may be assigned to EC 1.1.1.21, as disclosed in US patent application publication 2013-0157332, which is incorporated herein by reference. This modification allows immediate growth on medium containing only D-xylose as the carbon source by cells containing xylose utilization pathway genes. Such a genetic modification may be made in the ZMO0976 coding region (SEQ ID NO:11; encoding protein of SEQ ID NO:12 of the *Z. mobilis* ZM4 strain (GenBank accession #AE008692), and/or in one or more coding region of other putative aldo/keto reductases, which are named ZMO0976, ZMO1344, ZMO1673, and ZMO1773.

Additionally, the D-xylose isomerase that is expressed as part of the D-xylose utilization metabolic pathway may be expressed using a mutant, highly active promoter that is disclosed in U.S. Pat. No. 7,989,206 and U.S. Pat. No. 7,998, 722, which are incorporated herein by reference. The mutant promoters disclosed therein are promoters of the *Zymomonas mobilis* glyceraldehyde-3-phosphate dehydrogenase gene. In addition, a D-xylose isomerase that is expressed as part of the D-xylose utilization metabolic pathway may be a Group I D-xylose isomerase included in the class of enzymes identified by EC 5.3.1.5 as disclosed in U.S. Pat. No. 8,623,623. The D-xylose isomerase that is expressed in the D-xylose utilizing cell may be a Group 1 D-xylose isomerase, which has better activity in *Zymomonas* that a Group 2 D-xylose Isomerase as disclosed in U.S. Pat. No. 8,623,623, which is incorporated herein by reference.

Further, the present cell may have at least one genetic modification in the sequence of an endogenous gene encoding polynucleotide phosphorylase (pnp) that shortens the coding region resulting in expression of a C-terminal truncated protein, as disclosed in US Patent Application 2013-0157331. This modification can improve xylose utilization in a xylose utilizing cell. Any gene of *Zymomonas* that is identified as encoding a protein with polynucleotide phosphorylase or polyribonucleotide nucleotidyltransferase activity may provide the target endogenous pnp gene for modification. The pnp coding region of *Zymomonas mobilis* strain ZM4 has the sequence of SEQ ID NO:13. Known endogenous pnp coding regions from other strains of *Zymomonas* have sequences with identities to SEQ ID NO:1 of 99% (*Z. mobilis* NCIMB 11163; SEQ ID NO:15), 98% (*Z. mobilis* ATCC 10988; SEQ ID NO:17), and 83% (*Z. mobilis pomaceae* ATCC 29192; SEQ ID NO:19). Any of these sequences, or any sequence with at least about 95%, 96%, 97%, 98%, or 99% identity to any one of these sequences and identified as encoding a polynucleotide phosphorylase or polyribonucleotide nucleotidyltransferase may be used as the target for modification. Additional target endogenous pnp gene sequences may be identified using BLAST analysis or other sequence comparison analyses that are well known to one skilled in the art.

The pnp coding region may be modified to shorten the coding region at the 3' end resulting in expression of a C-terminal truncated protein, as compared to the naturally encoded protein. The native encoded polynucleotide phosphorylase of *Zymomonas mobilis* is a protein of about 748 amino acids, which is any of SEQ ID NOs:14, 16, 18, 20 or any sequence with at least about 95%, 96%, 97%, 98%, or 99% identity to any one of these sequences and identified as a polynucleotide phosphorylase or polyribonucleotide nucleotidyltransferase. The truncated protein expressed from the modified pnp coding region may retain at least about 350 and up to about 710 amino acids of the N-terminal amino acid sequence encoded by the endogenous gene encoding polynucleotide phosphorylase, which are native N-terminal amino acids. Additional coding sequence for non-native amino acids adjacent to and in frame with the truncated native coding region may be added so that a fusion protein is produced as disclosed in US Patent Application 2013-0157331. Examples of fusion proteins are SEQ ID NOs:21-24. The modification may be performed by any method known to one skilled in the art. Typically a targeted integration event is performed. An example of a *Zymomonas* strain containing a genetic modification of an endogenous pnp gene is the I strain, which is described in the Examples section herein.

Arabinose Utilizing *Zymomonas*

Any genetic modifications that confer the ability to use arabinose may be present in the present D-xylose and L-arabinose utilizing *Zymomonas* cell. *Zymomonas* cells do not naturally metabolize arabinose. Strains of ethanol-producing *Zymomonas*, such as *Z. mobilis* have been engineered for arabinose fermentation to ethanol. Typically three heterologous coding regions have been introduced into *Z. mobilis* for expression of enzymes involved in arabinose metabolism to create an arabinose utilization metabolic pathway (see FIG. 1) as described in U.S. Pat. No. 5,843,760, which is incorporated herein by reference. The enzymes include L-arabinose isomerase to convert L-arabinose to L-ribulose, L-ribulose kinase to convert L-ribulose to L-ribulose 5-phosphate, and L-ribulose-5-phosphate 4-epimerase to convert L-ribulose 5-phosphate to D-xylulose 5-phosphate.

DNA sequences encoding these enzymes may be obtained from any microorganisms that are able to metabolize arabinose. Sources for the coding regions include *Klebsiella, Escherichia, Rhizobium, Agrobacterium,* and *Salmonella*. Particularly useful are the coding regions of *E. coli* which are for L-arabinose isomerase: coding region of araA (coding region SEQ ID NO:25; protein SEQ ID NO:26), for L-ribulokinase: coding region of araB (coding region SEQ ID NO:27; protein SEQ ID NO:28), and for L-ribulose-5-phosphate-4-epimerase: coding region of araD (coding region SEQ ID NO:29; protein SEQ ID NO:30). Because the sequences of these proteins and their coding regions are well known, as exemplified in the sequences given above, additional suitable proteins and coding regions may be readily identified in other arabinose utilizing microorganisms, such as those listed above, by one skilled in the art on the basis of sequence similarity using bioinformatics, and also by experimental methods. Typically BLAST (described above) searching of publicly available databases with known L-arabinose isomerase, L-ribulose kinase, or L-ribulose-5-phosphate 4-epimerase amino acid sequences, such as those provided herein, is used to identify additional proteins with the same function, and their encoding sequences, that may be used in the present strains. These proteins may have at least about 80-85%, 85%-90%, 90%-95% or 95%-99% sequence identity to any of the L-arabinose isomerase, L-ribulose kinase, or L-ribulose-5-phosphate 4-epimerase amino acid sequences of SEQ ID NOS:26, 28, or 30, respectively, while having L-arabinose isomerase, L-ribulose kinase, or L-ribulose-5-phosphate 4-epimerase activity. Identities are based on the Clustal W method of alignment using the default parameters of GAP PENALTY=10, GAP LENGTH PENALTY=0.1, and Gonnet 250 series of protein weight matrix.

In addition to using protein or coding region sequences and bioinformatics methods to identify additional proteins with the same activities, the sequences described herein or those recited in the art may be used to experimentally identify other homologs in nature. For example each of the encoding nucleic acid fragments described herein may be used to isolate genes encoding homologous proteins. Isolation of homologous genes using sequence-dependent protocols is well known in the art. Examples of sequence-dependent protocols include, but are not limited to: 1.) methods of nucleic acid hybridization; 2.) methods of DNA and RNA amplification, as exemplified by various uses of nucleic acid amplification technologies [e.g., polymerase chain reaction (PCR), Mullis et al., U.S. Pat. No. 4,683,202; ligase chain reaction (LCR), Tabor, S. et al., *Proc. Acad. Sci.* USA 82:1074 (1985); or strand displacement amplification (SDA), Walker, et al., *Proc. Natl. Acad. Sci. U.S.A.*, 89:392 (1992)]; and 3.) methods of library construction and screening by complementation.

For example, coding regions for similar proteins or polypeptides to the known L-arabinose isomerase, L-ribulose kinase, or L-ribulose-5-phosphate 4-epimerase encoding sequences described herein could be isolated directly by using all or a portion of the instant nucleic acid fragments as DNA hybridization probes to screen libraries from any desired organism using methodology well known to those skilled in the art. Specific oligonucleotide probes based upon the disclosed nucleic acid sequences can be designed and synthesized by methods known in the art (Maniatis, supra). Moreover, the entire sequences can be used directly to synthesize DNA probes by methods known to the skilled artisan (e.g., random primers DNA labeling, nick translation or end-labeling techniques), or RNA probes using available in vitro transcription systems. In addition, specific primers can be designed and used to amplify a part of (or full-length of) the instant sequences. The resulting amplification products can be labeled directly during amplification reactions or labeled after amplification reactions, and used as probes to isolate full-length DNA fragments by hybridization under conditions of appropriate stringency.

Typically, in PCR-type amplification techniques, the primers have different sequences and are not complementary to each other. Depending on the desired test conditions, the sequences of the primers should be designed to provide for both efficient and faithful replication of the target nucleic acid. Methods of PCR primer design are common and well known in the art (Thein and Wallace, "The use of oligonucleotides as specific hybridization probes in the Diagnosis of Genetic Disorders", in *Human Genetic Diseases: A Practical Approach*, K. E. Davis Ed., (1986) pp 33-50, IRL: Herndon, Va.; and Rychlik, W., In *Methods in Molecular Biology*, White, B. A. Ed., (1993) Vol. 15, pp 31-39, PCR Protocols: Current Methods and Applications. Humania: Totowa, N.J.).

Generally two short segments of the described sequences may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the described nucleic acid fragments, and the sequence of the other primer takes advantage of the presence of the polyadenylic acid tracts to the 3' end of the mRNA precursor encoding microbial genes.

Alternatively, the second primer sequence may be based upon sequences derived from the cloning vector. For example, the skilled artisan can follow the RACE protocol (Frohman et al., *PNAS USA* 85:8998 (1988)) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (e.g., BRL, Gaithersburg, Md.), specific 3' or 5' cDNA fragments can be isolated (Ohara et al., *PNAS USA* 86:5673 (1989); Loh et al., *Science* 243:217 (1989)).

Alternatively, the encoding sequences of interest may be employed as hybridization reagents for the identification of homologs. The basic components of a nucleic acid hybridization test include a probe, a sample suspected of containing the gene or gene fragment of interest, and a specific hybridization method. Probes are typically single-stranded nucleic acid sequences that are complementary to the nucleic acid sequences to be detected. Probes are "hybridizable" to the nucleic acid sequence to be detected. The probe length can vary from 5 bases to tens of thousands of bases, and will depend upon the specific test to be done. Typically a probe length of about 15 bases to about 30 bases is suitable. Only part of the probe molecule need be complementary to the nucleic acid sequence to be detected. In addition, the complementarity between the probe and the target sequence need not be perfect. Hybridization does occur between imperfectly complementary molecules with the result that a certain fraction of the bases in the hybridized region are not paired with the proper complementary base.

Arabinose utilization pathway coding regions are operably linked to promoters making chimeric genes in vectors and can be used to transform *Zymomonas* cells, all as described above for xylose utilization pathway coding regions.

In addition, transketolase and transaldolase activities are used in the biosynthetic pathway from arabinose to ethanol (see FIG. 1), which are common to the D-xylose utilization pathway described above Cells of *Zymomonas* that are engineered for expression of the arabinose utilization metabolic pathway may also be adapted in arabinose-containing medium, since adaptation in arabinose-containing medium may improve arabinose utilization in some cells engineered with the arabinose metabolic pathway.

An arabinose utilizing cell may in addition express an arabinose-proton symporter, such as by expressing a coding region from an araE gene, which was disclosed to improve arabinose utilization in US 2011/0143408, which is incorporated herein by reference.

Additional *Zymomonas* Cell Modifications

Additional modifications that improve growth and ethanol production in medium containing biomass hydroysate may be present in the present D-xylose utilizing, or D-xylose and L-arabinose utilizing *Zymomonas* cell. The *Zymomonas* cell may have been adapted for growth in a stress culture containing ethanol and ammonium acetate as disclosed in U.S. Pat. No. 8,247,208, which is incorporated herein by reference. These *Zymomonas* strains with improved acetate tolerance are particularly useful when using cellulosic biomass hydrolysate containing fermentation medium, which contains acetate. The *Zymomonas* cell may have been adapted in a continuous flow culture in hydrolysate medium as disclosed in U.S. Pat. No. 8,476,048, which is incorporated herein by reference. The *Zymomonas* cell may have a genetic modification of the ZMO1432 open reading frame (NCBI Reference: NC_006526.2) as disclosed in U.S. Pat. No. 8,476,048, which confers higher tolerance to biomass hydrolysate.

Fermentation for Ethanol Production

An engineered *Zymomonas* cell having a D-xylose utilization pathway or having a D-xylose utilization pathway and an L-arabinose utilization pathway, and at least one genetic modification of an endogenous gene comprising a coding region having at least 95% nucleotide sequence identity to SEQ ID NO:1, wherein expression of a functional protein by the gene is disrupted, may be used in fermentation to produce ethanol. *Zymomonas mobilis* is a natural ethanologen and ethanol production by a *Zymomonas* cell is shown in FIG. 1.

As an example, production of ethanol by a *Z. mobilis* cell of the invention is described. For production of ethanol, the recombinant *Z. mobilis* cell is brought in contact with medium that contains either a mixture of sugars, or either D-xylose or L-arabinose as the only sugar. Typically the medium contains a mixture of sugars including L-arabinose, D-xylose, and D-glucose. The medium may contain biomass hydrolysate that includes these sugars that are derived from treated cellulosic or lignocellulosic biomass.

When the mixed sugars concentration is high such that growth is inhibited, the medium may include sorbitol, mannitol, or a mixture thereof as disclosed in U.S. Pat. No. 7,629,156. Galactitol or ribitol may replace or be combined with sorbitol or mannitol. The *Z. mobilis* cells grow in the medium where fermentation occurs and ethanol is produced. The fermentation is run without supplemented air, oxygen, or other gases (which may include conditions such as anaerobic, microaerobic, or microaerophilic fermentation), for at least about 24 hours, and may be run for 30 or more hours. The timing to reach maximal ethanol production is variable, depending on the fermentation conditions. Typically, if inhibitors are present in the medium, a longer fermentation period is required. The fermentations may be run at temperatures that are between about 30° C. and about 37° C., at a pH of about 4.5 to about 7.5.

The present *Z. mobilis* cells may be grown in medium containing mixed sugars including D-xylose in laboratory scale fermenters, and in scaled up fermentation where commercial quantities of ethanol are produced. Where commercial production of ethanol is desired, a variety of culture methodologies may be applied. For example, large-scale production from the present *Z. mobilis* strains may be produced by both batch and continuous culture methodologies. A classical batch culturing method is a closed system where the composition of the medium is set at the beginning of the culture and not subjected to artificial alterations during the culturing process. Thus, at the beginning of the culturing process the medium is inoculated with the desired organism and growth or metabolic activity is permitted to occur adding nothing to the system. Typically, however, a "batch" culture is batch with respect to the addition of carbon source and attempts are often made at controlling factors such as pH and oxygen concentration. In batch systems the metabolite and biomass compositions of the system change constantly up to the time the culture is terminated. Within batch cultures cells moderate through a static lag phase to a high growth log phase and finally to a stationary phase where growth rate is diminished or halted. If untreated, cells in the stationary phase will eventually die. Cells in log phase are often responsible for the bulk of production of end product or intermediate in some systems. Stationary or post-exponential phase production can be obtained in other systems.

A variation on the standard batch system is the Fed-Batch system. Fed-Batch culture processes are also suitable for growth of the present *Z. mobilis* cells and comprise a typical batch system with the exception that the substrate is added in increments as the culture progresses. Fed-Batch systems are useful when catabolite repression is apt to inhibit the metabolism of the cells and where it is desirable to have limited amounts of substrate in the medium. Measurement of the actual substrate concentration in Fed-Batch systems is difficult and is therefore estimated on the basis of the changes of measurable factors such as pH and the partial pressure of waste gases such as $CO_2$. Batch and Fed-Batch culturing methods are common and well known in the art and examples may be found in Biotechnology: A Textbook of Industrial Microbiology, Crueger, Crueger, and Brock, Second Edition (1989) Sinauer Associates, Inc., Sunderland, Mass., or Deshpande, Mukund V., *Appl. Biochem. Biotechnol.,* 36, 227, (1992), herein incorporated by reference.

Commercial production of ethanol may also be accomplished with a continuous culture. Continuous cultures are open systems where a defined culture medium is added continuously to a bioreactor and an equal amount of conditioned medium is removed simultaneously for processing. Continuous cultures generally maintain the cells at a constant high liquid phase density where cells are primarily in log phase growth. Alternatively, continuous culture may be practiced with immobilized cells where carbon and nutrients are continuously added, and valuable products, by-products or waste products are continuously removed from the cell mass. Cell immobilization may be performed using a wide range of solid supports composed of natural and/or synthetic materials as is known to one skilled in the art.

Continuous or semi-continuous culture allows for the modulation of one factor or any number of factors that affect cell growth or end product concentration. For example, one method will maintain a limiting nutrient such as the carbon source or nitrogen level at a fixed rate and allow all other parameters to moderate. In other systems a number of factors affecting growth can be altered continuously while the cell concentration, measured by medium turbidity, is kept constant. Continuous systems strive to maintain steady state growth conditions and thus the cell loss due to medium being drawn off must be balanced against the cell growth rate in the culture. Methods of modulating nutrients and growth factors for continuous culture processes as well as techniques for maximizing the rate of product formation are well known in the art of industrial microbiology and a variety of methods are detailed by Brock, supra.

Particularly suitable for ethanol production is a fermentation regime as follows. The desired *Z. mobilis* cell of the present invention is grown in revival at about 30° C. to about 37° C. without shaking, then transferred to a shake flask with semi-complex medium at about 30° C. to about 37° C. with shaking at about 150 rpm in orbital shakers, and then transferred to the a seed fermentor containing similar medium. If desired, a series of seed fermentors may be required to produce the desired organism quantity. The seed culture is grown in the seed fermentor anaerobically until the desired organism density, when it is transferred to the production fermentor where the fermentation parameters are optimized for ethanol production. Typical inoculum volumes transferred from the seed tank to the production tank range from about 2% to about 20% v/v. Typical fermentation medium contains biomass hydrolysate in greater than 50% of the medium volume. A final concentration of about 10 mM sorbitol or mannitol may be present in the medium. The fermentation is controlled at pH 5.0-6.0 using caustic solution (such as ammonium hydroxide, potassium hydroxide, or sodium hydroxide) and either sulfuric or phosphoric acid. The temperature of the fermentor is controlled at 30° C.-35° C. In order to minimize foaming, antifoam agents (any class—silicone based, organic based etc) are added to the vessel as needed.

Any set of conditions described above, and additionally variations in these conditions that are well known in the art, are suitable conditions for production of ethanol the present recombinant *Zymomonas* cell.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

General Methods

The meaning of abbreviations is as follows: "kb" means kilobase(s), "bp" means base pairs, "nt" means nucleotide(s), "hr" means hour(s), "min" means minute(s), "sec" means second(s), "d" means day(s), "L" means liter(s), "mL" means milliliter(s), "µL" means microliter(s), "µg" means microgram(s), "ng" means nanogram(s), "mM" means millimolar, "µM" means micromolar, "nm" means nanometer(s), "µmol" means micromole(s), "pmol" means picomole(s), "Cm" means chloramphenicol, "Cm$^r$" or "Cm-R" means chloramphenicol resistant, "Cm$^s$" means chloramphenicol sensitive, "Sp$^r$" means spectinomycin resistance, "Sp$^s$" means spectinomycin sensitive, "DCO" means double cross over, "UTR" means untranslated region, "~" means approximately, "$OD_{600}$" means optical density at 600 nm.

Primers were synthesized by Sigma (St. Louis, Mo.) unless otherwise specified

Transformation of *Z. mobilis*

Competent cells of *Z. mobilis* were generated by first inoculating a 5 mL culture of MRMG5 medium from a frozen vial of *Z. mobilis* cells. The 5 mL culture was grown for ~18 h at 33° C. with shaking at 125 rpm. At this time, the 5 mL culture was diluted into 100 mL of MRM3G5 medium. This 100 mL culture was grown at 33° C. with 125 rpm shaking until the $OD_{600}$ reached ~0.4. At this time, the culture was placed on ice for 30 min and then the cells were harvested by centrifugation. The supernatant was removed, and the resulting cell pellet was resuspended in a 0° C. sterile solution of 10% (v/v) glycerol in water to a final volume of 20 mL. Cells were again harvested by centrifugation and the resulting cell pellet was resuspended in a 0° C. sterile solution of 10% glycerol in water to a final volume of 5 mL. Cells were again harvested by centrifugation and the resulting cell pellet was resuspended in a 0° C. sterile solution of 10% glycerol in water to a final volume of 0.5 mL. Aliquots of 0.05 mL were frozen separately at −80° C. until needed.

Plasmid DNA was introduced into *Z. mobilis* cells using electroporation, essentially as described in U.S. Pat. No. 5,514,583. Briefly, the 50-µl transformation reactions contained ~$10^{10}$ cells/ml in 10% (v/v) glycerol and 1-2 µg of non-methylated plasmid DNA that was isolated from transformed *E. coli* SCS110 cells. Control reactions were treated identically, but did not receive any plasmid DNA. The settings for the electroporator were 1.6 kv/cm, 200Ω, and 25 µF, and the gap width of the cuvette was 0.1 cm. Following electroporation, the transformation reactions were diluted with MMG medium and the cells were allowed to recover at 30° C. before they were plated on MMG medium that contained 1.5% agar (MMG agar plates) with or without antibiotics as indicated. Plates were incubated in an anaerobic chamber at 30-33° C., until colonies appeared. Additional details are described in the Examples.

Media

MMG medium: 50 g/L D-glucose, 10 g/L yeast extract, 5 g/L of tryptone, 2.5 g/L of $(NH_4)_2SO_4$, 0.2 g/L $K_2HPO_4$, and 1 mM $MgSO_4$ MRM3: 10 g/L yeast extract, 2 g/L KH$_2$PO$_4$, 1 g/L MgSO$_4$.7H$_2$O)
MRM3X10: MRM3 with 100 g/L D-xylose
MRM3G5: MRM3 with 50 g/L D-glucose
MRM3G10: MRM3 with 100 g/L D-glucose
MRM3A10: MRM3 with 100 g/L L-arabinose
MRM3A5: MRM3 with 50 g/L L-arabinose
HPLC Analysis Fermentation samples were taken at timed intervals and analyzed for ethanol and residual sugars using a Waters HPLC system (Alliance system, Waters Corp., Milford, Mass.); conditions=0.6 mL/min of 0.01 N H$_2$SO$_4$, injection volume=10 µL, column temperature=65° C., run time=30 min, detection by refractive index (maintained at 40° C.). The HPLC column was purchased from BioRad (Aminex HPX-87H, BioRad Inc., Hercules, Calif.). Analytes were quantified by refractive index detection and compared to known standards.

Z. mobilis Strain ZM4

Z. mobilis strain ZM4 is ATCC #31821; ZW1 is another name for the ZM4 strain.

GenBank accession number AE008692 (Seo et al., Nat. Biotechnol. 23 (1), 63-68 (2005)) and NCBI Reference: NC_006526.2 are both references to the genomic sequence of the ZM4 strain.

Zymomonas mobilis Strain Construction

A detailed description of the construction of the D-xylose-utilizing recombinant strain, ZW801-4, starting from the wild type parent strain, ZW1, is provided in U.S. Pat. No. 7,741, 119, which is herein incorporated by reference. Strain ZW801-4 was derived from strain ZW800, which was derived from strain ZW658, all as described in U.S. Pat. No. 7,741,084, which is herein incorporated by reference. ZW658 was constructed by integrating two operons, P$_{gap}$xylAB and P$_{gap}$taltkt, containing four D-xylose-utilizing genes encoding D-xylose isomerase (xylA), xylulokinase (xylB), transaldolase (tal), and transketolase (tkt), with coding regions from E. coli genes, into the genome of ZW1 (rename of strain ZM4; ATCC #31821) via sequential transposition events followed by adaptation on selective medium containing D-xylose to produce strain X13L3, which was renamed ZW641. Further adaptation of ZW641 on D-xylose-containing growth media gave rise to ZW658, which grows much better in D-xylose and was deposited under the Budapest Treaty as ATCC PTA-7858. As disclosed in commonly owned U.S. Pat. No. 7,989, 206, which is herein incorporated by reference, ZW658 has much more D-xylose isomerase activity due to a point mutation in the promoter (P$_{gap}$) expressing the xylA coding region. This promoter (SEQ ID NO:31) herein called either the 801 GAP promoter or the Super GAP promoter or P$_{gapS}$, has a "T" instead of "G" in position 116 in SEQ ID NO:31, when compared to the native P$_{gap}$ in ZW641 (the 641GAP promoter). The P$_{gapS}$ has expression strength 3 to 4 times higher than the P$_{gap}$ in Z. mobilis.

In ZW658, the gene encoding glucose-fructose oxidoreductase was insertionally inactivated using host-mediated, double-crossover, homologous recombination and spectinomycin resistance as a selectable marker to create strain ZW800. The spectinomycin resistance marker, which was bounded by loxP sites, was removed by site specific recombination using Cre recombinase to create strain ZW801-4.

Strain ZW705 was produced from ZW804-1 by adapting for growth under stress conditions in medium containing ammonium acetate as described in U.S. Pat. No. 8,247,208, which is incorporated herein by reference.

Figure 2:
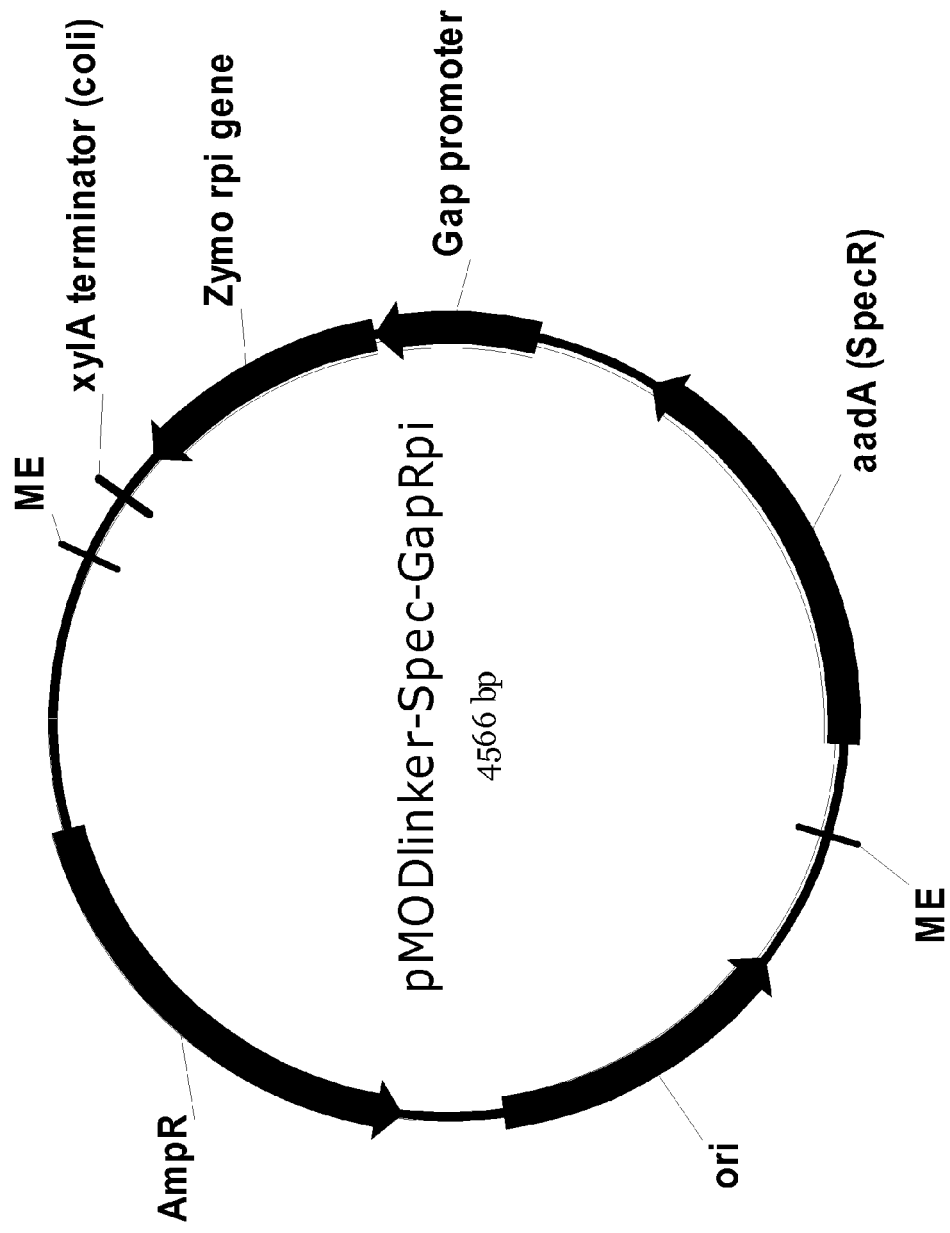
FIG. 2 shows a plasmid map of pMODlinker-Spec-GapRpi.

The I strain was produced from strain ZW801-4, as described in US 2013/0157331, Examples 1 and 2, which are incorporated herein by reference. The I strain resulted from random integration of a transposome generated from pMODlinker-Spec-GapRpi (FIG. 2) which includes a Z. mobilis RPI expression cassette (Pgap-RPI; SEQ ID NO:32) and the Spec$^r$-cassette. The site of insertion for the RPI expression transposon in the I strain was determined by DNA sequencing to be between nts 543506 and 543507 of the Z. mobilis genome (GenBank accession number AE008692; Seo et al., Nat. Biotechnol. 23 (1), 63-68 (2005)). Sequencing of the insertion region showed that integration of the transposon caused a frame shift at the 3' end of the open reading frame of the pnp gene that codes for polyribonucleotide nucleotidyl transferase. The resulting open reading encodes a mutant protein which is missing the last 39 amino acid residues of the native protein (retains 709 amino acids starting from the N-terminus) and has 14 new amino acids at its C-terminus (SEQ ID NO:21). The I strain was found to have better growth in D-xylose medium than parental strains.

Example 1

Construction for the Deletion of ZMO0353 Open Reading Frame

A plasmid designated p323del (SEQ ID NO:33) was constructed to facilitate the deletion from the Zymomonas mobilis genome of the open reading frame designated as ZMO0353 (SEQ ID NO:1) in the published genome sequence of Z. mobilis strain ZM4 (GenBank accession number AE008692; Seo et al., Nat. Biotechnol. 23 (1), 63-68 (2005)).

p323del was derived from pMODlinker-CM, the construction of which is described in US Patent Application Publication 20130157332, Example 3, which is incorporated herein by reference. A DNA fragment that confers resistance to chloramphenicol (Cm$^r$; Cm$^r$ coding region with its associated promoter from the commercially available plasmid pACYC184 (Boca Scientific, Boca Raton, Fla.)) was inserted between the NotI and PacI sites of the pMOD-Linker-Spec plasmid, which is described in detail in U.S. Pat. No. 7,989, 206, replacing the DNA fragment that confers resistance to spectinomycin (Spec$^r$) to create pMODlinker-CM. pMODlinker-CM has a loxP-flanked Cm$^r$-cassette that is located between the two mosaic ends (ME) that Tn5 transposase interacts with to form transposomes.

Figure 3:
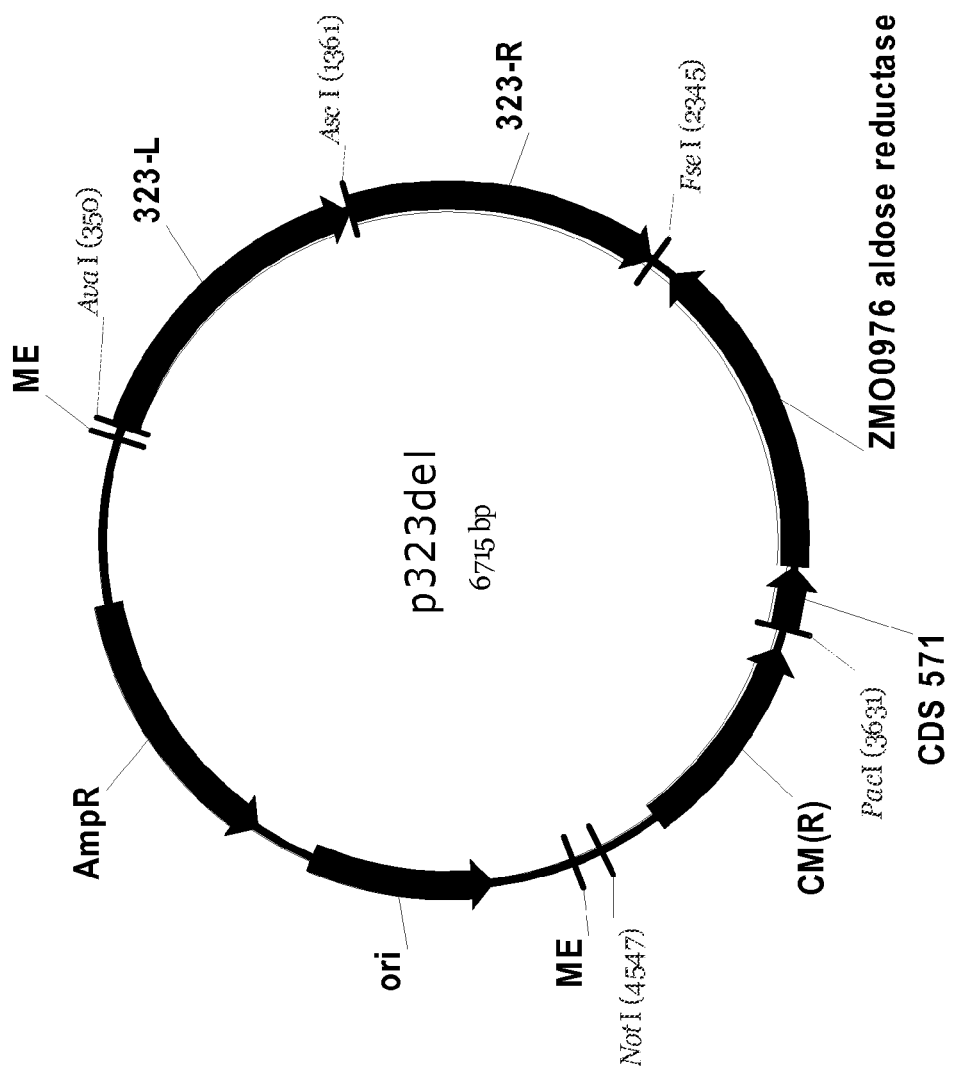
FIG. 3 shows a plasmid map of p323del.

A schematic of the plasmid p323del is shown in FIG. 3. The region designated 323-L (from position 355 to 13580) correlates to nucleotides 350392-351395 of the ZM4 genome sequence (GenBank accession number AE008692; Seo et al., Nat. Biotechnol. 23 (1), 63-68 (2005)) which is located 5' adjacent to ZMO0353. The region designated 323-R (from position 1367 to 2338) correlates to nucleotides 352740-353711 in the ZM4 genome sequence which is located 3' adjacent to ZMO0353.

Nucleotides 2412 to 3625 of p323del, designated as ZMO0976 and CDS571, correlate to nucleotides 992143-993230 of the ZM4 genome sequence. This sequence contains a coding region for aldose reductase designated as ZMO0976 in the ZM4 genome sequence and an upstream region containing a putative promoter.

Sequences from position 3690 to 309 are from the pMODlinker-CM plasmid. The restriction enzymes used to construct the plasmid are shown in FIG. 3.

Example 2

Construction of ZMO0353 Open Reading Frame Deletion Strain

D-xylose utilizing Z. mobilis strain AR3 7-31 was transformed with p323del (Example 1). Strain AR3 7-31 was derived from strain ZW705 (see General Methods). Strain AR3 7-31 was isolated following growth of strain ZW705 in a turbidostat as described in U.S. Pat. No. 8,476,048, which is incorporated herein by reference; the strain is also called therein Adapted 7-31. In this continuous flow culture device the concentration of ammonium acetate and ethanol was increased over time in a hydrolysate medium. The entire genome of AR3 7-31 was sequenced and compared to the sequence of the ZW705 genome. Strain AR3 7-31 was found to have a genetic modification in the ZMO1432 open reading frame of the Zymomonas mobilis genome (NCBI Reference: NC_006526.2), in which ZMO1432 is annotated as encoding a "fusaric acid resistance protein".

Competent cells of strain AR3 7-31 were prepared as described in General Methods. The competent cells were transformed by electroporation with 1 μg of the p323del plasmid described in Example 1. Transformed cells were resuspended in 1 mL MMG medium and were incubated for three hours at 33° C. The cells were then harvested by centrifugation, the supernatant was removed, and the cells were resuspended in 200 μL MMG medium. The resuspended cells were spread onto two MMG agar plates (100 μL per plate) containing 120 μg/mL chloramphenicol (Biomyx). The agar plates were incubated for three days at 33° C. in a sealed box containing a Gas Pak (Mitsubishi chemicals) to maintain anaerobicity. Three of the chloramphenicol resistant colonies which were observed to grow on the plates were picked and re-streaked on plates of the same medium. These new plates were incubated for an additional three days under the same conditions. During growth under chloramphenicol selection, in a first recombination event the entire plasmid is integrated into the genome.

After the three day incubation, three single colonies from these plates were picked and streaked onto an MMG plate and incubated under the same conditions for one day. After the one day incubation, a single colony of each of the three streaks was picked and restreaked again onto an MMG plate and incubated for an additional day. At this time, a single colony from each of the three streaks was picked and streaked onto a separate MRM3X10 plate. After four days incubation, cells were picked from these plates and streaked onto separate MMG plates to get well separated single colonies. After one day incubation, single colonies were picked and screened by PCR to confirm the deletion of the ZMO0353 open reading frame. Primers 323-F1 and 323-R6 (SEQ ID NOs:34 and 35, respectively) were used for the PCR reaction. Strains which were confirmed to have the desired deletion were designated AR3 D323. The period of growth on medium lacking chloramphenicol allows a second recombination to occur that deletes the entire plasmid and the ZMO0353 sequence. Growth on medium containing D-xylose as the carbon source uses expression of the aldose reductase gene on the original plasmid to create selection for the second recombination event. Aldose reductase was previously found to have a detrimental effect on D-xylose utilization, as disclosed in US patent application publication 2013-0157332.

Example 3

Improved D-Xylose Use by ZMO0353 Open Reading Frame Deletion Strain in Medium Containing D-Glucose and D-Xylose The carbohydrate consumption ability of an AR3 D323 strain described in Example 2 was compared to the parent strain AR3 7-31. Two 2 mL cultures of MRM3G5 medium were inoculated from frozen stock vials of each strain (labeled a and b for each strain). All four cultures were incubated for ~20 h with shaking (125 rpm) at 33° C. At this time, 3 mL of fresh MRM3G5 medium was added to each culture, and the cultures were incubated under the same conditions for an additional 5 h. At this time, the $OD_{600}$ of each culture was measured, and a sufficient volume of each was added to 10 mL of MRM3X10 medium to give a calculated $OD_{600}$ of 0.05. These 10 mL cultures were incubated at 33° C. with shaking (125 rpm) for 144 h. Samples were removed at the times indicated in Tables 1 and 2, and the concentrations of the D-xylose and ethanol in each culture were determined by HPLC as described in General Methods.

TABLE 1

D-xylose utilization in MRM3X10 cultures

| | Xylose g/L remaining | | | | | |
|---|---|---|---|---|---|---|
| Time | 0 | 23 | 46 | 71 | 93 | 119 | 144 |
| AR3 7-31 a | 96.1 | 74.1 | 43.4 | 22.3 | 11.7 | 7.9 | 7.1 |
| AR3 7-31 b | 96.1 | 73.4 | 41.5 | 19.3 | 9.2 | 6.0 | 5.3 |
| AR3D323 a | 96.1 | 66.9 | 29.4 | 8.9 | 3.3 | 2.2 | 2.1 |
| AR3D323 b | 96.1 | 70.4 | 30.8 | 9.3 | 3.7 | 2.4 | 2.3 |

TABLE 2

Ethanol production in MRM3X10 cultures

| | Ethanol g/L | | | | | |
|---|---|---|---|---|---|---|
| Time | 0 | 23 | 46 | 71 | 93 | 119 | 144 |
| AR3 7-31 a | 0.0 | 7.5 | 18.5 | 26.6 | 31.0 | 32.3 | 32.3 |
| AR3 7-31 b | 0.0 | 7.7 | 19.4 | 28.0 | 32.3 | 33.4 | 33.4 |
| AR3D323 a | 0.0 | 10.4 | 23.7 | 31.3 | 34.6 | 34.9 | 34.7 |
| AR3D323 b | 0.0 | 9.1 | 23.4 | 31.9 | 35.0 | 35.2 | 34.9 |

As indicated in Tables 1 and 2, the AR3 D323 strain consumed D-xylose and produced ethanol more quickly than the AR3 7-31 strain under these conditions, demonstrating the advantage conferred by the deletion of open reading frame ZMO0353.

Example 4

Construction of a Plasmid for Insertion of Arabinose Utilization Genes in the pnp Locus A plasmid designated pZBpnpIBAD was constructed based on plasmid pZX6 (SEQ ID NO:36), the construction of which is described in US Patent Application Publication 20130157332, Example 2, which is incorporated herein by reference. pZX6 is a double cross over Zymomonas-E. coli shuttle vector that directs integration into the Z. mobilis genome in the endogenous pnp gene (designated ZMO0549 in GenBank accession number AE008692) encoding polynucleotide phosphorylase near the end of the pnp coding sequence, and replaces a segment of the pnp coding sequence (from nt-2,084 to nt-2,188) in the *Z. mobilis* genome. Make sure the position is designated using the same sequence numbering that you are using. The 1,318 bp PNP-L fragment (SEQ ID NO:37) is a segment of the pnp coding sequence (SEQ ID NO:13) from nt-767 to nt-2,084, while the 1,225 bp PNP-R fragment (SEQ ID NO:38) includes the last 59 bp (from nt-2189 to nt-2247) of the pnp coding sequence and 1,166 bp of downstream genomic sequence. pZX6 includes a 2,582 bp *Z. mobilis* genomic DNA fragment containing a replication origin allowing the vector to replicate in *Zymomonas* cells (Zymo DNA in FIG. 4), a 911 bp chloramphenicol resistance marker (Cm-R) for selection of either *E. coli* or *Z. mobilis* transformants, and a 909-bp *E. coli* replication origin (Ori).

Figure 4:
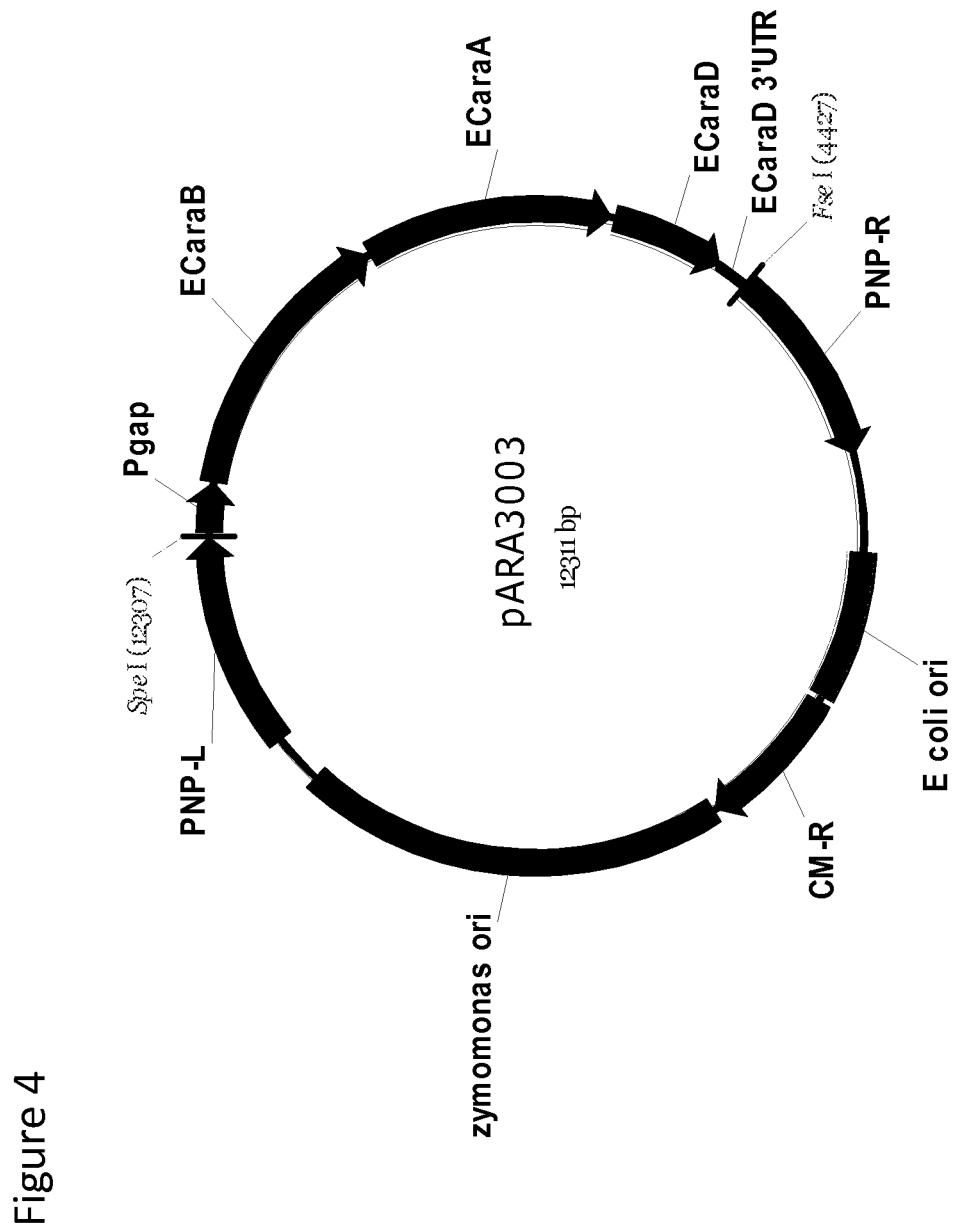
FIG. 4 shows a plasmid map of pARA3003.

To include genes for engineering of *Zymomonas mobilis* for arabinose utilization, an SpeI-FseI DNA fragment (SEQ ID NO:39) containing a chimeric $P_{gap}$-araBAD operon was inserted into pZX6 between the SpeI and FseI sites to replace the $P_{gapT}$-tal-tkt operon and the $P_{eno}$-rpi-rpe operon, resulting in the 12,311-bp DCO shuttle vector designated pARA3003 and shown in FIG. 4. The $P_{gap}$-araBAD operon is described in US 2011-0143408, Example 1, which is incorporated herein by reference. The SpeI-FseI fragment is the same as the SpeI-EcoRI fragment of pARA354 (FIG. 3 in US 2011-0143408) with addition of sequence including an FseI site 3' to the operon. The SpeI-FseI DNA fragment contains a 305-bp *Z. mobilis* $P_{gap}$ (promoter of the *Z. mobilis* glyceraldehyde-3-phosphate dehydrogenase encoding gene), the 1,701-bp araB coding region from *E. coli* (encoding L-ribulose kinase; ECaraB), the 1,503-bp araA coding region from *E. coli* (encoding L-arabinose isomerase; ECaraA), the 696-bp araD coding region from *E. coli* (encoding L-ribulose-5-phosphate 4-epimerase; ECaraD), and a 166-bp 3'UTR from the ECaraD gene (ECaraD 3'UTR).

Figure 5:
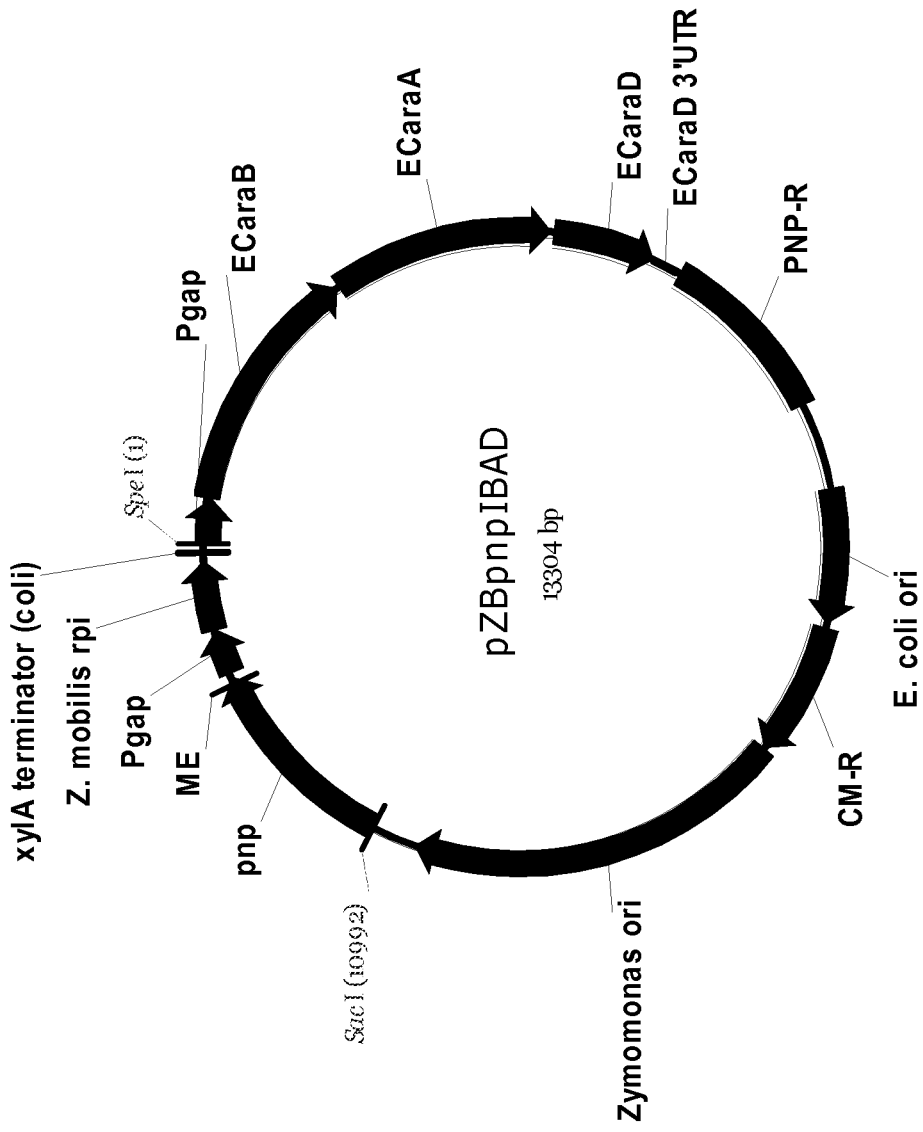
FIG. 5 shows a plasmid map of pZBpnpIBAD.

To generate pZBpnpIBAD (shown in FIG. 5), the SacI/SpeI fragment in pARA3003 was replaced with a new SacI/SpeI fragment that was generated by overlap PCR. Primer IRpi-F (SEQ ID NO:40) is a forward primer with a SacI site followed by 24 nts that bind to the pnp gene upstream from the transposon insertion site (ME) for the loxP-flanked Spec$^r$-cassette and Pgap-RPI expression cassette that is present in the genome of the *Z. mobilis* I strain (see General Methods). Primer IRpi-o-R (SEQ ID NO:41) is a reverse primer. Its last 20 nts hybridize downstream from the same ME site, just upstream from the lox-flanked Spec$^r$-cassette that is present in the I strain, while its first 16 nts correspond to the reverse complement of the first 16 nts of the Pgap promoter that drives the RPI expression in the I strain. Primers IRpi-F and IRpi-o-R were used to PCR-amplify the pnp gene region from the I strain genomic DNA to generate one of the DNA fragments for the overlap PCR reaction.

The other fragment for the overlap PCR reaction was generated as follows. Primer IRpi-o-F (SEQ ID NO:42) is a forward primer and is the reverse complement of Primer IRpi-o-R. Primer IRpi-R (SEQ ID NO:43) is a reverse primer that contains a SpeI site at its 5' end followed by 24 nts that hybridize just downstream from the XylA terminator, which is at the 3' end of the Pgap-RPI expression cassette that is present in the I strain's pnp locus. IRpi-o-F and IRpi-R were used to PCR-amplify the Pgap-RPI gene region from the I strain. The two PCR products described above were then combined for the overlap PCR reaction using only primers IRpi-F and IRpi-R. The resulting overlap PCR fragment contains a portion of the transposon-interrupted pnp gene region of the I strain genome (including the ME that caused the frameshift near the 3' end of the pnp gene, which resulted in the truncated pnp protein in the I strain (see General Methods), fused to the Pgap-Rpi expression cassette. The only essential difference between the overlapping PCR fragment described above and the original fragment that would have been amplified from the I strain using primers IRpi-F and IRpi-R alone is the absence of the loxP-flanked Spec$^r$-cassette in the overlap PCR product. This new 2340 bp PCR-amplified chimeric DNA molecule (SEQ ID NO:44) was then used for the construction of plasmid pZBpnpIBAD as described below.

The final step in the construction of pZBpnpIBAD was ligation of the 2.3 kb SacI/SpeI fragment of the overlap PCR reaction product described above with the 11 kb SacI/SpeI fragment of pARA3003. The ligation product was used to transform *E. coli* strain DH10B, and transformants were selected on LB agar plates containing 25 µg/mL chloramphenicol. Plasmid DNA was isolated from a Cm$^r$ colony and the sequence of the plasmid was verified by sequencing.

Example 5

Construction of a *Z. mobilis* Strain that Utilizes D-Xylose and Arabinose, Expresses Rpi, has pnp Insertion, and ZMO0353 Deletion Competent cells of strains AR3 7-31 and AR3 D323 1 were prepared as described in General Methods and transformed with 1 µg of the pZBpnpIBAD plasmid described in Example 4 by electroporation. Transformants were selected by plating on MMG agar plates containing 120 µg/mL chloramphenicol. Transformants of AR3 7-31 were designated "AR3BAD" and those of AR3 D323 1 were designated "AR3D323BAD". Single colonies were selected and restreaked on an MMG chloramphenicol plate. Eight single colonies were selected from this plate and restreaked onto an MRM3A10 plate. Colonies were then picked and restreaked on MRM3A10 plates and incubated for two days. This replating on MRM3A10 was repeated three additional times. After the fourth plating on MRM3A10 agar, four colonies each of AR3BAD and AR3D323BAD were picked and streaked onto an MRM3X10 agar plate and an MMG agar plate. All four streaks of AR3BAD cells exhibited very poor growth on the MRM3X10 agar, while all four streaks of AR3D323BAD cells exhibited visible growth within 24 hours. Individual colonies from the MMG agar plates (on which both strains grew well) were streaked onto MMG agar containing 120 µg/mL chloramphenicol to confirm that the pZBpnpIBAD plasmid had recombined with the chromosome, resulting in loss of the chloramphenicol resistance marker. Four colonies each of AR3BAD and AR3D323BAD which were confirmed to be chloramphenicol sensitive were saved for further evaluation.

Example 6

Increased Consumption of L-Arabinose and D-Xylose, and Production of Ethanol in ZMO0353 Deletion Strain The four separate colonies each of AR3BAD and AR3D323BAD described in Example 5 were further evaluated for the ability to consume different carbohydrates. All eight strains were grown for ~18 hours in 2 mL cultures of MRM3G5 medium inoculated from frozen vials. Cultures were incubated at 33° C. in 15 mL tubes with shaking at 125 rpm. After 18 h, $OD_{600}$ was measured, and sufficient volume was transferred to inoculate 10 mL cultures of either MRM3A5 or MRM3X10 to a calculated final OD$_{600}$ of 0.06. These 10 mL cultures were incubated at 33° C. with shaking at 125 rpm, and samples were removed at the times indicated in Tables 3, 4, 5, and 6. Concentrations of the primary carbohydrate (D-xylose or L-arabinose) and ethanol in each culture were determined by HPLC as described in General Methods.

TABLE 3

D-xylose utilization in MRM3X10 cultures

D-xylose concentration (g/L) remaining

| Time (hr) | 0 | 16 | 24 | 43 | 67 |
|---|---|---|---|---|---|
| AR3 BAD 1 | 96.8 | 94.8 | 92.2 | 85.5 | 77.0 |
| AR3 BAD 2 | 96.8 | 94.2 | 93.0 | 88.4 | 82.7 |
| AR3 BAD 3 | 96.8 | 93.6 | 91.1 | 82.9 | 72.8 |
| AR3 BAD 4 | 96.8 | 93.5 | 91.6 | 84.2 | 75.2 |
| AR3D323 BAD 1 | 96.8 | 87.7 | 66.4 | 14.9 | 0.8 |
| AR3D323 BAD 2 | 96.8 | 81.2 | 55.9 | 13.5 | 0.5 |
| AR3D323 BAD 3 | 96.8 | 85.9 | 61.0 | 9.9 | 0.5 |
| AR3D323 BAD 4 | 96.8 | 88.0 | 65.8 | 16.6 | 0.8 |

TABLE 4

Ethanol production in MRM3X10 cultures

Ethanol concentration (g/L)

| Time (hr) | 0 | 16 | 24 | 43 | 67 |
|---|---|---|---|---|---|
| AR3 BAD 1 | 0.0 | 0.8 | 1.7 | 4.0 | 6.9 |
| AR3 BAD 2 | 0.0 | 0.9 | 1.3 | 2.9 | 4.7 |
| AR3 BAD 3 | 0.0 | 1.3 | 2.0 | 4.7 | 8.3 |
| AR3 BAD 4 | 0.0 | 1.1 | 1.9 | 4.4 | 7.6 |
| AR3D323 BAD 1 | 0.0 | 3.3 | 12.1 | 30.9 | 37.1 |
| AR3D323 BAD 2 | 0.0 | 6.0 | 15.9 | 31.4 | 37.1 |
| AR3D323 BAD 3 | 0.0 | 4.1 | 14.1 | 33.5 | 37.7 |
| AR3D323 BAD 4 | 0.0 | 3.1 | 12.3 | 29.4 | 36.2 |

TABLE 5

Arabinose utilization in MRM3A5 cultures

Arabinose concentration (g/L) remaining

| Time (hr) | 0 | 16 | 24 | 43 | 67 | 99 |
|---|---|---|---|---|---|---|
| AR3 BAD 1 | 48.8 | 45.9 | 40.5 | 27.7 | 18.5 | 12.7 |
| AR3 BAD 2 | 48.8 | 46.4 | 41.9 | 29.8 | 21.4 | 14.8 |
| AR3 BAD 3 | 48.8 | 43.1 | 37.1 | 24.1 | 17.3 | 12.3 |
| AR3 BAD 4 | 48.8 | 43.5 | 37.8 | 25.2 | 18.1 | 12.8 |
| AR3D323 BAD 1 | 48.8 | 41.9 | 30.2 | 12.6 | 6.4 | 3.6 |
| AR3D323 BAD 2 | 48.8 | 37.5 | 25.7 | 11.3 | 6.0 | 3.2 |
| AR3D323 BAD 3 | 48.8 | 41.1 | 30.5 | 14.9 | 8.8 | 4.9 |
| AR3D323 BAD 4 | 48.8 | 41.8 | 30.3 | 13.1 | 6.7 | 3.5 |

TABLE 6

Ethanol production in MRM3A5 cultures

Ethanol concentration (g/L)

| Time (hr) | 0 | 16 | 24 | 43 | 67 | 99 |
|---|---|---|---|---|---|---|
| AR3 BAD 1 | 0.0 | 1.2 | 3.1 | 8.2 | 12.3 | 15.0 |
| AR3 BAD 2 | 0.0 | 1.0 | 2.6 | 7.4 | 11.0 | 14.1 |
| AR3 BAD 3 | 0.0 | 2.2 | 4.5 | 9.7 | 12.7 | 15.0 |
| AR3 BAD 4 | 0.0 | 2.0 | 4.2 | 9.4 | 12.5 | 14.9 |
| AR3D323 BAD 1 | 0.0 | 2.6 | 7.3 | 14.8 | 17.6 | 18.4 |
| AR3D323 BAD 2 | 0.0 | 4.4 | 9.3 | 15.5 | 17.8 | 18.7 |
| AR3D323 BAD 3 | 0.0 | 2.8 | 7.1 | 13.8 | 16.2 | 17.7 |
| AR3D323 BAD 4 | 0.0 | 2.6 | 7.3 | 14.7 | 17.6 | 18.6 |

As indicated in the tables, the AR3D323BAD strains consumed L-arabinose or D-xylose more quickly than the AR3BAD strains under these conditions, demonstrating the advantage conferred by the deletion of open reading frame ZMO0353 on the rate of consumption of 5-carbon monosaccharides. Ethanol production was also faster in the ΔZMO0353 strains in both D-xylose and L-arabinose media.

What is claimed is:

1. A recombinant *Zymomonas mobilis* cell that comprises D-xylose utilization pathway genes and that utilizes D-xylose as a carbon source, wherein the recombinant cell comprises at least one genetic modification of a genomic nucleic acid comprising a nucleic acid sequence having at least 95% sequence identity to the nucleotide sequence of SEQ ID NO: 1, wherein the at least one genetic modification disrupts expression of a functional enzyme encoded by the nucleic acid sequence, and wherein D-xylose utilization by the recombinant cell is increased as compared to D-xylose utilization in a cell that is identical except for lacking the genetic modification.

2. The recombinant cell of claim 1, wherein a culture of the recombinant cells starting with an $OD_{600}$ of 0.05 uses at least 56 g/L±10% of D-xylose when grown at 33° C. with shaking for 46 hours in medium initially containing 96 g/L±10% of D-xylose.

3. The recombinant cell of claim 1, wherein the cell further comprises L-arabinose utilization pathway genes and utilizes L-arabinose as a carbon source, and wherein L-arabinose utilization by the recombinant cell is increased as compared to L-arabinose utilization in a cell that is identical except for lacking the genetic modification.

4. The recombinant cell of claim 3, wherein a culture of the recombinant cells starting with an $OD_{600}$ of 0.06 uses at least 28 g/L±10% of L-arabinose when grown at 33° C. with shaking for 43 hours in medium initially containing 49 g/L±10% of L-arabinose.

5. The recombinant cell of claim 1 or 3, wherein the D-xylose utilization pathway genes encode D-xylose isomerase, xylulokinase, transketolase, and transaldolase.

6. The recombinant cell of claim 3, wherein a culture of the recombinant cells starting with an $OD_{600}$ of 0.06 uses at least 20 g/L±10% of D-xylose when grown at 33° C. with shaking for 43 hours in medium initially containing 97 g/L±10% of D-xylose and uses at least 28 g/L±10% of L-arabinose when grown at 33° C. with shaking for 43 hours in medium initially containing 49 g/L±10% of L-arabinose.

7. The recombinant cell of claim 3, wherein the L-arabinose utilization pathway genes encode L-arabinose isomerase, L-ribulose kinase, and L-ribulose-5-phosphate 4-epimerase.

8. The recombinant cell of claim 1 or 3, wherein the genetic modification is an insertion, deletion, or mutation in the genomic nucleic acid.

9. The recombinant cell of claim 1 or 3, further comprising at least one of the following:
   a) at least one genetic modification that reduces expression of a glucose-fructose oxidoreductase gene as compared to said cell that is identical except for lacking the genetic modification;
   b) at least one genetic modification that increases expression of a ribose-5-phosphate isomerase gene as compared to said cell that is identical except for lacking the genetic modification; and
   c) at least one genetic modification in the sequence of an endogenous gene encoding a polynucleotide phosphorylase that shortens the coding region resulting in expression of a C-terminal truncated polynucleotide phosphorylase protein.

10. A process for producing ethanol comprising:
   a) providing the recombinant *Zymomonas mobilis* cell of claim 1 or 3, optionally comprising at least one of the following:
      i) at least one genetic modification that reduces expression of a glucose-fructose oxidoreductase gene as compared to said cell that is identical except for lacking the genetic modification;
      ii) at least one genetic modification that increases expression of a ribose-5-phosphate isomerase gene as compared to said cell that is identical except for lacking the genetic modification; and
      iii) at least one genetic modification in the sequence of an endogenous gene encoding a polynucleotide phosphorylase that shortens the coding region resulting in expression of a C-terminal truncated polynucleotide phosphorylase protein; and
   b) culturing the recombinant *Zymomonas mobilis* cell of (a) in a medium comprising at least one of D-xylose and L-arabinose, whereby the at least one of D-xylose and L-arabinose is converted to ethanol.

11. The process of claim 10, wherein the medium comprises a mixture of sugars comprising D-xylose and L-arabinose, or either D-xylose or L-arabinose as the only sugar.

12. The process of claim 10, wherein ethanol production is increased as compared to a process that is identical except that the recombinant *Zymomonas mobilis* cell lacks the genetic modification.

* * * * *